(12) United States Patent
Miura et al.

(10) Patent No.: US 9,315,493 B2
(45) Date of Patent: Apr. 19, 2016

(54) PHENYLPYRIDINE DERIVATIVE AND DRUG CONTAINING SAME

(75) Inventors: Toru Miura, Saitama (JP); Seiichi Sato, Tokyo (JP); Hajime Yamada, Tokyo (JP); Junya Tagashira, Tokyo (JP); Toshiaki Watanabe, Tokyo (JP); Ryohei Sekimoto, Osaka (JP); Rie Ishida, Saitama (JP); Hitomi Aoki, Tokyo (JP); Tadaaki Ohgiya, Saitama (JP)

(73) Assignee: KOWA COMPANY, LTD., Nagoya-shi (JP)

( * ) Notice: Subject to any disclaimer, the term of this patent is extended or adjusted under 35 U.S.C. 154(b) by 89 days.

(21) Appl. No.: 14/005,046

(22) PCT Filed: Mar. 13, 2012

(86) PCT No.: PCT/JP2012/001709
§ 371 (c)(1),
(2), (4) Date: Sep. 13, 2013

(87) PCT Pub. No.: WO2012/124311
PCT Pub. Date: Sep. 20, 2012

(65) Prior Publication Data
US 2014/0011823 A1    Jan. 9, 2014

(30) Foreign Application Priority Data
Mar. 14, 2011 (JP) ................... 2011-055691

(51) Int. Cl.
| *A61K 31/505* | (2006.01) |
| *C07D 413/14* | (2006.01) |
| *C07D 401/14* | (2006.01) |
| *A61K 31/506* | (2006.01) |

(52) U.S. Cl.
CPC ............ *C07D 413/14* (2013.01); *A61K 31/506* (2013.01); *C07D 401/14* (2013.01)

(58) Field of Classification Search
CPC ... C07D 413/14; C07D 401/14; A61K 31/505
USPC .................. 514/273, 269; 544/296
See application file for complete search history.

(56) References Cited

U.S. PATENT DOCUMENTS

| 5,472,967 A | 12/1995 | Hoornaert et al. |
| 8,778,954 B2 * | 7/2014 | Miura et al. ............ 514/269 |
| 2012/0165353 A1 | 6/2012 | Miura et al. |

FOREIGN PATENT DOCUMENTS

| CN | 102639527 A | 8/2012 |
| EP | 2399917 A1 | 12/2011 |
| EP | 2420501 A1 | 2/2012 |
| JP | 5-271228 A | 10/1993 |
| JP | 5-331165 A | 12/1993 |
| JP | 6-211845 A | 8/1994 |
| JP | 7-179456 A | 7/1995 |
| WO | 95/22543 A1 | 8/1995 |
| WO | 2008/062905 A2 | 5/2008 |
| WO | 2008/084303 A1 | 7/2008 |
| WO | 2008/096820 A1 | 8/2008 |
| WO | 2008/096829 A1 | 8/2008 |
| WO | 2008/143262 A1 | 11/2008 |
| WO | 2010/095462 A1 | 8/2010 |
| WO | 2010/119700 A1 | 10/2010 |
| WO | 2011/040004 A1 | 4/2011 |

OTHER PUBLICATIONS

Schmeider, Roland, E., "Mechanisms for the Clinical Benefits of Angiotensin II Receptor Blockers", American Journal of Hypertension, 2005, vol. 18, No. 5, Part 1, pp. 720-730.
Siragy, Helmy, M., "Evidence for Benefits of Angiotensin Receptor Blockade Beyond Blood Pressure Control", Current Hypertension Reports, 2008, vol. 10, pp. 261-267.
The Shiga Microalbuminuria Reduction Trial (SMART), "Reduction of Microalbuminuria in Patients with Type 2 Diabetes", Diabetes Care, 2007, vol. 30, No. 6, pp. 1581-1583.
Sarafidis, PA, et al., "Protection of the kidney by thiazolidinediones: An assessment from bench to bedside", Kidney International, 2006, vol. 70, pp. 1223-1233.
Nesto, Richard, W. et al., "Thiazolidinedione Use, Fluid Retention, and Congestive Heart Failure: A Consensus Statement From the American Heart Association and American Diabetes Association", Circulation, 2003, vol. 108, pp. 2941-2948.

(Continued)

*Primary Examiner* — James O Wilson
*Assistant Examiner* — Ebenezer O Sackey

(57) ABSTRACT

The present invention provides: a compound represented by general formula (I) below, that has both angiotensin II receptor antagonism and a PPARγ activation effect and that is useful as a preventative and/or therapeutic agent for high blood pressure, cardiac disease, arteriosclerosis, type-2 diabetes, and the like; and a drug composition containing the compound. General formula (I) (in the formula: ring A represents a pyridine ring; ring B represents a tetrazole ring or an oxadiazol-5(4H)-one ring; X represents C—$R^5$ or a nitrogen atom; $R^1$ represents an alkyl group; $R^2$ represents an alkyl group or a cycloalkyl group; and $R^3$, $R^4$, and $R^5$ each independently represents a hydrogen atom, a halogen atom, an alkyl group, an alkoxy group or similar.

3 Claims, No Drawings

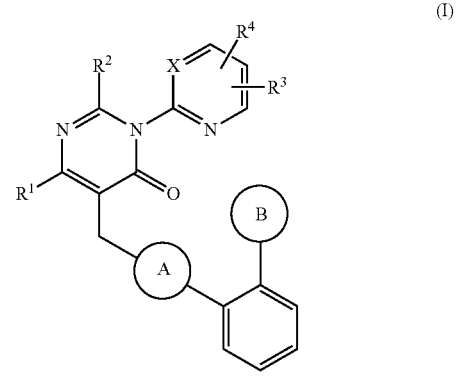

(56) References Cited

OTHER PUBLICATIONS

Gross, Barbara, et al., "PPAR agonists: multimodal drugs for the treatment of type-2 diabetes", Best Practice & Research Clinical Endocrinology & Metabolism, 2007, vol. 21, vol. 4, pp. 687-710.
Walcher, Daniel, et al., "Insulin resistance and cardiovascular disease: the role of PPARg activators beyond their anti-diabetic action", Diabetes and Vascular Disease Research, 2004, vol. 1. pp. 76-81.
Patel, Chetan, et al., "Thiazolidinediones, peripheral oedema and congestive heart failure: what is the evidence?", Diabetes and Vascular Disease Research, 2005, vol. 2, pp. 61-66.
Semple, Robert K, et al., "PPARg and human metabolic disease", The Journal of Clinical Investigation, 2006, vol. 116, No. 3, pp. 581-589.
Sotiropoulos, Konstantinos, B., et al., "Adipose-specific effect of rosiglitazone on vascular permeability and proten kinase C activation: novel mechanism for PPARg agonists's effects on edema and weight gain", The FASEB Journal, 2006, vol. 20, pp. 1203-1205, E367-E380.
Benson, Stephen, C., et al., "Identification of Telmisartan as a Unique Angiotensin II Receptor Antagonist With Selective PPARg Modulating Activity", Hypertension, 2004, vol. 43, pp. 993-1002.
Schupp, Michael, et al, "Angiotensin Type 1 Receptor Blockers Induce Peroxisome Proliferator-Activated Receptor-g Activity", Circulation, 2004, vol. 109, pp. 2054-2057.
International Search Report dated Apr. 10, 2012, issued in corresponding application No. PCT/JP2012/001709.
Written Opinion for PCT/JP2012/001709, Mailing Date of Apr. 10, 212, (2012).
Notification concerning Transmittal of Translation of the International Preliminary Report on Patentability (Form PCT/IB/326) of International Application No. PCT/JP2012/001709, mailed Sep. 26, 2013 with forms PCT/IB/338, PCT/IB/373 and PCT/ISA/237.
Eurasian Search Report dated Mar. 13, 2012, issued in corresponding Eurasian Patent Application No. 201391314, (1 page).
Chinese Office Action dated Apr. 21, 2014, issued in corresponding Chinese Patent Application No. 201280006094.2 (7 pages).
English translation of Chinese Office Action dated Apr. 21, 2014, issued in corresponding Chinese Patent Application No. 201280006094.2, (9 pages).
Office Action dated Dec. 1, 2014, issued in Eurasian Patent Application No. 201391314/28, with English Translation (5 pages).
Response to Decision of Rejection dated Nov. 25, 2014, issued in coreesponding Taiwanese Patent Application No. 99132974 with English translation (14 pages).
Office Action dated May 8, 2015, issued in corresponding Taiwanese Patent Application No. 101108422 with English translation (11 pages).

* cited by examiner

PHENYLPYRIDINE DERIVATIVE AND DRUG CONTAINING SAME

TECHNICAL FIELD

The present invention relates to novel phenylpyridine derivatives that have both angiotensin II antagonistic activity and a PPARγ activation effect, and a pharmaceutical agent containing the same.

BACKGROUND ART

In recent years, diseases such as diabetes, hypertension, dyslipidemia and obesity which can be a risk factor for arteriosclerotic diseases have been rapidly increasing due to changes in life style with improvements in living standard, i.e., high calorie and high cholesterol type diet, obesity, lack of exercise, aging, and the like. It is known that, although being a risk factor independent of each other, overlap of the diseases can cause an occurrence of arteriosclerotic diseases at higher frequency or aggravation of the diseases. As such, with the understanding of a condition having a plurality of risk factors for arteriosclerotic diseases as metabolic syndrome, efforts have been made to elucidate the cause of the syndrome and to develop a therapeutic method therefor.

Angiotensin II (herein below, also abbreviated as "AII") is a peptide that is found to be an intrinsic pressor substance produced by renin-angiotensin system (i.e., RA system). It is believed that pharmacological inhibition of angiotensin II activity can lead to treatment or prevention of circulatory diseases such as hypertension. Accordingly, an inhibitor for angiotensin converting enzyme (ACE) which inhibits the enzyme for promoting the conversion of angiotensin I (AI) to angiotensin II has been clinically used as an inhibitory agent for RA system. Furthermore, an orally administrable AII receptor blocker (Angiotensin Receptor Blocker: ARB) has been developed, and losartan, candesartan, telmisartan, valsartan, olmesartan, irbesartan, and the like are already clinically used as a hypotensive agent. It is reported by many clinical or basic studies that, as having not only a hypotensive activity but also other various activities including an anti-inflammatory activity, an endothelial function improving activity, a cardiovascular remodeling inhibiting activity, an oxidation stress inhibiting activity, a proliferation factor inhibiting activity, insulin resistance improving activity, and the like, ARB is useful for cardiovascular diseases, renal diseases, arteriosclerosis, and the like (Non-Patent Documents 1 and 2). Most recently, it is also reported that ARB particularly has a kidney protecting activity which does not depend on a hypotensive activity (Non-Patent Document 3).

Meanwhile, three isoforms, i.e., α, γ and δ have been identified so far for peroxisome proliferator-activated receptors (PPARs) which belong to a nuclear receptor superfamily. Among them, PPARγ is an isoform most abundantly expressed in an adipose tissue and it plays an important role in differentiation of adipocytes or metabolism of glycolipids. Currently, thiazolidinedione derivatives (i.e., TZD) such as pioglitazone or rosiglitazone are clinically used as a therapeutic agent for diabetes having a PPARγ activation effect, and they are known to have an activity of improving insulin resistance, glucose tolerance, lipid metabolism, and the like. Further, it is recently reported that, based on activation of PPARγ, TZD exhibits various activities including a hypotensive activity, an anti-inflammatory activity, an endothelial function improving activity, a proliferation factor inhibiting activity, an activity of interfering RA system, and the like. It is also reported that, according to such multiple activities, TZD shows a kidney protecting activity particularly in diabetic nephropathy without depending on blood sugar control (Non-Patent Documents 4, 5, 6, 7, and 8). Meanwhile, there is also a concern regarding adverse effects of TZD caused by PPARγ activation, such as body fluid accumulation, body weight gain, peripheral edema, and pulmonary edema (Non-Patent Documents 9 and 10).

It has been recently reported that telmisartan has a PPARγ activation effect (Non-Patent Document 11). It has been also reported that the irbesartan has the same activity (Non-Patent Document 12). These compounds have both an RA system inhibiting activity and a PPARγ activation effect, and thus are expected to be used as an integrated agent for prevention and/or treatment of circulatory diseases (e.g., hypertension, heart disease, angina pectoris, cerebral vascular disorder, cerebral circulatory disorder, ischemic peripheral circulatory disorder, kidney disease, and the like) or diabetes-related diseases (e.g., type 2 diabetes mellitus, diabetic complication, insulin resistant syndrome, metabolic syndrome, hyperinsulinemia, and the like) without increasing a risk of body fluid accumulation, body weight gain, peripheral edema, pulmonary edema, or congestive heart failure that are concerned over the use of TZD (Patent Document 1). Among them, for diabetic nephropathy, a synergistic prophylactic and/or therapeutic effect is expected from composite kidney protecting activity that is based on activities of RA system inhibition and PPARγ activation.

As a compound having the activities above, pyrimidine and triazine derivatives (Patent Document 1), imidazopyridine derivatives (Patent Document 2), indole derivatives (Patent Document 3), imidazole derivatives (Patent Document 4), and condensed ring derivatives (Patent Document 5) have been reported. However, there is no description or suggestion regarding the phenylpyridine derivatives of the present invention.

Meanwhile, Patent Document 6 discloses a compound represented by the following formula (A):

[Chemical Formula 1]

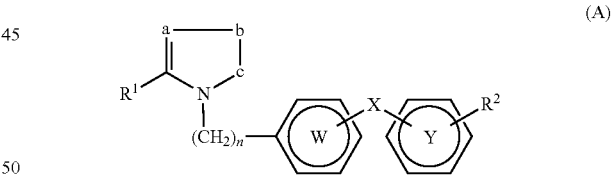

(A)

[in the formula, $R^1$ is an optionally substituted hydrocarbon residue which is optionally bonded through a hetero atom, $R^2$ is an optionally substituted 5 to 7 membered heterocyclic residue having, as a group capable of constituting the ring, a carbonyl group, a thiocarbonyl group, an optionally oxidized sulfur atom or a group convertible into them, X is a direct bond or bonding via a spacer having an atomic length of two or less between the ring Y and the ring W, W and Y are an optionally substituted aromatic hydrocarbon residue optionally containing a hetero atom or an optionally substituted heterocyclic residue; n is an integer of 1 or 2, a and b forming the heterocyclic residue are independently one or two optionally substituted carbon or hetero atoms, c is an optionally substituted carbon or hetero atom, and, in the group of the formula,

[Chemical Formula 2]

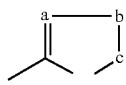

substituent groups on adjacent two atoms forming the ring are optionally bonded to each other to form a 5 to 6 membered ring together with the two atoms forming the ring]. As a preferred W—Y ring system, biphenyl is exemplified. In the Examples, only the biphenyl derivatives are specifically described. The compounds disclosed in Patent Document 6 are different from the compounds of the present invention in terms of the ring bonded to the pyridinyl methyl group. In addition, Patent Document 6 includes no descriptions or suggestions relating to a PPARγ activation effect as a pharmacological activity or treatment of diabetes, obesity, or metabolic syndromes.

PRIOR ART DOCUMENT

Patent Document

Patent Document 1: WO 2008/062905 A
Patent Document 2: WO 2008/084303 A
Patent Document 3: WO 2008/096820 A
Patent Document 4: WO 2008/096829 A
Patent Document 5: WO 2008/143262 A
Patent Document 6: JP 5-271228 A Non-Patent Document Non-Patent Document 1: AMER. J. Hypertension, 18, 720 (2005)
Non-Patent Document 2: Current Hypertension Report, 10, 261 (2008)
Non-Patent Document 3: Diabetes Care, 30, 1581 (2007)
Non-Patent Document 4: Kidney Int., 70, 1223 (2006)
Non-Patent Document 5: Circulation, 108, 2941 (2003)
Non-Patent Document 6: Best Pract. Res. Clin. Endocrinol. Metab., 21 (4), 687 (2007)
Non-Patent Document 7: Diab. Vasc. Dis. Res., 1 (2), 76 (2004)
Non-Patent Document 8: Diab. Vasc. Dis. Res., 2 (2), 61 (2005)
Non-Patent Document 9: J. Clin. Invest., 116 (3), 581 (2006)
Non-Patent Document 10: FASEB J., 20 (8), 1203 (2006)
Non-Patent Document 11: Hypertension, 43, 993 (2004)
Non-Patent Document 12: Circulation, 109, 2054 (2004)

SUMMARY OF THE INVENTION

Problems to be Solved by the Invention

An object of the invention is to provide a novel compound that is useful as a pharmaceutical agent for preventing and/or treating hypertension as a circulatory disease, diabetes as a metabolic disease, and the like, and a pharmaceutical composition using the novel compound.

Means for Solving the Problems

As a result of intensive studies to achieve the purpose described above, the inventors found that the compound represented by the formula (I) below has both an excellent angiotensin II antagonistic activity and an excellent PPARγ activation effect, and therefore completed the invention.

Specifically, the present invention relates to the following inventions.

[1] A compound represented by the formula (I) below or a salt thereof, or a solvate thereof:

[Chemical Formula 3]

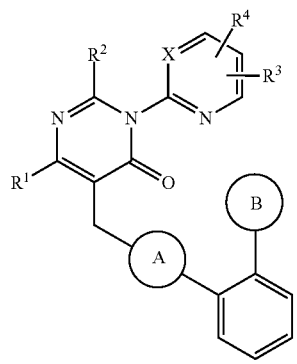

(I)

[in the formula, ring A represents the following formula (II) or formula (III):

[Chemical Formula 4]

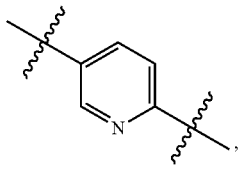

(II)

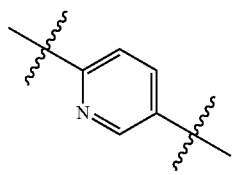

(III)

ring B represents the following formula (IV) or formula (V):

[Chemical Formula 5]

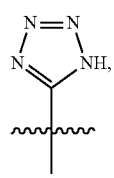

(IV)

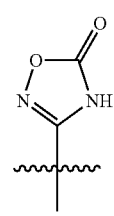

(V)

X represents C—R⁵ or a nitrogen atom,
R¹ represents a $C_{1-6}$ alkyl group,
R² represents a $C_{1-6}$ alkyl group or a $C_{3-8}$ cycloalkyl group, and
R³, R⁴, and R⁵ each independently represent a hydrogen atom, a halogen atom, a $C_{1-6}$ alkyl group, a halo $C_{1-6}$ alkyl group, or a $C_{1-6}$ alkoxy group which may have a substituent group, and the broken line in the formula indicates the binding site for a neighboring group].

[2] The compound described in the above [1] or a salt thereof, or a solvate thereof, in which the ring A in the formula (I) is the formula (II) described above, and X is a nitrogen atom.

[3] The compound described in the above [1] or [2] or a salt thereof, or a solvate thereof, in which the ring B in the formula (I) is the formula (V) described above.

[4] The compound described in any one of the above [1] to [3] or a salt thereof, or a solvate thereof, in which R² in the formula (I) is a branched $C_{1-6}$ alkyl group or a $C_3$—cycloalkyl group.

[5] The compound described in any one of the above [1] to [4] or a salt thereof, or a solvate thereof, in which R¹ in the formula (I) is a $C_{1-3}$ alkyl group or a $C_{5-6}$ alkyl group.

[6] The compound described in any one of the above [1] to [5] or a salt thereof, or a solvate thereof, in which the ring A in the formula (I) is the formula (II) described above and the ring B is the formula (V) described above.

[7] The compound described in any one of the above [1] to [6] or a salt thereof, or a solvate thereof, in which X in the formula (I) is a nitrogen atom and R³ and R⁴ are each independently a hydrogen atom, a halogen atom, a $C_{1-6}$ alkyl group, a halo $C_{1-6}$ alkyl group, or a $C_{1-6}$ alkoxy group.

[8] The compound described in the above [7] or a salt thereof, or a solvate thereof, in which R³ and R⁴ in the formula (I) are each independently a hydrogen atom or a $C_{1-6}$ alkoxy group.

[9] The compound described in the above [1] or a salt thereof, or a solvate thereof, in which the compound represented by the formula (I) is a compound selected from a group consisting of:

5-{{6-[2-(1H-tetrazol-5-yl)phenyl]pyridin-3-yl}methyl}-6-butyl-3-(5-methoxypyrimidin-2-yl)-2-methylpyrimidin-4(3H)-one, 5-{{6-[2-(1H-tetrazol-5-yl)phenyl]pyridin-3-yl}methyl}-6-butyl-3-(5-ethoxypyrimidin-2-yl)-2-methylpyrimidin-4(3H)-one, 5-{{6-[2-(1H-tetrazol-5-yl)phenyl]pyridin-3-yl}methyl}-6-butyl-2-ethyl-3-(5-methoxypyrimidin-2-yl)pyrimidin-4(3H)-one, 5-{{6-[2-(1H-tetrazol-5-yl)phenyl]pyridin-3-yl}methyl}-6-butyl-3-(5-ethoxypyrimidin-2-yl)-2-ethylpyrimidin-4(3H)-one, 5-{{6-[2-(1H-tetrazol-5-yl)phenyl]pyridin-3-yl}methyl}-6-butyl-2-isopropyl-3-(5-methoxypyrimidin-2-yl)pyrimidin-4(3H)-one, 5-{{6-[2-(1H-tetrazol-5-yl)phenyl]pyridin-3-yl}methyl}-6-butyl-3-(5-ethoxypyrimidin-2-yl)-2-isopropylpyrimidin-4(3H)-one, 5-{{6-[2-(1H-tetrazol-5-yl)phenyl]pyridin-3-yl}methyl}-6-butyl-2-cyclopropyl-3-(5-methoxypyrimidin-2-yl)pyrimidin-4(3H)-one, 5-{{6-[2-(1H-tetrazol-5-yl)phenyl]pyridin-3-yl}methyl}-6-butyl-2-cyclobutyl-3-(5-methoxypyrimidin-2-yl)pyrimidin-4(3H)-one, 5-{{6-[2-(1H-tetrazol-5-yl)phenyl]pyridin-3-yl}methyl}-6-butyl-2-cyclobutyl-3-(5-ethoxypyrimidin-2-yl)pyrimidin-4(3H)-one, 5-{{6-[2-(1H-tetrazol-5-yl)phenyl]pyridin-3-yl}methyl}-6-butyl-2-cyclopentyl-3-(5-ethoxypyrimidin-2-yl)pyrimidin-4(3H)-one, 5-{{6-[2-(1H-tetrazol-5-yl)phenyl]pyridin-3-yl}methyl}-6-butyl-2-cyclohexyl-3-(5-ethoxypyrimidin-2-yl)pyrimidin-4(3H)-one, 5-{{6-[2-(1H-tetrazol-5-yl)phenyl]pyridin-3-yl}methyl}-6-butyl-2-methyl-3-{5-[2-(methylthio)ethoxy]pyrimidin-2-yl}pyrimidin-4(3H)-one, 5-{{6-[2-(1H-tetrazol-5-yl)phenyl]pyridin-3-yl}methyl}-6-butyl-2-methyl-3-{5-[2-(methylsulfonyl)ethoxy]pyrimidin-2-yl}pyrimidin-4(3H)-one, 3-{2-{5-{[4-butyl-2-methyl-6-oxo-1-(pyridin-2-yl)-1,6-dihydropyrimidin-5-yl]methyl}pyridin-2-yl}phenyl}-1,2,4-oxadiazol-5(4H)-one, 3-{2-{5-{[4-butyl-2-methyl-1-(4-methylpyridin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-1-(5-methoxypyrimidin-2-yl)-2-methyl-6-oxo-1,6-dihydropyrimidin-5-yl]methyl}pyridin-2-yl}phenyl}-1,2,4-oxadiazol-5(4H)-one, 3-{2-{5-{[4-butyl-1-(5-ethoxypyrimidin-2-yl)-2-methyl-6-oxo-1,6-dihydropyrimidin-5-yl]methyl}pyridin-2-yl}phenyl}-1,2,4-oxadiazol-5(4H)-one, 3-{2-{5-{[4-butyl-2-ethyl-1-(5-methoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-1-(5-ethoxypyrimidin-2-yl)-2-ethyl-6-oxo-1,6-dihydropyrimidin-5-yl]methyl}pyridin-2-yl}phenyl}-1,2,4-oxadiazol-5(4H)-one, 3-{2-{5-{[4-butyl-2-isopropyl-1-(5-methoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-1-(5-ethoxypyrimidin-2-yl)-2-isopropyl-6-oxo-1,6-dihydropyrimidin-5-yl]methyl}pyridin-2-yl}phenyl}-1,2,4-oxadiazol-5(4H)-one, 3-{2-{5-{[4-butyl-2-cyclopropyl-1-(5-methoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclopropyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclobutyl-1-(5-methoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclobutyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclopentyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclohexyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{{4-butyl-2-methyl-1-{5-[2-(methylthio)ethoxy]pyrimidin-2-yl}-6-oxo-1,6-dihydropyrimidin-5-yl}methyl}pyridin-2-yl}phenyl}-1,2,4-oxadiazol-5(4H)-one, 3-{2-{5-{{4-butyl-2-methyl-1-{5-[2-(methylsulfonyl)ethoxy]pyrimidin-2-yl}-6-oxo-1,6-dihydropyrimidin-5-yl}methyl}pyridin-2-yl}phenyl}-1,2,4-oxadiazol-5(4H)-one, 5-{{5-[2-(1H-tetrazol-5-yl)phenyl]pyridin-2-yl}methyl}-6-butyl-2-methyl-3-(pyridin-2-yl)pyrimidin-4(3H)-one, 5-{{5-[2-(1H-tetrazol-5-yl)phenyl]pyridin-2-yl}methyl}-6-butyl-3-(5-methoxypyridin-2-yl)-2-methylpyrimidin-4(3H)-one, 5-{{5-[2-(1H-tetrazol-5-yl)phenyl]pyridin-2-yl}methyl}-6-butyl-3-[3-chloro-5-(trifluoromethyl)pyridin-2-yl]-2-methylpyrimidin-4(3H)-one,
5-{{5-[2-(1H-tetrazol-5-yl)phenyl]pyridin-2-yl}methyl}-6-butyl-3-(5-methoxypyrimidin-2-yl)-2-methylpyrimidin-4(3H)-one,
5-{{5-[2-(1H-tetrazol-5-yl)phenyl]pyridin-2-yl}methyl}-6-butyl-3-(5-ethoxypyrimidin-2-yl)-2-methylpyrimidin-4(3H)-one,
5-{{5-[2-(1H-tetrazol-5-yl)phenyl]pyridin-2-yl}methyl}-6-butyl-3-(4,6-dimethoxypyrimidin-2-yl)-2-methylpyrimidin-4(3H)-one,
3-{2-{6-{[4-butyl-1-(5-methoxypyridin-2-yl)-2-methyl-6-oxo-1,6-dihydropyrimidin-5-yl]methyl}pyridin-3-yl}phenyl}-1,2,4-oxadiazol-5(4H)-one,
3-{2-{6-{[4-butyl-1-(5-methoxypyrimidin-2-yl)-2-methyl-6-oxo-1,6-dihydropyrimidin-5-yl]methyl}pyridin-3-yl}phenyl}-1,2,4-oxadiazol-5(4H)-one,
3-{2-{6-{[4-butyl-1-(5-ethoxypyrimidin-2-yl)-2-methyl-6-oxo-1,6-dihydropyrimidin-5-yl]methyl}pyridin-3-yl}phenyl}-1,2,4-oxadiazol-5(4H)-one,
3-{2-{6-{[4-butyl-1-(4,6-dimethoxypyrimidin-2-yl)-2-methyl-6-oxo-1,6-dihydropyrimidin-5-yl]methyl}pyridin-3-yl}phenyl}-1,2,4-oxadiazol-5(4H)-one,
3-{2-{5-{[1-(5-ethoxypyrimidin-2-yl)-2-isopropyl-6-oxo-4-propyl-1,6-dihydropyrimidin-5-yl]methyl}pyridin-2-yl}phenyl}-1,2,4-oxadiazol-5(4H)-one,
3-{2-{5-{[2-cyclopropyl-1-(5-ethoxypyrimidin-2-yl)-6-oxo-4-propyl-1,6-dihydropyrimidin-5-yl]methyl}pyridin-2-yl}phenyl}-1,2,4-oxadiazol-5(4H)-one,
3-{2-{5-{[1-(5-ethoxypyrimidin-2-yl)-2-isopropyl-6-oxo-4-pentyl-1,6-dihydropyrimidin-5-yl]methyl}pyridin-2-yl}phenyl}1,2,4-oxadiazol-5(4H)-one,
3-{2-{5-{[2-cyclopropyl-1-(5-ethoxypyrimidin-2-yl)-6-oxo-4-pentyl-1,6-dihydropyrimidin-5-yl]methyl}pyridin-2-yl}phenyl}-1,2,4-oxadiazol-5(4H)-one,
3-{2-{5-{[1-(5-ethoxypyrimidin-2-yl)-4-ethyl-2-isopropyl-6-oxo-1,6-dihydropyrimidin-5-yl]methyl}pyridin-2-yl}phenyl}-1,2,4-oxadiazol-5(4H)-one, and
3-{2-{5-{[2-cyclopropyl-1-(5-ethoxypyrimidin-2-yl)-4-ethyl-6-oxo-1,6-dihydropyrimidin-5-yl]methyl}pyridin-2-yl}phenyl}-1,2,4-oxadiazol-5(4H)-one.

[10] The compound described in the above [1] or a salt thereof, or a solvate thereof, in which the compound represented by the formula (I) is a compound selected from a group consisting of:
5-{{6-[2-(1H-tetrazol-5-yl)phenyl]pyridin-3-yl}methyl}-6-butyl-2-isopropyl-3-(5-methoxypyrimidin-2-yl)pyrimidin-4(3H)-one,
5-{{6-[2-(1H-tetrazol-5-yl)phenyl]pyridin-3-yl}methyl}-6-butyl-3-(5-ethoxypyrimidin-2-yl)-2-isopropylpyrimidin-4(3H)-one,
5-{{6-[2-(1H-tetrazol-5-yl)phenyl]pyridin-3-yl}methyl}-6-butyl-2-cyclopropyl-3-(5-methoxypyrimidin-2-yl)pyrimidin-4(3H)-one,
5-{{6-[2-(1H-tetrazol-5-yl)phenyl]pyridin-3-yl}methyl}-6-butyl-2-cyclobutyl-3-(5-methoxypyrimidin-2-yl)pyrimidin-4(3H)-one,
5-{{6-[2-(1H-tetrazol-5-yl)phenyl]pyridin-3-yl}methyl}-6-butyl-2-cyclobutyl-3-(5-ethoxypyrimidin-2-yl)pyrimidin-4(3H)-one,
5-{{6-[2-(1H-tetrazol-5-yl)phenyl]pyridin-3-yl}methyl}-6-butyl-2-cyclopentyl-3-(5-ethoxypyrimidin-2-yl)pyrimidin-4(3H)-one,
5-{{6-[2-(1H-tetrazol-5-yl)phenyl]pyridin-3-yl}methyl}-6-butyl-2-cyclohexyl-3-(5-ethoxypyrimidin-2-yl)pyrimidin-4(3H)-one,
3-{2-{5-{[4-butyl-2-isopropyl-1-(5-methoxypyrimidin-2-yl)-6-oxo-1,6-dihydropyrimidin-5-yl]methyl}pyridin-2-yl}phenyl}-1,2,4-oxadiazol-5(4H)-one,
3-{2-{5-{[4-butyl-1-(5-ethoxypyrimidin-2-yl)-2-isopropyl-6-oxo-1,6-dihydropyrimidin-5-yl]methyl}pyridin-2-yl}phenyl}-1,2,4-oxadiazol-5(4H)-one,
3-{2-{5-{[4-butyl-2-cyclopropyl-1-(5-methoxypyrimidin-2-yl)-6-oxo-1,6-dihydropyrimidin-5-yl]methyl}pyridin-2-yl}phenyl}-1,2,4-oxadiazol-5(4H)-one,
3-{2-{5-{[4-butyl-2-cyclopropyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one,
3-{2-{5-{[4-butyl-2-cyclobutyl-1-(5-methoxypyrimidin-2-yl)-6-oxo-1,6-dihydropyrimidin-5-yl]methyl}pyridin-2-yl}phenyl}-1,2,4-oxadiazol-5(4H)-one,
3-{2-{5-{[4-butyl-2-cyclobutyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one,
3-{2-{5-{[4-butyl-2-cyclopentyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one,
3-{2-{5-{[4-butyl-2-cyclohexyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one,
3-{2-{5-{[1-(5-ethoxypyrimidin-2-yl)-2-isopropyl-6-oxo-4-propyl-1,6-dihydropyrimidin-5-yl]methyl}pyridin-2-yl}phenyl}-1,2,4-oxadiazol-5(4H)-one,
3-{2-{5-{[2-cyclopropyl-1-(5-ethoxypyrimidin-2-yl)-6-oxo-4-propyl-1,6-dihydropyrimidin-5-yl]methyl}pyridin-2-yl}phenyl}-1,2,4-oxadiazol-5(4H)-one,
3-{2-{5-{[1-(5-ethoxypyrimidin-2-yl)-2-isopropyl-6-oxo-4-pentyl-1,6-dihydropyrimidin-5-yl]methyl}pyridin-2-yl}phenyl}-1,2,4-oxadiazol-5(4H)-one,
3-{2-{5-{[2-cyclopropyl-1-(5-ethoxypyrimidin-2-yl)-6-oxo-4-pentyl-1,6-dihydropyrimidin-5-yl]methyl}pyridin-2-yl}phenyl}-1,2,4-oxadiazol-5(4H)-one,
3-{2-{5-{[1-(5-ethoxypyrimidin-2-yl)-4-ethyl-2-isopropyl-6-oxo-1,6-dihydropyrimidin-5-yl]methyl}pyridin-2-yl}phenyl}-1,2,4-oxadiazol-5(4H)-one, and
3-{2-{5-{[2-cyclopropyl-1-(5-ethoxypyrimidin-2-yl)-4-ethyl-6-oxo-1,6-dihydropyrimidin-5-yl]methyl}pyridin-2-yl}phenyl}-1,2,4-oxadiazol-5(4H)-one.

[11] The compound described in the above [1] or a salt thereof, or a solvate thereof, in which the compound represented by the formula (I) is a compound selected from a group consisting of:
3-{2-{5-{[1-(5-ethoxypyrimidin-2-yl)-2-isopropyl-6-oxo-4-propyl-1,6-dihydropyrimidin-5-yl]methyl}pyridin-2-yl}phenyl}-1,2,4-oxadiazol-5(4H)-one,
3-{2-{5-{[2-cyclopropyl-1-(5-ethoxypyrimidin-2-yl)-6-oxo-4-propyl-1,6-dihydropyrimidin-5-yl]methyl}pyridin-2-yl}phenyl}-1,2,4-oxadiazol-5(4H)-one,
3-{2-{5-{[1-(5-ethoxypyrimidin-2-yl)-2-isopropyl-6-oxo-4-pentyl-1,6-dihydropyrimidin-5-yl]methyl}pyridin-2-yl}phenyl}-1,2,4-oxadiazol-5(4H)-one,
3-{2-{5-{[2-cyclopropyl-1-(5-ethoxypyrimidin-2-yl)-6-oxo-4-pentyl-1,6-dihydropyrimidin-5-yl]methyl}pyridin-2-yl}phenyl}-1,2,4-oxadiazol-5(4H)-one,
3-{2-{5-{[1-(5-ethoxypyrimidin-2-yl)-4-ethyl-2-isopropyl-6-oxo-1,6-dihydropyrimidin-5-yl]methyl}pyridin-2-yl}phenyl}-1,2,4-oxadiazol-5(4H)-one, and
3-{2-{5-{[2-cyclopropyl-1-(5-ethoxypyrimidin-2-yl)-4-ethyl-6-oxo-1,6-dihydropyrimidin-5-yl]methyl}pyridin-2-yl}phenyl}-1,2,4-oxadiazol-5(4H)-one.

Meanwhile, the alkyl group such as butyl in the nomenclature of the above-mentioned compounds represents a straight (normal) chain unless particularly described.

[12] A pharmaceutical composition containing the compound described in any one of the above [1] to [11] or a salt thereof, or a solvate thereof, and a pharmaceutically acceptable carrier.

[13] The pharmaceutical composition described in the above [12], in which the ring A in the formula (I) is the formula (II) described above and X is a nitrogen atom.

[14] The pharmaceutical composition described in the above [12] or [1,3], in which the ring B in the formula (I) is the formula (V) described above.

[15] The pharmaceutical composition described in any one of the above [12] to [14], in which $R^2$ in the formula (I) is a branched $C_{3-6}$ alkyl group or a $C_{3-8}$ cycloalkyl group.

[16] The pharmaceutical composition described in any one of the above [12] to [15], in which $R^1$ in the formula (I) is a $C_{1-3}$ alkyl group or a $C_{5-6}$ alkyl group.

[17] The pharmaceutical composition described in any one of the above [12] to [16], in which the ring A in the formula (I) is the formula (II) described above and the ring B is the formula (V) described above.

[18] The pharmaceutical composition described in any one of the above [12] to [17], in which X in the formula (I) is a nitrogen atom and $R^3$ and $R^4$ are each independently a hydrogen atom, a halogen atom, a $C_{1-6}$ alkyl group, a halo $C_{1-6}$ alkyl group, or a $C_{1-6}$ alkoxy group.

[19] The pharmaceutical composition described in the above [18], in which $R^3$ and $R^4$ in the formula (I) are each independently a hydrogen atom or a $C_{1-6}$ alkoxy group.

[20] The pharmaceutical composition described in any one of the above [12] to [19], having both angiotensin II receptor antagonistic activity and a PPARγ activation effect.

[21] The pharmaceutical composition described in any one of the above [12] to [20], which is an agent for preventing and/or treating a circulatory disease.

[22] The pharmaceutical composition described in the above [21], in which the circulatory disease is hypertension, heart disease, angina pectoris, cerebral vascular disorder, cerebral circulatory disorder, ischemic peripheral circulatory disorder, kidney disease, or arteriosclerosis.

[23] The pharmaceutical composition described in any one of the above [12] to [20], which is an agent for preventing and/or treating a metabolic disease.

[24] The pharmaceutical composition described in the above [23], in which the metabolic disease is type 2 diabetes mellitus, diabetic complication (diabetic retinopathy, diabetic neuropathy, or diabetic nephropathy), insulin resistant syndrome, metabolic syndrome, or hyperinsulinemia.

[25] A method of preventing and/or treating a circulatory disease, the method including administering an effective amount of the compound described in any one of the above [1] to [11] or a salt thereof, or a solvate thereof to a patient who is in need of the treatment.

[26] The method described in the above [25], in which the circulatory disease is hypertension, heart disease, angina pectoris, cerebral vascular disorder, cerebral circulatory disorder, ischemic peripheral circulatory disorder, kidney disease, or arteriosclerosis.

[27] A method of preventing and/or treating a metabolic disease, the method including administering an effective amount of the compound described in any one of the above [1] to [11] or a salt thereof, or a solvate thereof to a patient who is in need of the treatment.

[28] The method described in the above [27], in which the metabolic disease is type 2 diabetes mellitus, diabetic complication (diabetic retinopathy, diabetic neuropathy, or diabetic nephropathy), insulin resistant syndrome, metabolic syndrome, or hyperinsulinemia.

[29] A method of preventing and/or treating a circulatory disease and a metabolic disease, the method including administering an effective amount of the compound described in any one of the above [1] to [11] or a salt thereof, or a solvate thereof to a patient who is in need of the treatment.

[30] The method described in the above [29], in which the circulatory disease is hypertension, heart disease, angina pectoris, cerebral vascular disorder, cerebral circulatory disorder, ischemic peripheral circulatory disorder, kidney disease, or arteriosclerosis and the metabolic disease is type 2 diabetes mellitus, diabetic complication (diabetic retinopathy, diabetic neuropathy, or diabetic nephropathy), insulin resistant syndrome, metabolic syndrome, or hyperinsulinemia.

[31] Use of the compound described in any one of the above [1] to [11] or a salt thereof, or a solvate thereof for producing a preparation for preventing and/or treating a circulatory disease.

[32] The use described in the above [31], in which the circulatory disease is hypertension, heart disease, angina pectoris, cerebral vascular disorder, cerebral circulatory disorder, ischemic peripheral circulatory disorder, kidney disease, or arteriosclerosis.

[33] Use of the compound described in any one of the above [1] to [11] or a salt thereof, or a solvate thereof for producing a preparation for preventing and/or treating a metabolic disease.

[34] The use described in the above [33], in which the metabolic disease is type 2 diabetes mellitus, diabetic complication (diabetic retinopathy, diabetic neuropathy, or diabetic nephropathy), insulin resistant syndrome, metabolic syndrome, or hyperinsulinemia.

[35] The compound described in any one the above [1] to [11] or a salt thereof, or a solvate thereof to be used for a pharmaceutical composition for preventing and/or treating a circulatory disease.

[36] The compound described in the above [35] or a salt thereof, or a solvate thereof, in which the circulatory disease is hypertension, heart disease, angina pectoris, cerebral vascular disorder, cerebral circulatory disorder, ischemic peripheral circulatory disorder, kidney disease, or arteriosclerosis.

[37] The compound described in the above [35] or [36] or a salt thereof, or a solvate thereof, in which the effective component of a pharmaceutical composition is a compound or a salt thereof, or a solvate thereof having both an angiotensin II receptor antagonistic activity and a PPARγ activation effect.

[38] The compound described in any one of the above [1] to [11] or a salt thereof, or a solvate thereof to be used for a pharmaceutical composition for preventing and/or treating a metabolic disease.

[39] The compound described in the above [38] or a salt thereof, or a solvate thereof, in which the metabolic disease is type 2 diabetes mellitus, diabetic complication (diabetic retinopathy, diabetic neuropathy, or diabetic nephropathy), insulin resistant syndrome, metabolic syndrome, or hyperinsulinemia.

[40] The compound described in the above [38] or [39] or a salt thereof, or a solvate thereof, in which the effective component of a pharmaceutical composition is a compound or a salt thereof, or a solvate thereof having both an angiotensin II receptor antagonistic activity and a PPARγ activation effect.

[41] The compound described in any one of the above [1] to [11] or a salt thereof, or a solvate thereof to be used for a pharmaceutical composition for preventing and/or treating a circulatory disease or a metabolic disease.

[42] The compound described in the above [41] or a salt thereof, or a solvate thereof, in which the circulatory disease is hypertension, heart disease, angina pectoris, cerebral vascular disorder, cerebral circulatory disorder, ischemic peripheral circulatory disorder, kidney disease, or arteriosclerosis and the metabolic disease is type 2 diabetes mellitus, diabetic complication (diabetic retinopathy, diabetic neuropathy, or diabetic nephropathy), insulin resistant syndrome, metabolic syndrome, or hyperinsulinemia.

Effects of the Invention

The phenylpyridine derivative represented by the formula (I) of the invention or a salt thereof, or a solvate thereof exhibits a potent antagonistic activity for an angiotensin II receptor, and can be appropriately used as an effective component of an agent for preventing and/or treating a disease related with angiotensin II, for example a circulatory disease such as hypertension, heart disease, angina pectoris, cerebral vascular disorder, cerebral circulatory disorder, ischemic peripheral circulatory disorder, kidney disease, and arteriosclerosis.

Further, the phenylpyridine derivative represented by the formula (I) of the invention or a salt thereof, or a solvate thereof exhibits a PPARγ activation effect and can be appropriately used as an effective component of an agent for preventing and/or treating a disease related with PPARγ, for example a metabolic disease such as arteriosclerosis, type 2 diabetes mellitus, diabetic complication (diabetic retinopathy, diabetic neuropathy, or diabetic nephropathy), insulin resistance syndrome, syndrome X, metabolic syndrome, and hyperinsulinemia.

Still further, the phenylpyridine derivative represented by the formula (I) of the invention or a salt thereof, or a solvate thereof has both an antagonistic activity for an angiotensin II receptor and a PPARγ activation effect and can be appropriately used as an effective component of an agent for preventing and/or treating a disease related with both angiotensin II and PPARγ, for example, arteriosclerosis, diabetic nephropathy, insulin resistance syndrome, syndrome X, and metabolic syndrome.

MODES FOR CARRYING OUT THE INVENTION

The "halogen atom" as used herein includes a fluorine atom, a chlorine atom, a bromine atom, an iodine atom, and the like.

The "$C_{1-6}$ alkyl group" and "$C_{1-6}$ alkyl" as used herein mean a linear or a branched hydrocarbon group having 1 to 6 carbon atoms, preferably a saturated linear or branched hydrocarbon group having 1 to 6 carbon atoms, and examples thereof include a methyl group, an ethyl group, an n-propyl group, an isopropyl group, an n-butyl group, an isobutyl group, a t-butyl group, an n-pentyl group, a 2-methylbutyl group, a 2,2-dimethylpropyl group, and an n-hexyl group. Further, the "branched $C_{3-6}$ alkyl group" and "branched $C_{3-6}$ alkyl" as used herein mean a branched hydrocarbon group having 3 to 6 carbon atoms, preferably a saturated branched hydrocarbon group having 3 to 6 carbon atoms, and examples thereof include an isopropyl group, an isobutyl group, a 2-methylbutyl group, a 2-methylpentyl group, and a 2-ethylbutyl group.

The "$C_{3-8}$ cycloalkyl group" and "$C_{3-8}$ cycloalkyl" as used herein mean a saturated or unsaturated and monocyclic, polycyclic, or fused-cyclic cycloalkyl group having 3 to 8 carbon atoms, and preferably 3 to 6 carbon atoms, and examples of the cycloalkyl group include a cyclopropyl group, a cyclobutyl group, a cyclopentyl group, a cyclohexyl group, a cycloheptyl group, and a cyclooctyl group.

The "halo $C_{1-6}$ alkyl group" and "halo $C_{1-6}$ alkyl" as used herein mean a linear or a branched alkyl group having 1 to 6 carbon atoms which is substituted with one or more to maximally substitutable number of halogen atoms, and examples thereof include a fluoromethyl group, a difluoromethyl group, a trifluoromethyl group, a 2,2,2-trifluoroethyl group, a 1,1,2,2,2-pentafluoroethyl group, and a 3,3,3-trifluoropropyl group.

The "$C_{1-6}$ alkoxy group" as used herein means a linear or a branched alkoxy group having 1 to 6 carbon atoms, and examples thereof include a methoxy group, an ethoxy group, a propoxy group, an isopropoxy group, a butoxy group, an isobutoxy group, a sec-butoxy group, a tert-butoxy group, a pentoxy group, an isopentoxy group, a neopentoxy group, a hexyloxy group, and an isohexyloxy group.

As used herein, the "substituent group" of the "$C_{1-5}$ alkoxy group which may have a substituent group" may be the same or different from each other, and the alkoxy group may be substituted with one or more to maximally substitutable number of substituent groups. Examples of the "substituent group" include a phenyl group, a hydroxyl group, a $C_{1-6}$ alkoxy group, a $C_{1-6}$ alkylthio group, a $C_{1-6}$ alkylsulfonyl group, an oxazolyl group (the oxazolyl group may be substituted with a $C_{1-6}$ alkyl group, a $C_{6-10}$ aryl group, or a 5 to 10-membered heteroaryl group which may be substituted with a halogen atom), a pyridyl group (the pyridyl group may be substituted with a $C_{1-6}$ alkyl group), a $C_{1-6}$ alkoxycarbonyl group, a carboxyl group, a carbamoyl group, a mono $C_{1-6}$ alkylcarbamoyl group, a di $C_{1-6}$ alkylcarbamoyl group, a $C_{1-6}$ alkanoylamino group, a $C_{1-6}$ alkylsulfonylamino group, a halo $C_{1-6}$ alkylsulfonylamino group, an amide group, and a sulfonamide group. Preferred examples of the substituent group include a $C_{1-6}$ alkylthio group, a $C_{1-6}$ alkylsulfonyl group, a carboxyl group, a carbamoyl group, a mono $C_{1-6}$ alkylcarbamoyl group, and a di $C_{1-6}$ alkylcarbamoyl group. Still more preferred examples of the substituent group include a $C_{1-6}$ alkylthio group and a $C_{1-6}$ alkylsulfonyl group.

Preferred modes of the invention include those described below.

In the formula (I), the $C_{1-6}$ alkyl group as $R^1$ is preferably a $C_{1-6}$ alkyl group except butyl group, that is, a $C_{1-3}$ alkyl group or a $C_{5-6}$ alkyl group, and examples thereof include an ethyl group, an n-propyl group, and an n-pentyl group.

In the formula (I), the $C_{1-6}$ alkyl group as $R^2$ is preferably a $C_{1-4}$ alkyl group, and examples thereof include a methyl group, an ethyl group, and an isopropyl group. An isopropyl group is particularly preferable. Preferred examples of the $C_{1-6}$ alkyl group as $R^2$ include a branched $C_{3-6}$ alkyl group. An isopropyl group is particularly preferable.

In the formula (I), preferred examples of the $C_{3-8}$ cycloalkyl group as $R^2$ include $C_{3-6}$ cycloalkyl, for example, a cyclopropyl group, a cyclobutyl group, a cyclopentyl group, and a cyclohexyl group. A cyclopropyl group is particularly preferable.

In the formula (I), preferred examples of the $C_{1-6}$ alkyl group as $R^3$ and $R^4$ include a $C_{1-4}$ alkyl group, for example, a methyl group and an ethyl group.

In the formula (I), preferred examples of the halo $C_{1-6}$ alkyl group as $R^1$ and $R^4$ include a halo $C_{1-4}$ alkyl group, for example, a difluoromethyl group, a trifluoromethyl group, and a 2,2,2-trifluoroethyl group. A trifluoromethyl group is more preferable.

In the formula (I), preferred examples of the "$C_{1-6}$ alkoxy group" of the $C_{1-6}$ alkoxy group which may have a substituent group as $R^3$ and $R^4$ include a $C_{1-4}$ alkoxy group, for example, a methoxy group, an ethoxy group, a propoxy group, an isopropoxy group, and an n-butoxy group. An ethoxy group is particularly preferable. Preferred examples of the "substituent group" include a phenyl group, a hydroxyl group, a $C_{1-6}$ alkylthio group (for example, a methylthio group), and a $C_{1-6}$ alkylsulfonyl group (for example, a methylsulfonyl group).

More preferred examples of the compound represented by the formula (I) include a compound selected from a group consisting of the following compounds:

5-{{6-[2-(1H-tetrazol-5-yl)phenyl]pyridin-3-yl}methyl}-6-butyl-3-(5-methoxypyrimidin-2-yl)-2-methylpyrimidin-4(3H)-one, 5-{{6-[2-(1H-tetrazol-5-yl)phenyl]pyridin-3-yl}methyl}-6-butyl-3-(5-ethoxypyrimidin-2-yl)-2-methylpyrimidin-4(3H)-one, 5-{{6-[2-(1H-tetrazol-5-yl)phenyl]pyridin-3-yl}methyl}-6-butyl-2-ethyl-3-(5-methoxypyrimidin-2-yl)pyrimidin-4(3H)-one, 5-{{6-[2-(1H-tetrazol-5-yl)phenyl]pyridin-3-yl}methyl}-6-butyl-3-(5-ethoxypyrimidin-2-yl)-2-ethylpyrimidin-4(3H)-one, 5-{{6-[2-(1H-tetrazol-5-yl)phenyl]pyridin-3-yl}methyl}-6-butyl-2-isopropyl-3-(5-methoxypyrimidin-2-yl)pyrimidin-4(3H)-one, 5-{{6-[2-(1H-tetrazol-5-yl)phenyl]pyridin-3-yl}methyl}-6-butyl-3-(5-ethoxypyrimidin-2-yl)-2-isopropylpyrimidin-4(3H)-one, 5-{{6-[2-(1H-tetrazol-5-yl)phenyl]pyridin-3-yl}methyl}-6-butyl-2-cyclopropyl-3-(5-methoxypyrimidin-2-yl)pyrimidin-4(3H)-one, 5-{{6-[2-(1H-tetrazol-5-yl)phenyl]pyridin-3-yl}methyl}-6-butyl-2-cyclobutyl-3-(5-methoxypyrimidin-2-yl)pyrimidin-4(3H)-one, 5-{{6-[2-(1H-tetrazol-5-yl)phenyl]pyridin-3-yl}methyl}-6-butyl-2-cyclobutyl-3-(5-ethoxypyrimidin-2-yl)pyrimidin-4(3H)-one, 5-{{6-[2-(1H-tetrazol-5-yl)phenyl]pyridin-3-yl}methyl}-6-butyl-2-cyclopentyl-3-(5-ethoxypyrimidin-2-yl)pyrimidin-4(3H)-one, 5-{{6-[2-(1H-tetrazol-5-yl)phenyl]pyridin-3-yl}methyl}-6-butyl-2-cyclohexyl-3-(5-ethoxypyrimidin-2-yl)pyrimidin-4(3H)-one, 5-{{6-[2-(1H-tetrazol-5-yl)phenyl]pyridin-3-yl}methyl}-6-butyl-2-methyl-3-{5-[2-(methylthio)ethoxy]pyrimidin-2-yl}pyrimidin-4(3H)-one, 5-{{6-[2-(1H-tetrazol-5-yl)phenyl]pyridin-3-yl}methyl}-6-butyl-2-methyl-3-{5-[2-(methylsulfonyl)ethoxy]pyrimidin-2-yl}pyrimidin-4(3H)-one, 3-{2-{5-{[4-butyl-2-methyl-6-oxo-1-(pyridin-2-yl)-1,6-dihydropyrimidin-5-yl]methyl}pyridin-2-yl}phenyl}-1,2,4-oxadiazol-5(4H)-one, 3-{2-{5-{[4-butyl-2-methyl-1-(4-methylpyridin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-1-(5-methoxypyrimidin-2-yl)-2-methyl-6-oxo-1,6-dihydropyrimidin-5-yl]methyl}pyridin-2-yl}phenyl}-1,2,4-oxadiazol-5(4H)-one, 3-{2-{5-{[4-butyl-1-(5-ethoxypyrimidin-2-yl)-2-methyl-6-oxo-1,6-dihydropyrimidin-5-yl]methyl}pyridin-2-yl}phenyl}-1,2,4-oxadiazol-5(4H)-one, 3-{2-{5-{[4-butyl-2-ethyl-1-(5-methoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-1-(5-ethoxypyrimidin-2-yl)-2-ethyl-6-oxo-1,6-dihydropyrimidin-5-yl]methyl}pyridin-2-yl}phenyl}-1,2,4-oxadiazol-5(4H)-one, 3-{2-{5-{[4-butyl-2-isopropyl-1-(5-methoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-1-(5-ethoxypyrimidin-2-yl)-2-isopropyl-6-oxo-1,6-dihydropyrimidin-5-yl]methyl}pyridin-2-yl}phenyl}-1,2,4-oxadiazol-5(4H)-one, 3-{2-{5-{[4-butyl-2-cyclopropyl-1-(5-methoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclopropyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclobutyl-1-(5-methoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclobutyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclopentyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclohexyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{{4-butyl-2-methyl-1-{5-[2-(methylthio)ethoxy]pyrimidin-2-yl}-6-oxo-1,6-dihydropyrimidin-5-yl}methyl}pyridin-2-yl}phenyl}-1,2,4-oxadiazol-5(4H)-one, 3-{2-{5-{{4-butyl-2-methyl-1-{5-[2-(methylsulfonyl)ethoxy]pyrimidin-2-yl}-6-oxo-1,6-dihydropyrimidin-5-yl}methyl}pyridin-2-yl}phenyl}-1,2,4-oxadiazol-5(4H)-one, 5-{{5-[2-(1H-tetrazol-5-yl)phenyl]pyridin-2-yl}methyl}-6-butyl-2-methyl-3-(pyridin-2-yl)pyrimidin-4(3H)-one, 5-{{5-[2-(1H-tetrazol-5-yl)phenyl]pyridin-2-yl}methyl}-6-butyl-3-(5-methoxypyridin-2-yl)-2-methylpyrimidin-4(3H)-one, 5-{{5-[2-(1H-tetrazol-5-yl)phenyl]pyridin-2-yl}methyl}-6-butyl-3-[3-chloro-5-(trifluoromethyl)pyridin-2-yl]-2-methylpyrimidin-4(3H)-one, 5-{{5-[2-(1H-tetrazol-5-yl)phenyl]pyridin-2-yl}methyl}-6-butyl-3-(5-methoxypyridin-2-yl)-2-methylpyrimidin-4(3H)-one, 5-{{5-[2-(1H-tetrazol-5-yl)phenyl]pyridin-2-yl}methyl}-6-butyl-3-(5-ethoxypyridin-2-yl)-2-methylpyrimidin-4(3H)-one, 5-{{5-[2-(1H-tetrazol-5-yl)phenyl]pyridin-2-yl}methyl}-6-butyl-3-(4,6-dimethoxypyrimidin-2-yl)-2-methylpyrimidin-4(3H)-one, 3-{2-{6-{[4-butyl-1-(5-methoxypyridin-2-yl)-2-methyl-6-oxo-1,6-dihydropyrimidin-5-yl]methyl}pyridin-3-yl}phenyl}-1,2,4-oxadiazol-5(4H)-one, 3-{2-{6-{[4-butyl-1-(5-methoxypyrimidin-2-yl)-2-methyl-6-oxo-1,6-dihydropyrimidin-5-yl]methyl}pyridin-3-yl}phenyl}-1,2,4-oxadiazol-5(4H)-one, 3-{2-{6-{[4-butyl-1-(5-ethoxypyrimidin-2-yl)-2-methyl-6-oxo-1,6-dihydropyrimidin-5-yl]methyl}pyridin-3-yl}phenyl}-1,2,4-oxadiazol-5(4H)-one, 3-{2-{6-{[4-butyl-1-(4,6-dimethoxypyrimidin-2-yl)-2-methyl-6-oxo-1,6-dihydropyrimidin-5-yl]methyl}pyridin-3-yl}phenyl}-1,2,4-oxadiazol-5(4H)-one, 3-{2-{5-{[1-(5-ethoxypyrimidin-2-yl)-2-isopropyl-6-oxo-4-propyl-1,6-dihydropyrimidin-5-yl]methyl}pyridin-2-yl}phenyl}-1,2,4-oxadiazol-5(4H)-one, 3-{2-{5-{[2-cyclopropyl-1-(5-ethoxypyrimidin-2-yl)-6-oxo-4-propyl-1,6-dihydropyrimidin-5-yl]methyl}pyridin-2-yl}phenyl}-1,2,4-oxadiazol-5(4H)-one, 3-{2-{5-{[1-(5-ethoxypyrimidin-2-yl)-2-isopropyl-6-oxo-4-pentyl-1,6-dihydropyrimidin-5-yl]methyl}pyridin-2-yl}phenyl}-1,2,4-oxadiazol-5(4H)-one, 3-{2-{5-{[2-cyclopropyl-1-(5-ethoxypyrimidin-2-yl)-6-oxo-4-pentyl-1,6-dihydropyrimidin-5-yl]methyl}pyridin-2-yl}phenyl}-1,2,4-oxadiazol-5(4H)-one, 3-{2-{5-{[1-(5-ethoxypyrimidin-2-yl)-4-ethyl-2-isopropyl-6-oxo-1,6-dihydropyrimidin-5-yl]methyl}pyridin-2-yl}phenyl}-1,2,4-oxadiazol-5(4H)-one, and 3-{2-{5-{[2-cyclopropyl-1-(5-ethoxypyrimidin-2-yl)-4-ethyl-6-oxo-1,6-dihydropyrimidin-5-yl]methyl}pyridin-2-yl}phenyl}-1,2,4-oxadiazol-5(4H)-one.

More preferred examples of the 5-(pyridinylmethyl)pyrimidin-4(3H)-one derivatives that are represented by the formula (I) include a compound selected from a group consisting of the following compounds:

5-{{6-[2-(1H-tetrazol-5-yl)phenyl]pyridin-3-yl}methyl}-6-butyl-2-isopropyl-3-(5-methoxypyrimidin-2-yl)pyrimidin-4(3H)-one, 5-{{6-[2-(1H-tetrazol-5-yl)phenyl]pyridin-3-yl}methyl}-6-butyl-3-(5-ethoxypyrimidin-2-yl)-2-isopropylpyrimidin-4(3H)-one, 5-{{6-[2-(1H-tetrazol-5-yl)phenyl]pyridin-3-yl}methyl}-6-butyl-2-cyclopropyl-3-(5-methoxypyrimidin-2-yl)pyrimidin-4(3H)-one, 5-{{6-[2-(1H-tetrazol-5-yl)phenyl]pyridin-3-yl}methyl}-6-butyl-2-cyclobutyl-3-(5-methoxypyrimidin-2-yl)pyrimidin-4(3H)-one, 5-{{6-[2-(1H-tetrazol-5-yl)phenyl]pyridin-3-yl}methyl}-6-butyl-2-cyclobutyl-3-(5-ethoxypyrimidin-2-yl)pyrimidin-4(3H)-one, 5-{{6-[2-(1H-tetrazol-5-yl)phenyl]pyridin-3-yl}methyl}-6-butyl-2-cyclopentyl-3-(5-ethoxypyrimidin-2-yl)pyrimidin-4(3H)-one, 5-{{6-[2-(1H-tetrazol-5-yl)phenyl]pyridin-3-yl}methyl}-6-butyl-2-cyclohexyl-3-(5-ethoxypyrimidin-2-yl)pyrimidin-4(3H)-one, 3-{2-{5-{[4-butyl-2-isopropyl-1-(5-methoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-1-(5-ethoxypyrimidin-2-yl)-2-isopropyl-6-oxo-1,6-dihydropyrimidin-5-yl]methyl}pyridin-2-yl}phenyl}-1,2,4-oxadiazol-5(4H)-one, 3-{2-{5-{[4-butyl-2-cyclopropyl-1-(5-methoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclopropyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclobutyl-1-(5-methoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclobutyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclopentyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[4-butyl-2-cyclohexyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one, 3-{2-{5-{[1-(5-ethoxypyrimidin-2-yl)-2-isopropyl-6-oxo-4-propyl-1,6-dihydropyrimidin-5-yl]methyl}pyridin-2-yl}phenyl}-1,2,4-oxadiazol-5(4H)-one, 3-{2-{5-{[2-cyclopropyl-1-(5-ethoxypyrimidin-2-yl)-6-oxo-4-propyl-1,6-dihydropyrimidin-5-yl]methyl}pyridin-2-yl}phenyl}-1,2,4-oxadiazol-5(4H)-one, 3-{2-{5-{[1-(5-ethoxypyrimidin-2-yl)-2-isopropyl-6-oxo-4-pentyl-1,6-dihydropyrimidin-5-yl]methyl}pyridin-2-yl}phenyl}-1,2,4-oxadiazol-5(4H)-one, 3-{2-{5-{[2-cyclopropyl-1-(5-ethoxypyrimidin-2-yl)-6-oxo-4-pentyl-1,6-dihydropyrimidin-5-yl]methyl}pyridin-2-yl}phenyl}-1,2,4-oxadiazol-5(4H)-one, 3-{2-{5-{[1-(5-ethoxypyrimidin-2-yl)-4-ethyl-2-isopropyl-6-oxo-1,6-dihydropyrimidin-5-yl]methyl}pyridin-2-yl}phenyl}-1,2,4-oxadiazol-5(4H)-one, and 3-{2-{5-{[2-cyclopropyl-1-(5-ethoxypyrimidin-2-yl)-4-ethyl-6-oxo-1,6-dihydropyrimidin-5-yl]methyl}pyridin-2-yl}phenyl}-1,2,4-oxadiazol-5(4H)-one.

Still more preferred examples of the 5-(pyridinylmethyl)pyrimidin-4(3H)-one derivatives that are represented by the formula (I) include a compound selected from a group consisting of the following compounds:

3-{2-{5-{[1-(5-ethoxypyrimidin-2-yl)-2-isopropyl-6-oxo-4-propyl-1,6-dihydropyrimidin-5-yl]methyl}pyridin-2-yl}phenyl}-1,2,4-oxadiazol-5(4H)-one, 3-{2-{5-{[2-cyclopropyl-1-(5-ethoxypyrimidin-2-yl)-6-oxo-4-propyl-1,6-dihydropyrimidin-5-yl]methyl}pyridin-2-yl}phenyl}-1,2,4-oxadiazol-5(4H)-one, 3-{2-{5-{[1-(5-ethoxypyrimidin-2-yl)-2-isopropyl-6-oxo-4-pentyl-1,6-dihydropyrimidin-5-yl]methyl}pyridin-2-yl}phenyl}-1,2,4-oxadiazol-5(4H)-one, 3-{2-{5-{[2-cyclopropyl-1-(5-ethoxypyrimidin-2-yl)-6-oxo-4-pentyl-1,6-dihydropyrimidin-5-yl]methyl}pyridin-2-yl}phenyl}-1,2,4-oxadiazol-5(4H)-one, 3-{2-{5-{[1-(5-ethoxypyrimidin-2-yl)-4-ethyl-2-isopropyl-6-oxo-1,6-dihydropyrimidin-5-yl]methyl}pyridin-2-yl}phenyl}-1,2,4-oxadiazol-5(4H)-one, and 3-{2-{5-{[2-cyclopropyl-1-(5-ethoxypyrimidin-2-yl)-4-ethyl-6-oxo-1,6-dihydropyrimidin-5-yl]methyl}pyridin-2-yl}phenyl}-1,2,4-oxadiazol-5(4H)-one.

If the compound of the invention has geometrical isomers or optical isomers, all of such isomers are within the scope of the invention. Isolation of these isomers is carried out by an ordinary method.

Salts of the compound represented by the formula (I) are not particularly limited, if they are pharmaceutically acceptable salts. When the compound is processed as an acidic compound, an alkali metal salt or an alkali earth metal salt such as sodium salt, potassium salt, magnesium salt, and calcium salt, and the like; and a salt with an organic base such as trimethylamine, triethylamine, pyridine, picoline, N-methyl pyrrolidine, N-methyl piperidine, N-methyl morpholine, and the like can be mentioned. When the compound is processed as a basic compound, an acid addition salt and the like including a salt with a mineral acid, for example, hydrochloric acid salt, hydrobromic acid salt, hydroiodic acid salt, sulfuric acid salt, nitric acid salt, phosphoric acid salt, and the like; or organic acid addition salt, for example, benzoic acid salt, methanesulfonic acid salt, ethanesulfonic acid salt, benzenesulfonic acid salt, p-toluene sulfonic acid salt, maleic acid salt, fumaric acid salt, tartaric acid salt, citric acid salt, and acetic acid salt; or the like can be mentioned.

Examples of the solvate of the compound represented by the formula (I) or a salt thereof include a hydrate, but not limited thereto.

In addition, compounds which are metabolized in a living body and converted into the compounds represented by the aforementioned formula (I), so called prodrugs, all fall within the scope of the compounds of the invention. Examples of groups which form the prodrugs of the compounds of the invention include the groups described in "Progress in Medicine", Vol. 5, pp. 2157-2161, 1985, Life Science Medica, and the groups described in "Development of Drugs", Vol. 7, Molecular Designs, pp. 163-198, published in 1990, Hirokawa Shoten.

The compounds represented by the formula (I) or salts thereof, or solvates thereof can be produced according to various known methods, and the production method is not specifically limited. For example, the compounds can be produced according to the following reaction process. Further, when each reaction described below is performed, functional groups other than the reaction sites may be protected beforehand as required, and deprotected in an appropriate stage. Furthermore, the reaction in each process may be performed by an ordinarily used method, and isolation and purification can be performed by a method suitably selected from conventional methods such as crystallization, recrystallization, chromatography, or the like, or a combination thereof.

(Production Method)

1. Method for Production of the Compound (Ia) in which the Ring B is the Formula (IV)

Among the compounds represented by the formula (I) of the invention, the compound represented by the formula (Ia) can be produced according to the following method, but it is not limited thereto. Specifically, as described in the following Reaction pathway 1, if pyridinyl methyl halide (VI) and β-ketoester (VII) are reacted with each other and the obtained compound (VIII) are reacted with ammonium acetate followed by reaction with acid anhydride (IX) or acid chloride (X), acylamino compound (XI) is obtained. If the acylamino compound (XI) is reacted with amino compound (XII), pyrimidinone derivative (XIII) is obtained. If the pyrimidinone derivative (XIII) is reacted with an azide compound, the compound represented by the formula (Ia) of the invention can be obtained.

[Reaction Pathway 1]

[Chemical Formula 6]

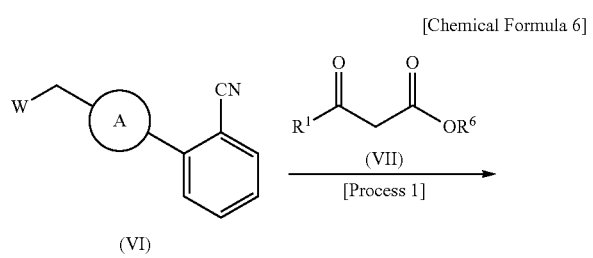

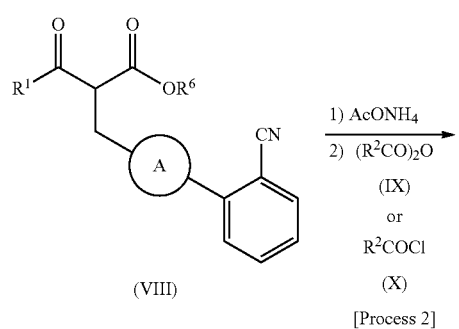

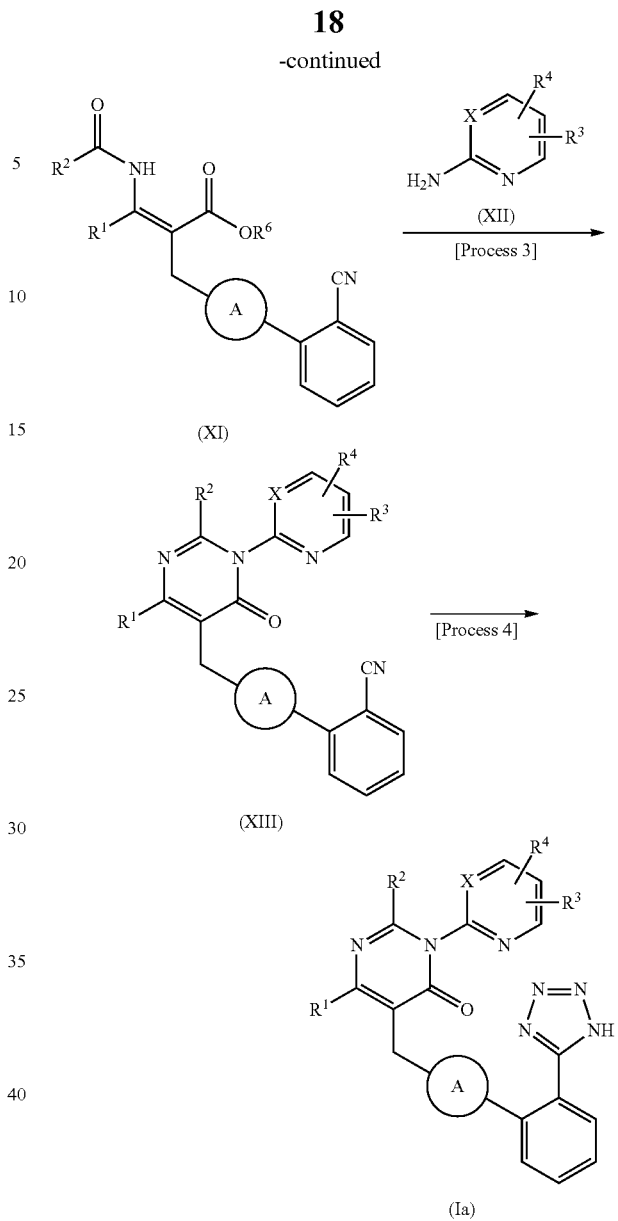

(in the formula, ring A, $R^1$, $R^2$, $R^3$, $R^4$, and X are as defined above, $R^6$ represents a protecting group for carboxyl group such as $C_{1-8}$ alkyl group, and W represents a leaving group such as halogen atom).

[Process 1] The reaction between the pyridinyl methyl halide (VI) and the β-ketoester (VII) may be carried out in a solvent in the presence of a base and lithium halide (lithium chloride, lithium bromide, and the like). The solvent is not specifically limited, and N,N-dimethyl formamide, N-methyl pyrrolidone, dimethyl sulfoxide, dioxane, tetrahydrofuran, acetonitrile, and propionitrile may be used either alone or in combination thereof. The base is not specifically limited, and examples thereof which may be used include an organic base such as pyridine, N,N-dimethylaminopyridine (DMAP), collidine, lutidine, 1,8-diazabicyclo[5.4.0]-7-undecene (DBU), 1,5-diazabicyclo[4.3.0]-5-nonene (DBN), 1,4-diazabicyclo[2.2.2]octane (DABCO), triethylamine, diisopropylamine, diisopropylethylamine, diisopropylpentylamine, and trimethylamine, an alkali metal hydride such as lithium hydride, sodium hydride, and potassium hydride, an alkali metal hydroxide such as lithium hydroxide, sodium hydroxide, and potassium hydroxide, an alkali metal carbonate such as lithium carbonate, sodium carbonate, potassium carbonate, and cesium carbonate, and an alkali metal bicarbonate such as sodium hydrogen carbonate. The reaction condition may vary depending on the reaction materials used. However, the reaction is generally carried out at −20 to 120° C., and preferably 20° C. to 100° C., for 1 minute to 2 days, and preferably for 5 minutes to 36 hours to obtain the compound (VIII).

[Process 2-1] The reaction between the compound (VIII) and ammonium acetate may be carried out in a solvent in the presence of an acid. The solvent is not specifically limited, and methanol, ethanol, isopropanol, ethyl acetate, isopropyl acetate, toluene, benzene, dioxane, tetrahydrofuran, acetonitrile, propionitrile, N,N-dimethylformamide, N-methylpyrrolidone, and dimethyl sulfoxide may be used either alone or in combination thereof. The acid is not specifically limited, and examples thereof which may be used include a protic acid such as acetic acid, trifluoro acetic acid, propionic acid, and benzoic acid and Lewis acid such as titanium tetrachloride, boron trifluoride, and stannic chloride. The reaction condition may vary depending on the reaction materials used. However, the reaction is generally carried out at 0 to 180° C., and preferably 50° C. to 150° C., for 1 minute to 24 hours, and preferably for 5 minutes to 18 hours.

[Process 2-2] The reaction between the crude product obtained after distillation of solvent and the acid anhydride (IX) may be carried out in the presence of an acid. The acid is not particularly limited, and examples thereof which may be used include a protic acid like acetic acid, trifluoroacetic acid, propionic acid, and benzoic acid. The reaction condition may vary depending on the reaction materials used. However, the reaction is generally carried out at 0 to 180° C., and preferably 50° C. to 120° C., for 1 minute to 2 days, and preferably for 5 minutes to 24 hours to obtain the acylamino compound (XI).

The reaction between the crude product obtained after distillation of solvent and the acid chloride (X) may be carried out in a solvent in the presence or absence of a base. The solvent is not specifically limited, and tetrahydrofuran, toluene, dioxane, N,N-dimethylformamide, N-methylpyrrolidone, 1,2-dichloroethane, dichloromethane, chloroform, acetonitrile, and propionitrile may be used either alone or in combination thereof. The base is not specifically limited, and examples thereof which may be used include an organic base like pyridine, DMAP, collidine, lutidine, DBU, DBN, DABCO, triethylamine, diisopropylamine, diisopropylethylamine, diisopropylpentylamine, and trimethylamine, an alkali metal hydride like lithium hydride, sodium hydride, and potassium hydride, an alkali metal hydroxide like lithium hydroxide, sodium hydroxide, and potassium hydroxide, an alkali metal carbonate like lithium carbonate, sodium carbonate, potassium carbonate, and cesium carbonate, and sodium hydrogen carbonate. The reaction condition may vary depending on the reaction materials used. However, the reaction is generally carried out at −20 to 100° C., and preferably 15 to 80° C., for 5 minutes to 48 hours, and preferably for 5 hours to 36 hours to obtain the acylamino compound (XI).

[Process 3] The reaction between the acylamino compound (XI) obtained according to the method above and the amino compound (XII) may be carried out in a solvent in the presence of trialkylaluminum. The solvent is not specifically limited, and 1,2-dichloroethane, chloroform, dichloromethane, ethyl acetate, isopropyl acetate, toluene, benzene, tetrahydrofuran, dioxane, acetonitrile, propionitrile, and hexane may be used either alone or in combination thereof. Examples of the trialkylaluminum which may be used include trimethylaluminum, triethylaluminum, and tripropylaluminum. The reaction condition may vary depending on the reaction materials used. However, the reaction is generally carried out at 0 to 150° C., and preferably 50° C. to 120° C., for 1 minute to 24 hours, and preferably for 5 minutes to 20 hours to obtain the pyrimidinone derivative (XIII).

[Process 4] The reaction between the pyrimidinone derivative (XIII) and an azide compound may be carried out in a solvent. Examples of the azide compound which may be used include trimethyltin azide, tributyltin azide, triphenyltin azide, sodium azide, and hydrogen azide. Further, trimethylsilyl azide may be used in the presence of dibutyltin oxide. The solvent is not specifically limited, and methanol, ethanol, isopropanol, ethyl acetate, isopropyl acetate, toluene, benzene, dioxane, tetrahydrofuran, acetonitrile, propionitrile, N,N-dimethylformamide, N-methylpyrrolidone, and dimethyl sulfoxide may be used either alone or in combination thereof. The reaction condition may vary depending on the reaction materials used. However, the reaction is generally carried out at 0 to 180° C., and preferably 50 to 120° C., for 1 minute to 2 weeks, and preferably for 1 hour to 3 days to obtain the target compound.

2. Method for Production of the Compound (Ib) in which the Ring B is the Formula (V)

Among the compounds represented by the formula (I) of the invention, the compound represented by the formula (Ib) can be produced according to the following method, but it is not limited thereto. Specifically, as described in the following Reaction pathway 2, if the pyrimidinone derivative (XIII) and hydroxylamine are reacted with each other, amide oxime product (XIV) is obtained. If the amide oxime product (XIV) is reacted with a carbonyl reagent, the compound represented by the formula (Ib) of the invention can be produced.

[Reaction Pathway 2]

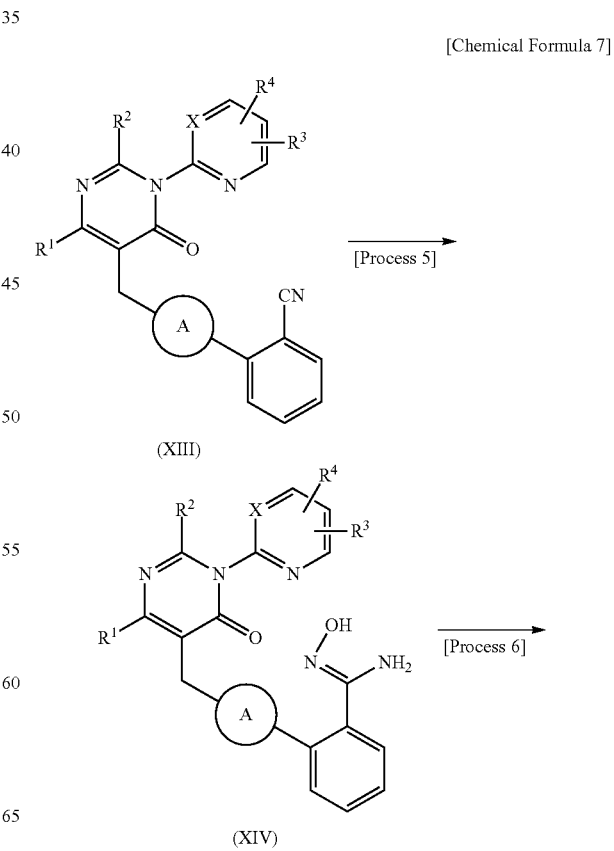

[Chemical Formula 7]

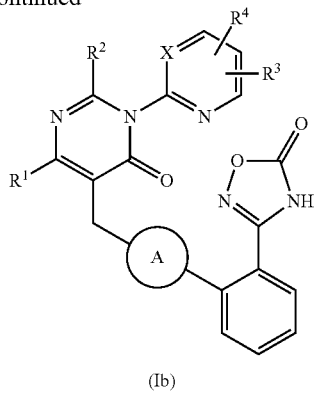

(in the formula, ring A, $R^1$, $R^2$, $R^3$, $R^4$, and X are as defined above).

[Process 5] The reaction between the pyrimidinone derivative (XIII) and hydroxylamine may be carried out in a solvent. The solvent is not specifically limited, and N,N-dimethylformamide, N,N-dimethylacetamide, N-methyl pyrrolidone, dimethyl sulfoxide, methanol, ethanol, isopropanol, 1,4-dioxane, and tetrahydrofuran may be used either alone or in combination thereof. When an acid salt such as hydroxylamine hydrochloride, hydroxylamine sulfuric acid, hydroxylamine oxalic acid, and the like is used as hydroxylamine, a suitable base, for example, potassium carbonate, sodium hydrogen carbonate, sodium hydroxide, triethylamine, sodium methoxide, sodium hydride, and the like may be used in an equivalent amount or a slightly excess amount for the reaction. The reaction condition may vary depending on the reaction materials used. However, the reaction is generally carried out at 0 to 180° C., and preferably 50 to 120° C., for 1 minute to 3 days, and preferably for 1 hour to 36 hours. As a result, the amide oxime product (XIV) is obtained.

[Process 6] Conversion of the amide oxime product (XIV) to the compound (Ib) can be carried out in a solvent in the presence of a base by using a carbonyl reagent. The solvent is not specifically limited, and 1,2-dichloroethane, chloroform, dichloromethane, ethyl acetate, isopropyl acetate, toluene, benzene, tetrahydrofuran, dioxane, acetonitrile, propionitrile, N,N-dimethylformamide, N,N-dimethylacetamide, N-methylpyrrolidone, diethyl ether, or the like may be used either alone or in combination thereof. The base is not specifically limited, and examples thereof which may be used include pyridine, DMAP, collidine, lutidine, DBU, DBN, DABCO, triethylamine, diisopropylethylamine, diisopropylpentylamine, trimethylamine, lithium carbonate, sodium carbonate, potassium carbonate, cesium carbonate, sodium hydrogen carbonate, potassium hydrogen carbonate, or the like. The carbonyl reagent is not specifically limited, and 1,1'-carbonyldiimidazole, triphosgene, methyl chlorocarbonate, ethyl chlorocarbonate, or the like may be used. The reaction condition may vary depending on the reaction materials used. However, the reaction is generally carried out at 0 to 120° C., preferably 15 to 80° C. for 5 minutes to 3 days, and preferably for 1 hour to 12 hours to obtain the compound (Ib).

If necessary, the intermediates and target compounds that are obtained from each of the reaction above can be isolated and purified by a purification method that is generally used in a field of organic synthesis chemistry, for example, filtration, extraction, washing, drying, concentration, recrystallization, various chromatographic methods, and the like. Furthermore, the intermediates may be used for the next reaction without any specific purification.

Various isomers may be isolated by applying a general method based on a difference in physicochemical properties among the isomers. For example, a racemic mixture may be resolved into an optically pure isomer by common racemic resolution such as optical resolution by which a diastereomer salt is formed with a common optically active acid such as tartaric acid or a method of using optically active chromatography. Further, a mixture of diastereomers can be resolved by fractional crystallization or various chromatographic methods, for example. Furthermore, an optically active compound can be also produced by using an appropriate starting compound that is optically active.

The compound (I) obtained may be converted into a salt according to a common method. Furthermore, the compound (I) or a salt thereof may be converted into a solvate with a hydrate or a solvate with ethanol according to a common method.

Examples of dosage form or administration type of the pharmaceutical composition containing the compounds of the invention or salts thereof, or solvates thereof as an effective component include, for example, those for oral administration such as tablet, capsule, granule, powder, syrup, or the like and those for parenteral administration such as intravenous injection, intramuscular injection, suppository, inhalant, transdermal preparation, eye drop, nasal drop, or the like. In order to prepare a pharmaceutical preparation in the various dosage forms, the effective component may be used alone, or may be used in appropriate combination with other pharmaceutically acceptable carriers such as excipients, binders, extending agents, disintegrating agents, surfactants, lubricants, dispersing agents, buffering agents, preservatives, corrigents, perfumes, coating agents, diluents, and the like to give a pharmaceutical composition.

Although the administration amount of the pharmaceutical agent of the invention may vary depending on the weight, age, sex, symptoms, and the like of a patient, in terms of the compound represented by the formula (I), generally 0.1 to 1000 mg, especially 1 to 300 mg, may be administered orally or parenterally at one time or several times as divided portions per day for an adult.

EXAMPLES

Herein below, the invention will be described in greater detail with reference to examples. However, the invention is not limited to these examples. The abbreviations used in the examples have the following meanings.

s: singlet d: doublet t: triplet q: quartet m: multiplet br: broad

J: coupling constant

Hz: Hertz $CDCl_3$: deuterated chloroform

DMSO-$d_6$: deuterated dimethylsulfoxide $^1$H-NMR: proton nuclear magnetic resonance IR: infrared absorption spectrum

Example 1

Preparation of 5-{{6-[2-(1H-tetrazol-5-yl)phenyl]pyridin-3-yl}methyl}-6-butyl-3-(5-methoxypyrimidin-2-yl)-2-methylpyrimidin-4(3H)-one

[Chemical Formula 8]

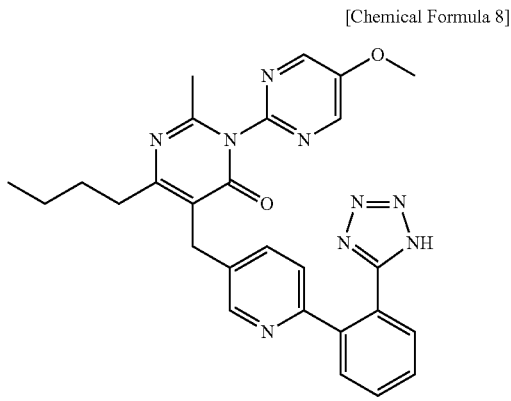 [SMILES: CCCCc1nc(C)n(-c2ncc(OC)cn2)c(=O)c1Cc1ccc(-c2ccccc2-c2nnn[nH]2)nc1]

Process 1: Under argon atmosphere, tetrahydrofuran (900 mL) solution of 2-[5-(bromomethyl)pyridin-2-yl]benzonitrile (31.9 g, 117 mmol), methyl 3-oxoheptanoate (27.8 g, 176 mmol), diisopropylethylamine (31.0 g, 240 mmol), and lithium chloride (8.2 g, 193 mmol) was refluxed under heating for 23 hours. The reaction mixture was added water and extracted with ethyl acetate. The organic layer was combined, washed with water and brine, dried over anhydrous sodium sulfate, and concentrated in vacuo. The obtained residues were subjected to silica gel column chromatography (hexane/ethyl acetate=2:1) to give methyl 2-{[6-(2-cyanophenyl)pyridin-3-yl]methyl}-3-oxoheptanoate (20.9 g, 51%) as brown oil.

$^1$H-NMR (CDCl$_3$, 400 MHz) δ:

0.87 (3H, t, J=7 Hz), 1.18-1.32 (2H, m), 1.47-1.59 (2H, m), 2.34-2.39 (1H, m), 2.55-2.67 (1H, m), 3.20-3.29 (2H, m), 3.73 (3H, s), 3.84 (1H, t, J=7 Hz), 7.50 (1H, td, J=8, 1 Hz), 7.63-7.74 (3H, m), 7.76-7.87 (2H, m), 8.61 (1H, s).

Process 2: Toluene (50 mL)-acetic acid (7 mL) solution of methyl 2-{[6-(2-cyanophenyl)pyridin-3-yl]methyl}-3-oxoheptanoate (3.50 g, 10.0 mmol) and ammonium acetate (23.2 g, 300 mmol) was refluxed under heating for 1 hour. To the residues obtained after distillation of solvent, acetic anhydride (51.2 g) and acetic acid (5.7 g) were added at room temperature followed by stirring for 30 minutes at 0° C. and then stirring for 1.5 hours at 70° C. The reaction mixture was added sodium bicarbonate water, and then extracted with chloroform. The organic layer was combined, washed with brine, dried over anhydrous sodium sulfate, and concentrated in vacuo. The obtained residues were subjected to silica gel column chromatography (hexane/acetone=5:1) to give methyl (Z)-3-acetamide-2-{[6-(2-cyanophenyl)pyridin-3-yl]methyl}-2-heptenoate (0.975 g, 25%) as pale yellow oil.

$^1$H-NMR (CDCl$_3$, 400 MHz) δ:

0.91 (3H, t, J=7 Hz), 1.33-1.45 (2H, m), 1.46-1.57 (2H, m), 2.18 (3H, s), 2.94 (2H, t, J=6 Hz), 3.71 (3H, s), 3.75 (2H, s), 7.50 (1H, t, J=8 Hz), 7.58 (1H, d, J=8 Hz), 7.63-7.72 (2H, m), 7.75-7.83 (2H, m), 8.60 (1H, s), 11.9 (1H, s).

Process 3: Under argon atmosphere, trimethylaluminum (2 mol/L hexane solution, 1.45 mL, 2.90 mmol) was added to 1,2-dichloroethane (30 mL) solution of 2-amino-5-methoxypyrimidine (220 mg, 1.74 mmol) at room temperature, and stirred at the same temperature for 80 minutes. 1,2-Dichloroethane solution (20 mL) of methyl (Z)-3-acetamide-2-{[6-(2-cyanophenyl)pyridin-3-yl]methyl}-2-heptenoate (227 mg, 0.58 mmol) was added dropwise thereto at room temperature and refluxed under heating for 17 hours. The reaction mixture was added an aqueous solution of ammonium chloride and chloroform and filtered through a pad of celite. The organic layer was separated from the filtrate and the aqueous layer was extracted with chloroform. The organic layer was combined, washed with water and brine, dried over anhydrous sodium sulfate, and concentrated in vacuo. The obtained residues were subjected to silica gel column chromatography (hexane/ethyl acetate=2:1) to give 2-{5-{[4-butyl-1-(5-methoxypyrimidin-2-yl)-2-methyl-6-oxo-1,6-dihydropyrimidin-5-yl]methyl}pyridin-2-yl}benzonitrile (207 mg, 77%) as yellow oil.

$^1$H-NMR (CDCl$_3$, 400 MHz) δ:

0.95 (3H, t, J=7 Hz), 1.36-1.48 (2H, m), 1.58-1.70 (2H, m), 2.16 (3H, s), 2.63-2.72 (2H, m), 3.97 (2H, s), 4.01 (2H, s), 7.47 (1H, m), 7.60-7.71 (2H, m), 7.72-7.83 (3H, m), 8.54 (2H, s), 8.70 (1H, d, J=1 Hz).

Process 4: Trimethylsilyl azide (8.68 g, 75.3 mmol) and dibutyltin oxide (55 mg, 0.221 mmol) were added to toluene (20 mL) solution of 2-{5-{[4-butyl-1-(5-methoxypyrimidin-2-yl)-2-methyl-6-oxo-1,6-dihydropyrimidin-5-yl]methyl}pyridin-2-yl}benzonitrile (200 mg, 0.43 mmol) and stirred for 24 hours at 95° C. under argon atmosphere. The residues obtained by removing the reaction solvent by distillation was separated and purified by silica gel column chromatography (chloroform:methanol=100:1) to give 5-{{6-[2-(1H-tetrazol-5-yl)phenyl]pyridin-3-yl}methyl}-6-butyl-3-(5-methoxypyrimidin-2-yl)-2-methylpyrimidin-4(3H)-one (174 mg, 80%) as yellow oil.

$^1$H-NMR (CDCl$_3$, 400 MHz) δ:

0.93 (3H, t, J=7 Hz), 1.33-1.48 (2H, m), 1.55-1.73 (2H, m), 2.16 (3H, s), 2.58-2.72 (2H, m), 3.95 (2H, s), 4.00 (3H, s), 7.20-7.35 (1H, m), 7.38-7.58 (3H, m), 7.62-7.82 (1H, m), 8.00-8.22 (1H, m), 8.54 (2H, s), 8.50-8.63 (1H, m).

Example 2

Preparation of 5-{{6-[2-(1H-tetrazol-5-yl)phenyl]pyridin-3-yl}methyl}-6-butyl-3-(5-ethoxypyrimidin-2-yl)-2-methylpyrimidin-4(3H)-one

[Chemical Formula 9]

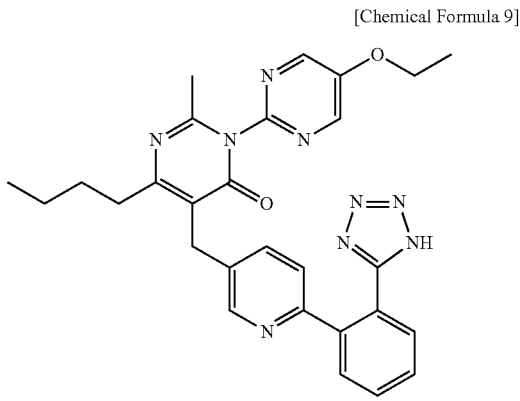 [SMILES: CCCCc1nc(C)n(-c2ncc(OCC)cn2)c(=O)c1Cc1ccc(-c2ccccc2-c2nnn[nH]2)nc1]

Process 1: By using 2-amino-5-ethoxypyrimidine instead of 2-amino-5-methoxypyrimidine in the Process 3 of the Example 1, the reaction and the treatment were performed in the same manner as the Process 3 of the Example 1 to give 2-{5-{[4-butyl-1-(5-ethoxypyrimidin-2-yl)-2-methyl-6-oxo-1,6-dihydropyrimidin-5-yl]methyl}pyridin-2-yl}benzonitrile (yield: 46%).

$^1$H-NMR (CDCl$_3$, 400 MHz) δ:
0.94 (3H, t, J=7 Hz), 1.38-1.46 (2H, m), 1.51 (3H, t, J=7 Hz), 1.60-1.68 (2H, m), 2.16 (3H, s), 2.65-2.69 (2H, m), 3.97 (2H, s), 4.22 (2H, q, J=7 Hz), 7.47 (1H, m), 7.64-7.81 (5H, m), 8.51 (2H, s), 8.70 (1H, d, J=1 Hz).

Process 2: By using 2-{5-{[4-butyl-1-(5-ethoxypyrimidin-2-yl)-2-methyl-6-oxo-1,6-dihydropyrimidin-5-yl]methyl}pyridin-2-yl}benzonitrile instead of 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of the Example 1, the reaction and the treatment were performed in the same manner as the Process 4 of the Example 1 to give 5-{{6-[2-(1H-tetrazol-5-yl)phenyl]pyridin-3-yl}methyl}-6-butyl-3-(5-ethoxypyrimidin-2-yl)-2-methylpyrimidin-4(3H)-one (yield: 46%) as pale yellow amorphous.

$^1$H-NMR (CDCl$_3$, 400 MHz) δ:
0.94 (3H, t, J=7 Hz), 1.38-1.44 (2H, m), 1.51 (3H, t, J=7 Hz), 1.61-1.68 (2H, m), 2.17 (3H, s), 2.66-2.70 (2H, m), 3.97 (2H, s), 4.22 (2H, q, J=7 Hz), 7.37 (1H, m), 7.48-7.58 (3H, m), 7.78 (1H, m), 8.21 (1H, m), 8.51 (2H, s), 8.62 (1H, m).

Example 3

Preparation of 5-{{6-[2-(1H-tetrazol-5-yl)phenyl]pyridin-3-yl}methyl}-6-butyl-2-ethyl-3-(5-methoxypyrimidin-2-yl)pyrimidin-4(3H)-one

[Chemical Formula 10]

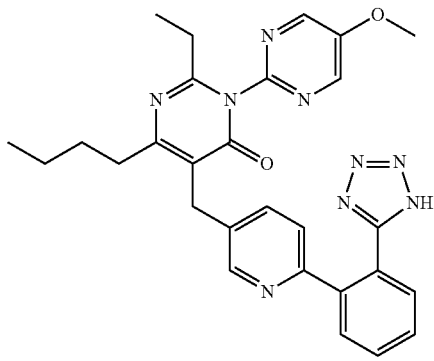

Process 1: Toluene (36 mL)-acetic acid (4 mL) solution of methyl 2-{[6-(2-cyanophenyl)pyridin-3-yl]methyl}-3-oxoheptanoate (1.03 g, 2.94 mmol) obtained from the Process 1 of the Example 1 and ammonium acetate (6.80 g, 88.2 mmol) was refluxed under heating for 1 hour. The residues obtained by removing solvent by distillation were added water and 2 mol/L aqueous solution of sodium hydroxide and extracted with chloroform. Propionyl chloride (544 mg, 5.88 mmol) and triethylamine (595 mg, 5.88 mmol) were added to the 1,2-dichloroethane (10 mL) solution of the residues obtained by removing solvent by distillation and stirred for 16 hours at 50° C. The reaction mixture was added water and extracted with chloroform. The organic layer was combined, washed with brine, dried over anhydrous sodium sulfate, and concentrated in vacuo. The obtained residues were subjected to silica gel column chromatography (hexane/acetone=5:1) to give methyl (Z)-2-{[6-(2-cyanophenyl)pyridin-3-yl]methyl}-3-propionamide-2-heptenoate (464 mg, 39%) as brown oil.

$^1$H-NMR (CDCl$_3$, 400 MHz) δ:
0.91 (3H, t, J=7 Hz), 1.23 (3H, t, J=8 Hz), 1.34-1.51 (4H, m), 2.43 (2H, q, J=8 Hz), 2.89-2.99 (2H, m), 3.70 (3H, s), 3.75 (2H, s), 7.49 (1H, td, J=8, 1 Hz), 7.58 (1H, dd, J=8, 2 Hz), 7.64-7.73 (2H, m), 7.77-7.86 (2H, m), 8.60 (1H, s), 11.88 (1H, s).

Process 2: By using methyl (Z)-2-{[6-(2-cyanophenyl)pyridin-3-yl]methyl}-3-propionamide-2-heptenoate instead of methyl (Z)-3-acetamide-2-{[6-(2-cyanophenyl)pyridin-3-yl]methyl}-2-heptenoate in the Process 3 of the Example 1, the reaction and the treatment were performed in the same manner as the Process 3 of the Example 1 to give 2-{5-{[4-butyl-2-ethyl-1-(5-methoxypyrimidin-2-yl)-6-oxo-1,6-dihydropyrimidin-5-yl]methyl}pyridin-2-yl}benzonitrile (yield: 70%) as a pale yellow solid.

$^1$H-NMR (CDCl$_3$, 400 MHz) δ:
0.94 (3H, t, J=7 Hz), 1.18 (3H, t, J=7 Hz), 1.35-1.46 (2H, m), 1.62-1.74 (2H, m), 2.32 (2H, q, J=7 Hz), 2.69 (2H, t, J=8 Hz), 3.96 (2H, s), 4.00 (3H, s), 7.47 (1H, td, J=8, 1 Hz), 7.61-7.70 (2H, m), 7.73-7.82 (3H, m), 8.53 (2H, s), 8.69 (1H, s).

Process 3: By using 2-{5-{[4-butyl-2-ethyl-1-(5-methoxypyrimidin-2-yl)-6-oxo-1,6-dihydropyrimidin-5-yl]methyl}pyridin-2-yl}benzonitrile instead of 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of the Example 1, the reaction and the treatment were performed in the same manner as the Process 4 of the Example 1 to give 5-{{6-[2-(1H-tetrazol-5-yl)phenyl]pyridin-3-yl}methyl}-6-butyl-2-ethyl-3-(5-methoxypyrimidin-2-yl)pyrimidin-4(3H)-one (yield: 60%) as colorless viscous oil.

$^1$H-NMR (CDCl$_3$, 400 MHz) δ:
0.94 (3H, t, J=7 Hz), 1.18 (3H, t, J=7 Hz), 1.34-1.47 (2H, m), 1.60-1.75 (2H, m), 2.32 (2H, q, J=7 Hz), 2.70 (2H, t, J=8 Hz), 3.96 (2H, s), 4.01 (3H, s), 7.29-7.38 (1H, m), 7.43-7.59 (3H, m), 7.76 (1H, d, J=8 Hz), 8.18 (1H, s), 8.54 (2H, s), 8.61 (1H, br s).

Example 4

Preparation of 5-{{6-[2-(1H-tetrazol-5-yl)phenyl]pyridin-3-yl}methyl}-6-butyl-3-(5-ethoxypyrimidin-2-yl)-2-ethylpyrimidin-4(3H)-one

[Chemical Formula 11]

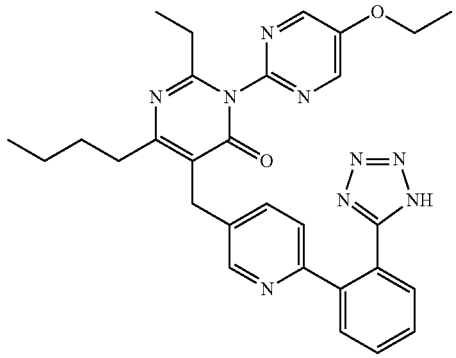

Process 1: By using 2-amino-5-ethoxypyrimidine instead of 2-amino-5-methoxypyrimidine in the Process 3 of the Example 1, the reaction and the treatment were performed in the same manner as the Process 3 of the Example 1 to give 2-{5-{[4-butyl-1-(5-ethoxypyrimidin-2-yl)-2-ethyl-6-oxo-1,6-dihydropyrimidin-5-yl]methyl}pyridin-2-yl}benzonitrile (yield: 80%) as a pale yellow solid.

$^1$H-NMR (CDCl$_3$, 400 MHz) δ:
0.94 (3H, t, J=7 Hz), 1.18 (3H, t, J=7 Hz), 1.37-1.47 (2H, m), 1.51 (3H, t, J=7 Hz), 1.62-1.72 (2H, m), 2.32 (2H, q, J=7 Hz), 2.66-2.72 (2H, m), 3.97 (2H, s), 4.22 (2H, q, J=7 Hz), 7.47 (1H, t, J=8 Hz), 7.64-7.69 (2H, m), 7.74-7.83 (3H, m), 8.51 (2H, s), 8.70 (1H, d, J=2 Hz).

Process 2: By using 2-{5-{[4-butyl-1-(5-ethoxypyrimidin-2-yl)-2-ethyl-6-oxo-1,6-dihydropyrimidin-5-yl]methyl}pyridin-2-yl}benzonitrile instead of 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of the Example 1, the reaction and the treatment were performed in the same manner as the Process 4 of the Example 1 to give 5-{{6-[2-(1H-tetrazol-5-yl)phenyl]pyridin-3-yl}methyl}-6-butyl-3-(5-ethoxypyrimidin-2-yl)-2-ethylpyrimidin-4(3H)-one (yield: 75%) as colorless viscous oil.

$^1$H-NMR (CDCl$_3$, 400 MHz) δ:
0.94 (3H, t, J=7 Hz), 1.18 (3H, t, J=7 Hz), 1.36-1.47 (2H, m), 1.51 (3H, t, J=7 Hz), 1.61-1.74 (2H, m), 2.33 (2H, q, J=7 Hz), 2.70 (2H, t, J=8 Hz), 3.97 (2H, s), 4.22 (2H, q, J=7 Hz), 7.38 (1H, d, J=8 Hz), 7.47-7.60 (3H, m), 7.78 (1H, dd, J=8, 2 Hz), 8.20-8.28 (1H, m), 8.51 (2H, s), 8.64 (1H, s).

Example 5

Preparation of 5-{{6-[2-(1H-tetrazol-5-yl)phenyl]pyridin-3-yl}methyl}-6-butyl-2-isopropyl-3-(5-methoxypyrimidin-2-yl)pyrimidin-4(3H)-one

[Chemical Formula 12]

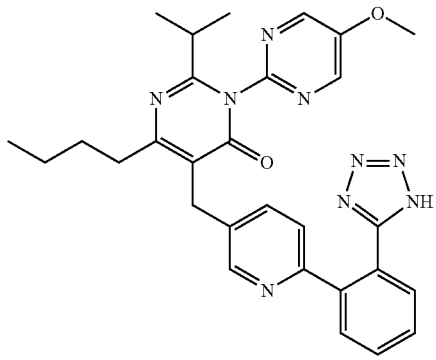

Process 1: By using isobutyryl chloride instead of propionyl chloride in the Process 1 of the Example 3, the reaction and the treatment were performed in the same manner as the Process 1 of the Example 3 to give methyl (Z)-2-{[6-(2-cyanophenyl)pyridin-3-yl]methyl}-3-isobutylamide-2-heptenoate (yield: 49%) as brown oil.

$^1$H-NMR (CDCl$_3$, 400 MHz) δ:
0.90 (3H, t, J=7 Hz), 1.25 (6H, d, J=7 Hz), 1.33-1.55 (4H, m), 2.49-2.63 (1H, m), 2.90-2.99 (2H, m), 3.71 (3H, s), 3.75 (2H, s), 7.49 (1H, td, J=8, 1 Hz), 7.59 (1H, dd, J=8, 2 Hz), 7.64-7.73 (2H, m), 7.79 (1H, dd, J=8, 1 Hz), 7.83 (1H, dd, J=8, 1 Hz), 8.61 (1H, d, J=1 Hz), 11.90 (1H, s).

Process 2: By using methyl (Z)-2-{[6-(2-cyanophenyl)pyridin-3-yl]methyl}-3-isobutylamide-2-heptenoate instead of methyl (Z)-3-acetamide-2-{[6-(2-cyanophenyl)pyridin-3-yl]methyl}-2-heptenoate in the Process 3 of the Example 1, the reaction and the treatment were performed in the same manner as the Process 3 of the Example 1 to give 2-{5-{[4-butyl-2-isopropyl-1-(5-methoxypyrimidin-2-yl)-6-oxo-1,6-dihydropyrimidin-5-yl]methyl}pyridin-2-yl}benzonitrile (yield: 55%) as yellow oil.

$^1$H-NMR (CDCl$_3$, 400 MHz) δ:
0.94 (3H, t, J=7 Hz), 1.20 (6H, d, J=7 Hz), 1.33-1.49 (2H, m), 1.62-1.75 (2H, m), 2.21-2.35 (1H, m), 2.69 (2H, t, J=8 Hz), 3.95 (2H, s), 4.00 (3H, s), 7.46 (1H, td, J=8, 1 Hz), 7.61-7.70 (2H, m), 7.74-7.83 (3H, m), 8.53 (2H, s), 8.69 (1H, d, J=1 Hz).

Process 3: By using 2-{5-{[4-butyl-2-isopropyl-1-(5-methoxypyrimidin-2-yl)-6-oxo-1,6-dihydropyrimidin-5-yl]methyl}pyridin-2-yl}benzonitrile instead of 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of the Example 1, the reaction and the treatment were performed in the same manner as the Process 4 of the Example 1 to give 5-{{6-[2-(1H-tetrazol-5-yl)phenyl]pyridin-3-yl}methyl}-6-butyl-2-isopropyl-3-(5-methoxypyrimidin-2-yl)pyrimidin-4(3H)-one (yield: 69%) as colorless viscous oil.

$^1$H-NMR (CDCl$_3$, 400 MHz) δ:
0.94 (3H, t, J=7 Hz), 1.20 (6H, d, J=7 Hz), 1.33-1.47 (2H, m), 1.60-1.75 (2H, m), 2.22-2.35 (1H, m), 2.70 (2H, t, J=8 Hz), 3.95 (2H, s), 4.01 (3H, s), 7.33 (1H, d, J=8 Hz), 7.45-7.57 (3H, m), 7.77 (1H, d, J=7 Hz), 8.18 (1H, br s), 8.53 (2H, s), 8.61 (1H, s).

Example 6

Preparation of 5-{{6-[2-(1H-tetrazol-5-yl)phenyl]pyridin-3-yl}methyl}-6-butyl-3-(5-ethoxypyrimidin-2-yl)-2-isopropylpyrimidin-4(3H)-one

[Chemical Formula 13]

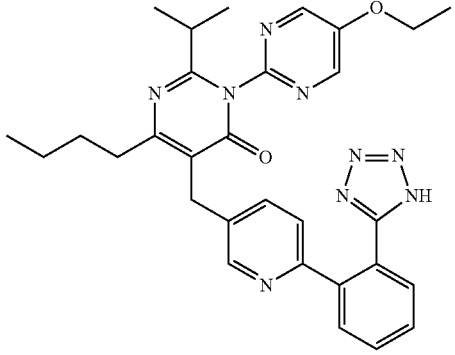

Process 1: By using methyl (Z)-2-{[6-(2-cyanophenyl)pyridin-3-yl]methyl}-3-isobutylamide-2-heptenoate obtained from the Process 1 of the Example 5 instead of methyl (Z)-3-acetamide-2-{[6-(2-cyanophenyl)pyridin-3-yl]methyl}-2-heptenoate in the Process 3 of the Example 1 and also using 2-amino-5-ethoxypyrimidine instead of 2-amino-5-methoxypyrimidine, the reaction and the treatment were performed in the same manner as the Process 3 of the Example 1 to give 2-{5-{[4-butyl-1-(5-ethoxypyrimidin-2-yl)-2-isopropyl-6-oxo-1,6-dihydropyrimidin-5-yl]methyl}pyridin-2-yl}benzonitrile (yield: 79%) as a pale yellow solid.

¹H-NMR (CDCl₃, 400 MHz) δ:
0.94 (3H, t, J=7 Hz), 1.19 (6H, d, J=7 Hz), 1.35-1.45 (2H, m), 1.51 (3H, t, J=7 Hz), 1.63-1.74 (2H, m), 2.22-2.35 (1H, m), 2.69 (2H, t, J=8 Hz), 3.95 (2H, s), 4.22 (2H, q, J=7 Hz), 7.46 (1H, td, J=8, 1 Hz), 7.62-7.70 (2H, m), 7.75-7.83 (3H, m), 8.50 (2H, s), 8.67-8.71 (1H, m).

Process 2: By using 2-{5-{[4-butyl-1-(5-ethoxypyrimidin-2-yl)-2-isopropyl-6-oxo-1,6-dihydropyrimidin-5-yl]methyl}pyridin-2-yl}benzonitrile instead of 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of the Example 1, the reaction and the treatment were performed in the same manner as the Process 4 of the Example 1 to give 5-{{6-[2-(1H-tetrazol-5-yl)phenyl]pyridin-3-yl}methyl}-6-butyl-3-(5-ethoxypyrimidin-2-yl)-2-isopropylpyrimidin-4(3H)-one (yield: 99%) as pale brown viscous oil.

¹H-NMR (CDCl₃, 400 MHz) δ:
0.94 (3H, t, J=7 Hz), 1.20 (6H, d, J=7 Hz), 1.35-1.46 (2H, m), 1.51 (3H, t, J=7 Hz), 1.63-1.75 (2H, m), 2.22-2.35 (1H, m), 2.71 (2H, t, J=7 Hz), 3.96 (2H, s), 4.22 (2H, q, J=7 Hz), 7.37-7.45 (1H, m), 7.48-7.63 (3H, m), 7.81 (1H, dd, J=8, 2 Hz), 8.25-8.33 (1H, m), 8.51 (2H, s), 8.67 (1H, s).

Example 7

Preparation of 5-{{6-[2-(1H-tetrazol-5-yl)phenyl]pyridin-3-yl}methyl}-6-butyl-2-cyclopropyl-3-(5-methoxypyrimidin-2-yl)pyrimidin-4(3H)-one

[Chemical Formula 14]

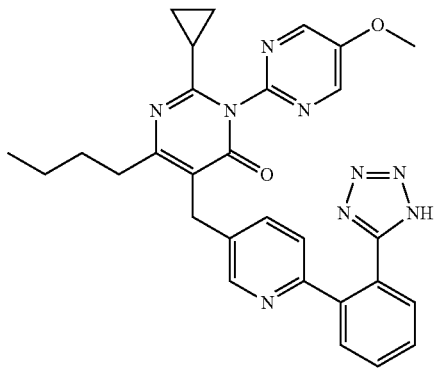

Process 1: By using cyclopropanecarbonyl chloride instead of propionyl chloride in the Process 1 of the Example 3, the reaction and the treatment were performed in the same manner as the Process 1 of the Example 3 to give methyl (Z)-2-{[6-(2-cyanophenyl)pyridin-3-yl]methyl}-3-(cyclopropanecarboxamide)-2-heptenoate (yield: 69%) as yellow oil.

¹H-NMR (CDCl₃, 400 MHz) δ:
0.78-0.98 (5H, m), 1.02-1.12 (2H, m), 1.31-1.65 (5H, m), 2.88-3.02 (2H, m), 3.72 (3H, s), 3.76 (2H, s), 7.50 (1H, t, J=8 Hz), 7.60 (1H, d, J=8 Hz), 7.63-7.74 (2H, m), 7.76-7.87 (2H, m), 8.61 (1H, s), 12.2 (1H, s).

Process 2: By using methyl (Z)-2-{[6-(2-cyanophenyl)pyridin-3-yl]methyl}-3-(cyclopropanecarboxamide)-2-heptenoate instead of methyl (Z)-3-acetamide-2-{[6-(2-cyanophenyl)pyridin-3-yl]methyl}-2-heptenoate in the Process 3 of the Example 1, the reaction and the treatment were performed in the same manner as the Process 3 of the Example 1 to give 2-{5-{[4-butyl-2-cyclopropyl-1-(5-methoxypyrimidin-2-yl)-6-oxo-1,6-dihydropyrimidin-5-yl]methyl}pyridin-2-yl}benzonitrile (yield: 63%) as yellow oil.

¹H-NMR (CDCl₃, 400 MHz) δ:
0.82-0.87 (2H, m), 0.92 (3H, t, J=7 Hz), 1.07-1.15 (1H, m), 1.21-1.27 (2H, m), 1.32-1.41 (2H, m), 1.53-1.64 (2H, m), 2.61 (2H, t, J=8 Hz), 3.94 (2H, s), 4.01 (3H, s), 7.44-7.49 (1H, m), 7.66 (2H, t, J=8 Hz), 7.74-7.82 (3H, m), 8.56 (2H, s), 8.68 (1H, d, J=2 Hz).

Process 3: By using 2-{5-{[4-butyl-2-cyclopropyl-1-(5-methoxypyrimidin-2-yl)-6-oxo-1,6-dihydropyrimidin-5-yl]methyl}pyridin-2-yl}benzonitrile instead of 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of the Example 1, the reaction and the treatment were performed in the same manner as the Process 4 of the Example 1 to give 5-{{6-[2-(1H-tetrazol-5-yl)phenyl]pyridin-3-yl}methyl}-6-butyl-2-cyclopropyl-3-(5-methoxypyrimidin-2-yl)pyrimidin-4(3H)-one (yield: 100%) as pale yellow viscous oil.

¹H-NMR (CDCl₃, 400 MHz) δ:
0.82-0.89 (2H, m), 0.92 (3H, t, J=7 Hz), 1.06-1.15 (1H, m), 1.21-1.27 (2H, m), 1.31-1.43 (2H, m), 1.56-1.67 (2H, m), 2.63 (2H, t, J=8 Hz), 3.94 (2H, s), 4.01 (3H, s), 7.40 (1H, d, J=8 Hz), 7.47-7.62 (3H, m), 7.75-7.82 (1H, m), 8.23-8.32 (1H, m), 8.56 (2H, s), 8.65 (1H, s).

Example 8

Preparation of 5-{{6-[2-(1H-tetrazol-5-yl)phenyl]pyridin-3-yl}methyl}-6-butyl-2-cyclobutyl-3-(5-methoxypyrimidin-2-yl)pyrimidin-4(3H)-one

[Chemical Formula 15]

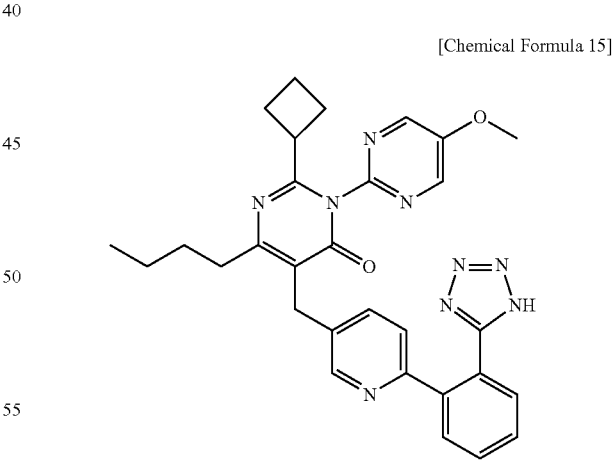

Process 1: By using cyclobutanecarbonyl chloride instead of propionyl chloride in the Process 1 of the Example 3, the reaction and the treatment were performed in the same manner as the Process 1 of the Example 3 to give methyl (Z)-2-{[6-(2-cyanophenyl)pyridin-3-yl]methyl}-3-(cyclobutanecarboxamide)-2-heptenoate (yield: 72%) as brown oil.

¹H-NMR (CDCl₃, 400 MHz) δ:
0.91 (3H, t, J=7 Hz), 1.33-1.54 (4H, m), 2.19-2.44 (6H, m), 2.95 (2H, t, J=8 Hz), 3.12-3.25 (1H, m), 3.70 (3H, s), 3.75

(2H, s), 7.49 (1H, td, J=8, 1 Hz), 7.58 (1H, dd, J=8, 2 Hz), 7.64-7.73 (2H, m), 7.76-7.86 (2H, m), 8.60 (1H, s), 11.78 (1H, s).

Process 2: By using methyl (Z)-2-{[6-(2-cyanophenyl)pyridin-3-yl]methyl}-3-(cyclobutanecarboxamide)-2-heptenoate instead of methyl (Z)-3-acetamide-2-{[6-(2-cyanophenyl)pyridin-3-yl]methyl}-2-heptenoate in the Process 3 of the Example 1, the reaction and the treatment were performed in the same manner as the Process 3 of the Example 1 to give 2-{5-{[4-butyl-2-cyclobutyl-1-(5-methoxypyrimidin-2-yl)-6-oxo-1,6-dihydropyrimidin-5-yl]methyl}pyridin-2-yl}benzonitrile (yield: 65%) as a pale yellow solid.

$^1$H-NMR (CDCl$_3$, 400 MHz) δ:
0.96 (3H, t, J=7 Hz), 1.34-1.51 (2H, m), 1.65-1.83 (6H, m), 2.36-2.51 (2H, m), 2.71 (2H, t, J=8 Hz), 3.07-3.17 (1H, m), 3.96 (2H, s), 4.00 (3H, s), 7.46 (1H, td, J=8, 1 Hz), 7.61-7.70 (2H, m), 7.73-7.82 (3H, m), 8.52 (2H, s), 8.69 (1H, d, J=1 Hz).

Process 3: By using 2-{5-{[4-butyl-2-cyclobutyl-1-(5-methoxypyrimidin-2-yl)-6-oxo-1,6-dihydropyrimidin-5-yl]methyl}pyridin-2-yl}benzonitrile instead of 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of the Example 1, the reaction and the treatment were performed in the same manner as the Process 4 of the Example 1 to give 5-{{6-[2-(1H-tetrazol-5-yl)phenyl]pyridin-3-yl}methyl}-6-butyl-2-cyclobutyl-3-(5-methoxypyrimidin-2-yl)pyrimidin-4(3H)-one (yield: 74%) as colorless viscous oil.

$^1$H-NMR (CDCl$_3$, 400 MHz) δ:
0.95 (3H, t, J=7 Hz), 1.34-1.50 (2H, m), 1.65-1.83 (6H, m), 2.37-2.51 (2H, m), 2.72 (2H, t, J=8 Hz), 3.04-3.20 (1H, m), 3.96 (2H, s), 4.01 (3H, s), 7.31 (1H, d, J=8 Hz), 7.45-7.56 (3H, m), 7.76 (1H, d, J=8 Hz), 8.16 (1H, br s), 8.52 (2H, s), 8.59 (1H, s).

Example 9

Preparation of 5-{{6-[2-(1H-tetrazol-5-yl)phenyl]pyridin-3-yl}methyl}-6-butyl-2-cyclobutyl-3-(5-ethoxypyrimidin-2-yl)pyrimidin-4(3H)-one

[Chemical Formula 16]

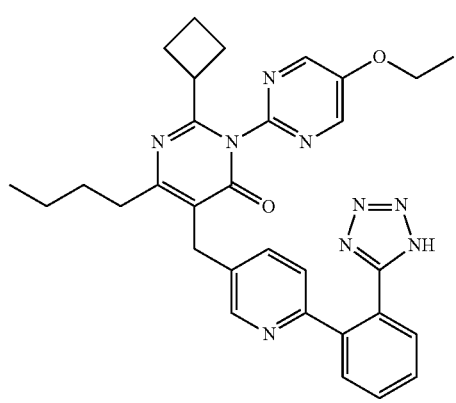

Process 1: By using methyl (Z)-2-{[6-(2-cyanophenyl)pyridin-3-yl]methyl}-3-(cyclobutanecarboxamide)-2-heptenoate obtained from the Process 1 of the Example 8 instead of methyl (Z)-3-acetamide-2-{[6-(2-cyanophenyl)pyridin-3-yl]methyl}-2-heptenoate in the Process 3 of the Example 1 and also using 2-amino-5-ethoxypyrimidine instead of 2-amino-5-methoxypyrimidine, the reaction and the treatment were performed in the same manner as the Process 3 of the Example 1 to give 2-{5-{[4-butyl-2-cyclobutyl-1-(5-ethoxypyrimidin-2-yl)-6-oxo-1,6-dihydropyrimidin-5-yl]methyl}pyridin-2-yl}benzonitrile (yield: 89%) as a pale yellow solid.

$^1$H-NMR (CDCl$_3$, 400 MHz) δ:
0.96 (3H, t, J=7 Hz), 1.39-1.47 (2H, m), 1.51 (3H, t, J=7 Hz), 1.61-1.84 (6H, m), 2.36-2.51 (2H, m), 2.67-2.75 (2H, m), 3.03-3.16 (1H, m), 3.96 (2H, s), 4.22 (2H, q, J=7 Hz), 7.48 (1H, dd, J=8, 1 Hz), 7.62-7.70 (2H, m), 7.72-7.83 (3H, m), 8.49 (2H, s), 8.69 (1H, d, J=2 Hz).

Process 2: By using 2-{5-{[4-butyl-2-cyclobutyl-1-(5-ethoxypyrimidin-2-yl)-6-oxo-1,6-dihydropyrimidin-5-yl]methyl}pyridin-2-yl}benzonitrile instead of 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of the Example 1, the reaction and the treatment were performed in the same manner as the Process 4 of the Example 1 to give 5-{{6-[2-(1H-tetrazol-5-yl)phenyl]pyridin-3-yl}methyl}-6-butyl-2-cyclobutyl-3-(5-ethoxypyrimidin-2-yl)pyrimidin-4(3H)-one (yield: 99%) as pale brown viscous oil.

$^1$H-NMR (CDCl$_3$, 400 MHz) δ:
0.95 (3H, t, J=7 Hz), 1.36-1.47 (2H, m), 1.51 (3H, t, J=7 Hz), 1.63-1.85 (6H, m), 2.37-2.50 (2H, m), 2.73 (2H, t, J=8 Hz), 3.07-3.18 (1H, m), 3.97 (2H, s), 4.22 (2H, q, J=7 Hz), 7.40 (1H, d, J=8 Hz), 7.48-7.62 (3H, m), 7.76-7.82 (1H, m), 8.24-8.31 (1H, m), 8.49 (2H, s), 8.66 (1H, s).

Example 10

Preparation of 5-{{6-[2-(1H-tetrazol-5-yl)phenyl]pyridin-3-yl}methyl}-6-butyl-2-cyclopentyl-3-(5-ethoxypyrimidin-2-yl)pyrimidin-2-pyrimidin-4(3H)-one

[Chemical Formula 17]

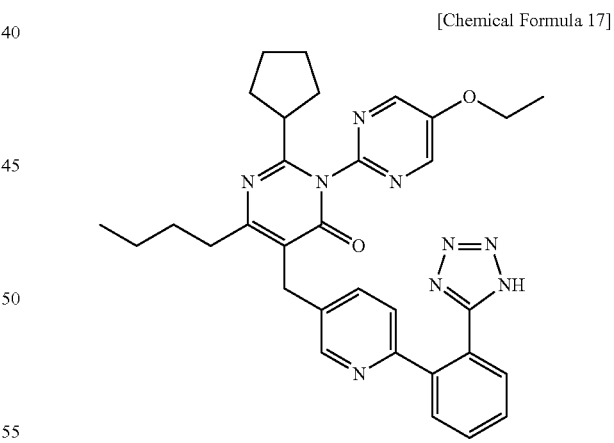

Process 1: By using cyclopentanecarbonyl chloride instead of propionylchloride in the Process 1 of the Example 3, the reaction and the treatment were performed in the same manner as the Process 1 of the Example 3 to give methyl (Z)-2-{[6-(2-cyanophenyl)pyridin-3-yl]methyl}-3-(cyclopentanecarboxamide)-2-heptenoate (yield: 44%) as brown oil.

$^1$H-NMR (CDCl$_3$, 400 MHz) δ:
0.90 (3H, t, J=7 Hz), 1.33-2.03 (12H, m), 2.70-2.82 (1H, m), 2.89-2.99 (2H, m), 3.71 (3H, s), 3.75 (2H, s), 7.49 (1H, td, J=8, 1 Hz), 7.59 (1H, dd, J=8, 2 Hz), 7.64-7.73 (2H, m), 7.76-7.86 (2H, m), 8.60 (1H, s), 11.89 (1H, s).

Process 2: By using methyl (Z)-2-{[6-(2-cyanophenyl)pyridin-3-yl]methyl}-3-(cyclopentanecarboxamide)-2-heptenoate instead of methyl (Z)-3-acetamide-2-{[6-(2-cyanophenyl)pyridin-3-yl]methyl}-2-heptenoate in the Process 3 of the Example 1 and also using 2-amino-5-ethoxypyrimidine instead of 2-amino-5-methoxypyrimidine, the reaction and the treatment were performed in the same manner as the Process 3 of the Example 1 to give 2-{5-{[4-butyl-2-cyclopentyl-1-(5-ethoxypyrimidin-2-yl)-6-oxo-1,6-dihydropyrimidin-5-yl]methyl}pyridin-2-yl}benzonitrile (yield: 57%) as a pale yellow solid.

$^1$H-NMR (CDCl$_3$, 400 MHz) δ:
0.94 (3H, t, J=7 Hz), 1.34-1.54 (7H, m), 1.60-1.80 (6H, m), 1.90-2.03 (2H, m), 2.42-2.48 (1H, m), 2.64-2.70 (2H, m), 3.95 (2H, s), 4.22 (2H, q, J=7 Hz), 7.47 (1H, td, J=8, 1 Hz), 7.63-7.69 (2H, m), 7.77 (2H, dd, J=8, 1 Hz), 7.80 (1H, dd, J=8, 1 Hz), 8.51 (2H, s), 8.69 (1H, d, J=2 Hz).

Process 3: By using 2-{5-{[4-butyl-2-cyclopentyl-1-(5-ethoxypyrimidin-2-yl)-6-oxo-1,6-dihydropyrimidin-5-yl]methyl}pyridin-2-yl}benzonitrile instead of 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of the Example 1, the reaction and the treatment were performed in the same manner as the Process 4 of the Example 1 to give 5-{{6-[2-(1H-tetrazol-5-yl)phenyl]pyridin-3-yl}methyl}-6-butyl-2-cyclopentyl-3-(5-ethoxypyrimidin-2-yl)pyrimidin-4(3H)-one (yield: 40%) as pale yellow amorphous.

$^1$H-NMR (CDCl$_3$, 400 MHz) δ:
0.94 (3H, t, J=7 Hz), 1.52 (3H, t, J=7 Hz), 1.57-1.78 (8H, m), 1.81-1.93 (5H, m), 2.70 (2H, t, J=8 Hz), 3.94 (2H, s), 4.23 (2H, q, J=7 Hz), 7.38 (1H, d, J=9 Hz), 7.47-7.62 (3H, m), 7.78 (1H, d, J=8 Hz), 8.22-8.29 (1H, m), 8.52 (2H, s), 8.65 (1H, s).

Example 11

Preparation of 5-{{6-[2-(1H-tetrazol-5-yl)phenyl]pyridin-3-yl}methyl}-6-butyl-2-cyclohexyl-3-(5-ethoxypyrimidin-2-yl)pyrimidin-4(3H)-one

[Chemical Formula 18]

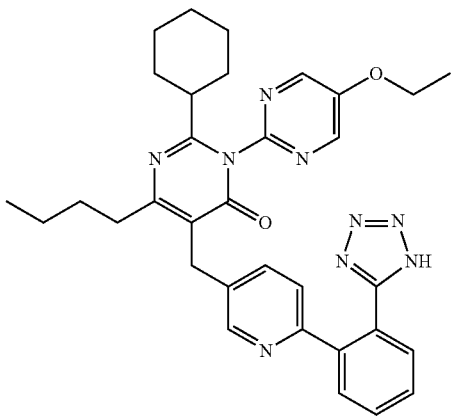

Process 1: By using cyclohexanecarbonyl chloride instead of propionyl chloride in the Process 1 of the Example 3, the reaction and the treatment were performed in the same manner as the Process 1 of the Example 3 to give methyl (Z)-2-{[6-(2-cyanophenyl)pyridin-3-yl]methyl}-3-(cyclohexanecarboxamide)-2-heptenoate (yield: 52%) as brown oil.

$^1$H-NMR (CDCl$_3$, 400 MHz) δ:
0.90 (3H, t, J=7 Hz), 1.16-2.03 (14H, m), 2.45-2.59 (1H, m), 2.89-2.98 (2H, m), 3.71 (3H, s), 3.75 (2H, s), 7.49 (2H, td, J=8, 1 Hz), 7.58 (1H, dd, J=8, 2 Hz), 7.63-7.74 (2H, m), 7.76-7.86 (2H, m), 8.61 (1H, s), 11.84 (1H, br s).

Process 2: By using methyl (Z)-2-{[6-(2-cyanophenyl)pyridin-3-yl]methyl}-3-(cyclohexanecarboxamide)-2-heptenoate instead of methyl (Z)-3-acetamide-2-{[6-(2-cyanophenyl)pyridin-3-yl]methyl}-2-heptenoate in the Process 3 of the Example 1 and also using 2-amino 5-ethoxypyrimidine instead of 2-amino 5-methoxypyrimidine, the reaction and the treatment were performed in the same manner as the Process 3 of the Example 1 to give 2-{5-{[4-butyl-2-cyclohexyl-1-(5-ethoxypyrimidin-2-yl)-6-oxo-1,6-dihydropyrimidin-5-yl]methyl}pyridin-2-yl}benzonitrile (yield: 80%) as a pale yellow solid.

$^1$H-NMR (CDCl$_3$, 400 MHz) δ:
0.94 (3H, t, J=7 Hz), 1.16-1.91 (17H, m), 2.65-2.71 (2H, m), 3.95 (2H, s), 4.23 (2H, q, J=7 Hz), 7.47 (1H, td, J=8, 1 Hz), 7.63-7.68 (2H, m), 7.75-7.82 (3H, m), 8.51 (2H, s), 8.69 (1H, d, J=1 Hz).

Process 3: By using 2-{5-{[4-butyl-2-cyclohexyl-1-(5-ethoxypyrimidin-2-yl)-6-oxo-1,6-dihydropyrimidin-5-yl]methyl}pyridin-2-yl}benzonitrile instead of 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of the Example 1, the reaction and the treatment were performed in the same manner as the Process 4 of the Example 1 to give 5-{{6-[2-(1H-tetrazol-5-yl)phenyl]pyridin-3-yl}methyl}-6-butyl-2-cyclohexyl-3-(5-ethoxypyrimidin-2-yl)pyrimidin-4(3H)-one (yield: 58%) as colorless viscous oil.

$^1$H-NMR (CDCl$_3$, 400 MHz) δ:
0.94 (3H, t, J=7 Hz), 1.51 (3H, t, J=7 Hz), 1.61-1.82 (8H, m), 1.90-2.05 (5H, m), 2.46 (2H, t, J=8 Hz), 2.69 (2H, t, J=7 Hz), 3.95 (2H, s), 4.22 (2H, q, J=7 Hz), 7.39 (1H, d, J=8 Hz), 7.48-7.62 (3H, m), 7.79 (1H, dd, J=8, 2 Hz), 8.22-8.31 (1H, m), 8.51 (2H, s), 8.65 (1H, s).

Example 12

Preparation of 5-{{6-[2-(1H-tetrazol-5-yl)phenyl]pyridin-3-yl}methyl}-6-butyl-2-methyl-3-{5-[2-(methylthio)ethoxy]pyrimidin-2-yl}pyrimidin-4(3H)-one

[Chemical Formula 19]

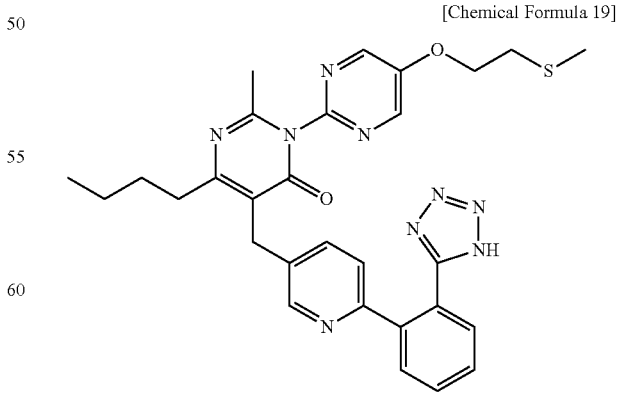

Process 1: By using 2-amino-5-[2-(methylthio)ethoxy]pyrimidine instead of 2-amino-5-methoxypyrimidine in the Process 3 of the Example 1, the reaction and the treatment were performed in the same manner as the Process 3 of the Example 1 to give 2-{5-{{4-butyl-2-methyl-1-{5-[2-(methylthio)ethoxy]pyrimidin-2-yl}-6-oxo-1,6-dihydropyrimidin-5-yl}methyl}pyridin-2-yl}benzonitrile (yield: 64%) as yellow oil.

¹H-NMR (CDCl₃, 400 MHz) δ:
0.95 (3H, t, J=7 Hz), 1.33-1.48 (2H, m), 1.57-1.73 (2H, m), 2.17 (3H, s), 2.24 (3H, s), 2.67 (2H, t, J=8 Hz), 2.96 (2H, t, J=7 Hz), 3.97 (2H, s), 4.33 (2H, t, J=7 Hz), 7.47 (1H, t, J=8 Hz), 7.62-7.70 (2H, m), 7.73-7.83 (3H, m), 8.55 (2H, s), 8.70 (1H, s).

Process 2: By using 2-{5-{{4-butyl-2-methyl-1-{5-[2-(methylthio)ethoxy]pyrimidin-2-yl}-6-oxo-1,6-dihydropyrimidin-5-yl}methyl}pyridin-2-yl}benzonitrile instead of 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of the Example 1, the reaction and the treatment were performed in the same manner as the Process 4 of the Example 1 to give 5-{{6-[2-(1H-tetrazol-5-yl)phenyl]pyridin-3-yl}methyl}-6-butyl-2-methyl-3-{5-[2-(methylthio)ethoxy]pyrimidin-2-yl}pyrimidin-4(3H)-one (yield: 80%) as yellow oil.

¹H-NMR (CDCl₃, 400 MHz) δ:
0.82-1.00 (3H, m), 1.33-1.47 (2H, m), 1.55-1.73 (2H, m), 2.15 (3H, s), 2.23 (3H, s), 2.55-2.76 (2H, m), 2.95 (2H, t, J=7 Hz), 3.82-4.03 (2H, m), 4.33 (2H, t, J=7 Hz), 7.07-7.33 (1H, m), 7.35-7.57 (3H, m), 7.59-7.80 (1H, m), 7.85-8.15 (1H, m), 8.47-8.62 (1H, m), 8.55 (2H, s).

Example 13

Preparation of 5-{{6-[2-(1H-tetrazol-5-yl)phenyl]pyridin-3-yl}methyl}-6-butyl-2-methyl-3-{5-[2-(methylsulfonyl)ethoxy]pyrimidin-2-yl}pyrimidin-4(3H)-one

[Chemical Formula 20]

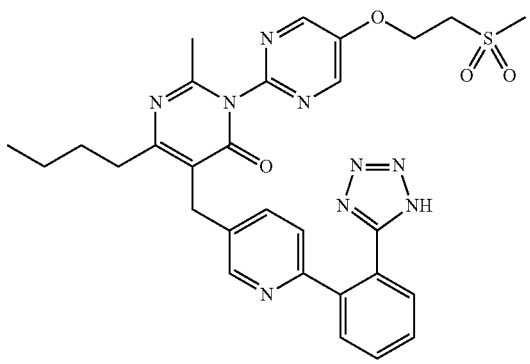

Methanol 0.4 mL) solution of hydrogen peroxide (30% solution, 24 mg, 0.211 mmol) and methanol (0.4 mL) solution of tantalum chloride (1.5 mg, 0.0042 mmol) were added to methanol (1.0 mL) solution of 5-{{6-[2-(1H-tetrazol-5-yl)phenyl]pyridin-3-yl}methyl}-6-butyl-2-methyl-3-{5-[2-(methylthio)ethoxy]pyrimidin-2-yl}pyrimidin-4(3H)-one (24 mg, 0.042 mmol) which has been obtained in the Example 12. After stirring for 12 hours at room temperature, the solvent was removed by distillation. The obtained residues were subjected to silica gel column chromatography (chloroform:methanol:triethylamine=4:1:0.4) to give 5-{{6-[2-(1H-tetrazol-5-yl)phenyl]pyridin-3-yl}methyl}-6-butyl-2-methyl-3-{5-[2-(methylsulfonyl)ethoxy]pyrimidin-2-yl}pyrimidin-4(3H)-one (24 mg, 93%) as pale yellow amorphous.

¹H-NMR (CDCl₃, 400 MHz) δ:
0.94 (3H, t, J=7 Hz), 1.34-1.47 (2H, m), 1.54-1.71 (2H, m), 2.16 (3H, s), 2.66 (2H, t, J=8 Hz), 3.09 (3H, s), 3.55 (2H, t, J=5 Hz), 3.93 (2H, s), 4.64 (2H, t, J=5 Hz), 7.10-7.24 (1H, m), 7.31-7.55 (3H, m), 7.65-7.77 (1H, m), 7.92-8.04 (1H, m), 8.45-8.53 (1H, m), 8.59 (2H, s).

Example 14

Preparation of 3-{2-{5-{[4-butyl-2-methyl-6-oxo-1-(pyridin-2-yl)-1,6-dihydropyrimidin-5-yl]methyl}pyridin-2-yl}phenyl}-1,2,4-oxadiazol-5(4H)-one

[Chemical Formula 21]

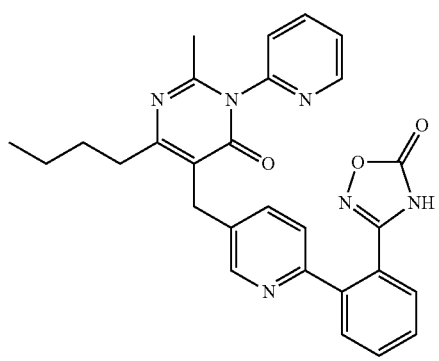

Process 1: By using 2-amino-pyridine instead of 2-amino-5-methoxypyrimidine in the Process 3 of the Example 1, the reaction and the treatment were performed in the same manner as the Process 3 of the Example 1 to give 2-{5-{[4-butyl-2-methyl-6-oxo-1-(pyridin-2-yl)-1,6-dihydropyrimidin-5-yl]methyl}pyridin-2-yl}benzonitrile (yield: 61%).

¹H-NMR (CDCl₃, 400 MHz) δ:
0.95 (3H, t, J=7 Hz), 1.43 (2H, sextet, J=8 Hz), 1.61-1.69 (2H, m), 2.17 (3H, s), 2.66-2.70 (2H, m), 3.97 (2H, s), 7.36-7.50 (3H, m), 7.65-7.69 (2H, m), 7.76-7.81 (3H, m), 7.93 (1H, m), 8.67-8.70 (2H, m).

Process 2: Sodium hydrogen carbonate (2.02 mg, 24.0 mmol) was added to dimethyl sulfoxide solution (20 mL) of hydroxylamine hydrochloride (1.42 g, 20.4 mmol) and stirred for 1 hour at 40° C. Dimethyl sulfoxide solution (3 mL) of 2-{5-{[4-butyl-2-methyl-6-oxo-1-(pyridin-2-yl)-1,6-dihydropyrimidin-5-yl]methyl}pyridin-2-yl}benzonitrile (430 mg, 0.987 mmol) was added to the reaction mixture and stirred for 19 hours at 90° C. The reaction mixture was added water and extracted with ethyl acetate. The organic layer was combined, washed with water and brine, dried over anhydrous sodium sulfate, and concentrated in vacuo. The obtained residues were subjected to silica gel column chromatography (ethyl acetate) to give 2-{5-{[4-butyl-2-methyl-6-oxo-1-(pyridin-2-yl)-1,6-dihydropyrimidin-5-yl]methyl}pyridin-2-yl}-N'-hydroxybenzimidamide (430 mg, 93%) as a white solid.

Process 3: 1,1'-Carbonyldiimidazole (490 mg, 3.02 mmol) and 1,8-diazabicyclo[5.4.0]undec-7-ene (460 mg, 3.02 mmol) were added to dimethylformamide solution (25 mL) of 2-{5-{[4-butyl-2-methyl-6-oxo-1-(pyridin-2-yl)-1,6-dihydropyrimidin-5-yl]methyl}pyridin-2-yl}-N'-hydroxybenzimidamide (430 mg, 0.918 mmol) and stirred for 3 hours at room temperature. Once the reaction is completed, the reaction mixture was added water and extracted with ethyl acetate. The organic layer was combined, washed with water and brine, dried over anhydrous sodium sulfate, and concentrated in vacuo. The obtained residues were purified by silica gel column chromatography (ethyl acetate) to give 3-{2-{5-{[4-butyl-2-methyl-6-oxo-1-(pyridin-2-yl)-1,6-dihydropyrimidin-5-yl]methyl}pyridin-2-yl}phenyl}-1,2,4-oxadiazol-5(4H)-one (160 mg, 35%, two step yield) as weak yellow oil.

$^1$H-NMR (CDCl$_3$, 400 MHz) δ:

0.94 (3H, t, J=7 Hz), 1.42 (2H, sextet, J=8 Hz), 1.60-1.68 (2H, m), 2.17 (3H, s), 2.64-2.68 (2H, m), 3.93 (2H, s), 7.33-7.56 (6H, m), 7.74-7.77 (2H, m), 7.95 (1H, dd, J=8, 2 Hz), 8.45 (1H, s), 8.67 (1H, d, J=4 Hz).

Example 15

Preparation of 3-{2-{5-{[4-butyl-2-methyl-1-(4-methylpyridin-2-yl)-6-oxo-1,6-dihydropyrimidin-5-yl]methyl}pyridin-2-yl}phenyl}-1,2,4-oxadiazol-5(4H)-one

[Chemical Formula 22]

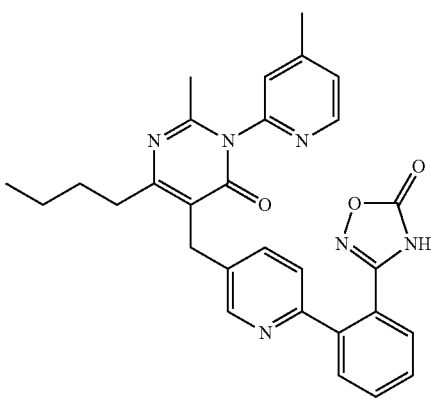

Process 1: By using 2-amino-4-methylpyridine instead of 2-amino-5-methoxypyrimidine in the Process 3 of the Example 1, the reaction and the treatment were performed in the same manner as the Process 3 of the Example 1 to give 2-{5-{[4-butyl-2-methyl-1-(4-methylpyridin-2-yl)-6-oxo-1,6-dihydropyrimidin-5-yl]methyl}pyridin-2-yl}benzonitrile (yield: 61%).

$^1$H-NMR (CDCl$_3$, 400 MHz) δ:

0.95 (3H, t, J=7 Hz), 1.42 (2H, sextet, J=8 Hz), 1.60-1.69 (2H, m), 2.17 (3H, s), 2.45 (3H, s), 2.66-2.70 (2H, m), 3.96 (2H, s), 7.19 (1H, s), 7.24-7.27 (2H, m), 7.48 (1H, m), 7.65-7.69 (2H, m), 7.76-7.82 (2H, m), 8.51 (1H, d, J=5 Hz), 8.70 (1H, s).

Process 2: By using 2-{5-{[4-butyl-2-methyl-1-(4-methylpyridin-2-yl)-6-oxo-1,6-dihydropyrimidin-5-yl]methyl}pyridin-2-yl}benzonitrile instead of 2-{5-{[4-butyl-2-methyl-6-oxo-1-(pyridin-2-yl)-1,6-dihydropyrimidin-5-yl]methyl}pyridin-2-yl}benzonitrile in the Process 2 of the Example 14, the reaction and the treatment were performed in the same manner as the Process 2 of the Example 14 to give 2-{5-{[4-butyl-2-methyl-1-(4-methylpyridin-2-yl)-6-oxo-1,6-dihydropyrimidin-5-yl]methyl}pyridin-2-yl}-N'-hydroxybenzimidamide.

Process 3: By using 2-{5-{[4-butyl-2-methyl-1-(4-methylpyridin-2-yl)-6-oxo-1,6-dihydropyrimidin-5-yl]methyl}pyridin-2-yl}-N'-hydroxybenzimidamide instead of 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of the Example 14, the reaction and the treatment were performed in the same manner as the Process 3 of the Example 14 to give 3-{2-{5-{[4-butyl-2-methyl-1-(4-methylpyridin-2-yl)-6-oxo-1,6-dihydropyrimidin-5-yl]methyl}pyridin-2-yl}phenyl}-1,2,4-oxadiazol-5(4H)-one (yield: 45%, two step yield) as weak yellow oil.

$^1$H-NMR (CDCl$_3$, 400 MHz) δ:

0.95 (3H, t, J=7 Hz), 1.42 (2H, sextet, J=8 Hz), 1.61-1.69 (2H, m), 2.17 (3H, s), 2.46 (3H, s), 2.65-2.69 (2H, m), 3.94 (2H, s), 7.21 (1H, s), 7.24-7.28 (2H, m), 7.37-7.60 (3H, m), 7.78 (1H, dd, J=8, 2 Hz), 7.85 (1H, d, J=7 Hz), 8.50-8.51 (2H, m).

Example 16

Preparation of 3-{2-{5-{[4-butyl-1-(5-methoxypyrimidin-2-yl)-2-methyl-6-oxo-1,6-dihydropyrimidin-5-yl]methyl}pyridin-2-yl}phenyl}-1,2,4-oxadiazol-5(4H)-one

[Chemical Formula 23]

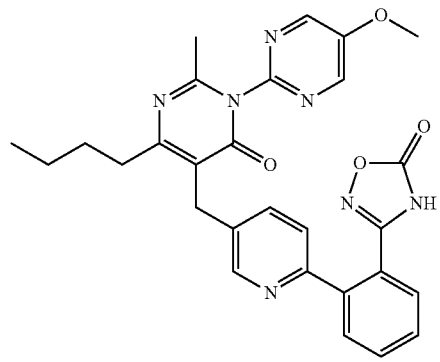

Process 1: By using 2-{5-{[4-butyl-1-(5-methoxypyrimidin-2-yl)-2-methyl-6-oxo-1,6-dihydropyrimidin-5-yl]methyl}pyridin-2-yl}benzonitrile obtained from the Process 3 of the Example 1 instead of 2-{5-{[4-butyl-2-methyl-6-oxo-1-(pyridin-2-yl)-1,6-dihydropyrimidin-5-yl]methyl}pyridin-2-yl}benzonitrile in the Process 2 of the Example 14, the reaction and the treatment were performed in the same manner as the Process 2 of the Example 14 to give 2-{5-{[4-butyl-1-(5-methoxypyrimidin-2-yl)-2-methyl-6-oxo-1,6-dihydropyrimidin-5-yl]methyl}pyridin-2-yl}-N'-hydroxybenzimidamide.

Process 2: By using 2-{5-{[4-butyl-1-(5-methoxypyrimidin-2-yl)-2-methyl-6-oxo-1,6-dihydropyrimidin-5-yl]methyl}pyridin-2-yl}-N'-hydroxybenzimidamide instead of 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of the Example 14, the reaction and the treatment were performed in the same manner as the Process 3 of the Example 14 to give 3-{2-{5-{[4-butyl-1-(5-methoxypyrimidin-2-yl)-2-methyl-6-oxo-1,6-dihydropyrimidin-5-yl]methyl}pyridin-2-yl}phenyl}-1,2,4-oxadiazol-5(4H)-one (yield: 48%, two step yield) as colorless amorphous.

¹H-NMR (CDCl₃, 400 MHz) δ:

0.94 (3H, t, J=7 Hz), 1.43 (2H, quint, J=8 Hz), 1.61-1.68 (2H, m), 2.17 (3H, s), 2.65-2.69 (2H, m), 3.95 (2H, s), 4.01 (3H, s), 7.36-7.69 (4H, m), 7.76-7.86 (2H, m), 8.51 (1H, br), 8.54 (2H, s).

Example 17

Preparation of 3-{2-{5-{[4-butyl-1-(5-ethoxypyrimidin-2-yl)-2-methyl-6-oxo-1,6-dihydropyrimidin-5-yl]methyl}pyridin-2-yl}phenyl}-1,2,4-oxadiazol-5(4H)-one

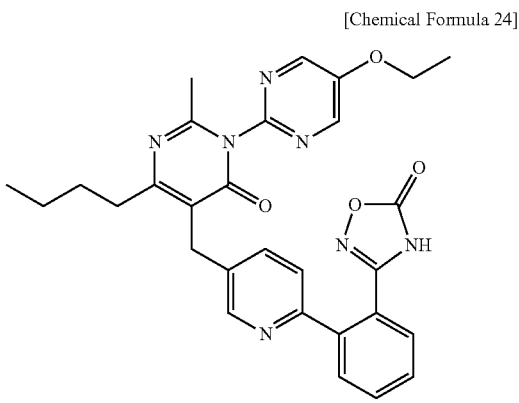 [SMILES: CCCCc1nc(C)n(-c2ncc(OCC)cn2)c(=O)c1Cc1ccc(-c2ccccc2-c2noc(=O)[nH]2)nc1]

[Chemical Formula 24]

Process 1: By using 2-{5-{[4-butyl-1-(5-ethoxypyrimidin-2-yl)-2-methyl-6-oxo-1,6-dihydropyrimidin-5-yl]methyl}pyridin-2-yl}benzonitrile obtained from the Process 1 of the Example 2 instead of 2-{5-{[4-butyl-2-methyl-6-oxo-1-(pyridin-2-yl)-1,6-dihydropyrimidin-5-yl]methyl}pyridin-2-yl}benzonitrile in the Process 2 of the Example 14, the reaction and the treatment were performed in the same manner as the Process 2 of the Example 14 to give 2-{5-{[4-butyl-1-(5-ethoxypyrimidin-2-yl)-2-methyl-6-oxo-1,6-dihydropyrimidin-5-yl]methyl}pyridin-2-yl}-N'-hydroxybenzimidamide.

Process 2: By using 2-{5-{[4-butyl-1-(5-ethoxypyrimidin-2-yl)-2-methyl-6-oxo-1,6-dihydropyrimidin-5-yl]methyl}pyridin-2-yl}-N'-hydroxybenzimidamide instead of 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of the Example 14, the reaction and the treatment were performed in the same manner as the Process 3 of the Example 14 to give 3-{2-{5-{[4-butyl-1-(5-ethoxypyrimidin-2-yl)-2-methyl-6-oxo-1,6-dihydropyrimidin-5-yl]methyl}pyridin-2-yl}phenyl}-1,2,4-oxadiazol-5(4H)-one (yield: 18%, two step yield) as pale yellow amorphous.

¹H-NMR (CDCl₃, 400 MHz) δ:

0.95 (3H, t, J=7 Hz), 1.38-1.48 (2H, m), 1.51 (3H, t, J=7 Hz), 1.62-1.68 (2H, m), 2.17 (3H, s), 2.66-2.70 (2H, m), 3.95 (2H, s), 4.22 (2H, q, J=7 Hz), 7.38-7.61 (4H, m), 7.79 (1H, d, J=7 Hz), 7.90 (1H, d, J=7 Hz), 8.51 (2H, s), 8.54 (1H, s).

Example 18

Preparation of 3-{2-{5-{[4-butyl-2-ethyl-1-(5-methoxypyrimidin-2-yl)-6-oxo-1,6-dihydropyrimidin-5-yl]methyl}pyridin-2-yl}phenyl}-1,2,4-oxadiazol-5(4H)-one

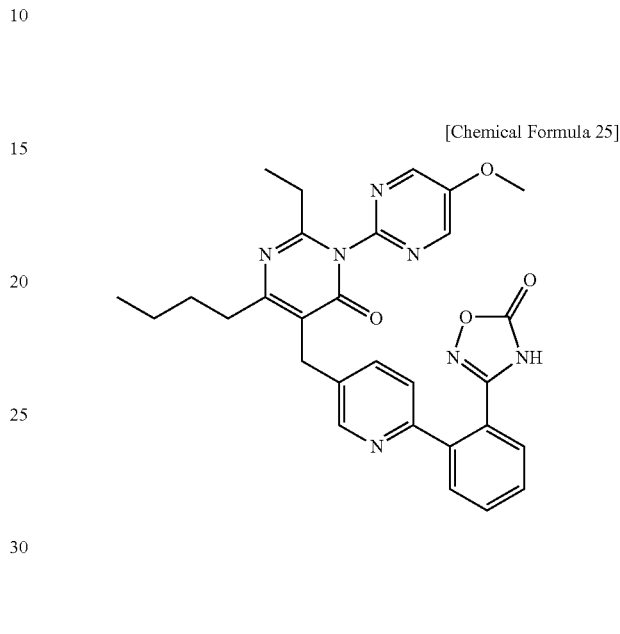

[Chemical Formula 25]

Process 1: By using 2-{5-{[4-butyl-2-ethyl-1-(5-methoxypyrimidin-2-yl)-6-oxo-1,6-dihydropyrimidin-5-yl]methyl}pyridin-2-yl}benzonitrile obtained from the Process 2 of the Example 3 instead of 2-{5-{[4-butyl-2-methyl-6-oxo-1-(pyridin-2-yl)-1,6-dihydropyrimidin-5-yl]methyl}pyridin-2-yl}benzonitrile in the Process 2 of the Example 14, the reaction and the treatment were performed in the same manner as the Process 2 of the Example 14 to give 2-{5-{[4-butyl-2-ethyl-1-(5-methoxypyrimidin-2-yl)-6-oxo-1,6-dihydropyrimidin-5-yl]methyl}pyridin-2-yl}-N'-hydroxybenzimidamide.

Process 2: By using 2-{5-{[4-butyl-2-ethyl-1-(5-methoxypyrimidin-2-yl)-6-oxo-1,6-dihydropyrimidin-5-yl]methyl}pyridin-2-yl}-N'-hydroxybenzimidamide instead of 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of the Example 14, the reaction and the treatment were performed in the same manner as the Process 3 of the Example 14 to give 3-{2-{5-{[4-butyl-2-ethyl-1-(5-methoxypyrimidin-2-yl)-6-oxo-1,6-dihydropyrimidin-5-yl]methyl}pyridin-2-yl}phenyl}-1,2,4-oxadiazol-5(4H)-one (yield: 53%, two step yield) as white amorphous.

¹H-NMR (CDCl₃, 400 MHz) δ:

0.95 (3H, t, J=7 Hz), 1.18 (3H, t, J=7 Hz), 1.36-1.50 (2H, m), 1.61-1.75 (2H, m), 2.32 (2H, q, J=7 Hz), 2.71 (2H, t, J=8 Hz), 3.95 (2H, s), 4.00 (3H, s), 4.79 (1H, br s), 7.38 (1H, d, J=8 Hz), 7.45 (1H, dd, J=8, 1 Hz), 7.51 (1H, dd, J=8, 1 Hz), 7.59 (1H, td, J=8, 2 Hz), 7.79 (1H, dd, J=8, 2 Hz), 7.89 (1H, dd, J=8, 1 Hz), 8.52-8.55 (3H, m).

Example 19

Preparation of 3-{2-{5-{[4-butyl-1-(5-ethoxypyrimidin-2-yl)-2-ethyl-6-oxo-1,6-dihydropyrimidin-5-yl]methyl}pyridin-2-yl}phenyl}-1,2,4-oxadiazol-5(4H)-one

[Chemical Formula 26]

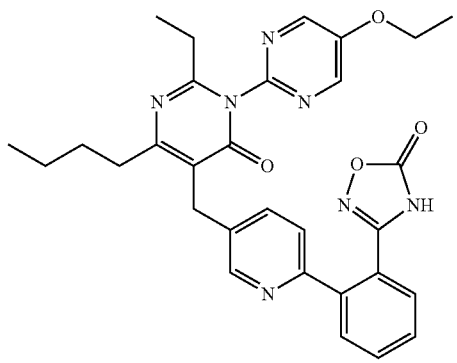

Process 1: By using 2-{5-{[4-butyl-1-(5-ethoxypyrimidin-2-yl)-2-ethyl-6-oxo-1,6-dihydropyrimidin-5-yl]methyl}pyridin-2-yl}benzonitrile obtained from the Process 1 of the Example 4 instead of 2-{5-{[4-butyl-2-methyl-6-oxo-1-(pyridin-2-yl)-1,6-dihydropyrimidin-5-yl]methyl}pyridin-2-yl}benzonitrile in the Process 2 of the Example 14, the reaction and the treatment were performed in the same manner as the Process 2 of the Example 14 to give 2-{5-{[4-butyl-1-(5-ethoxypyrimidin-2-yl)-2-ethyl-6-oxo-1,6-dihydropyrimidin-5-yl]methyl}pyridin-2-yl}-N'-hydroxybenzimidamide.

Process 2: By using 2-{5-{[4-butyl-1-(5-ethoxypyrimidin-2-yl)-2-ethyl-6-oxo-1,6-dihydropyrimidin-5-yl]methyl}pyridin-2-yl}-N'-hydroxybenzimidamide instead of 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of the Example 14, the reaction and the treatment were performed in the same manner as the Process 3 of the Example 14 to give 3-{2-{5-{[4-butyl-1-(5-ethoxypyrimidin-2-yl)-2-ethyl-6-oxo-1,6-dihydropyrimidin-5-yl]methyl}pyridin-2-yl}phenyl}-1,2,4-oxadiazol-5(4H)-one (yield: 73%, two step yield) as white amorphous.

$^1$H-NMR (CDCl$_3$, 400 MHz) δ:
0.94 (3H, t, J=7 Hz), 1.18 (3H, t, J=7 Hz), 1.34-1.47 (2H, m), 1.51 (3H, t, J=7 Hz), 1.60-1.74 (2H, m), 2.32 (2H, q, J=7 Hz), 2.70 (2H, t, J=8 Hz), 3.94 (2H, s), 4.22 (2H, q, J=7 Hz), 7.36 (1H, d, J=8 Hz), 7.41-7.61 (3H, m), 7.77 (1H, dd, J=8, 2 Hz), 7.85 (1H, dd, J=8, 1 Hz), 8.48-8.53 (3H, m).

Example 20

Preparation of 3-{2-{5-{[4-butyl-2-isopropyl-1-(5-methoxypyrimidin-2-yl)-6-oxo-1,6-dihydropyrimidin-5-yl]methyl}pyridin-2-yl}phenyl}-1,2,4-oxadiazol-5(4H)-one

[Chemical Formula 27]

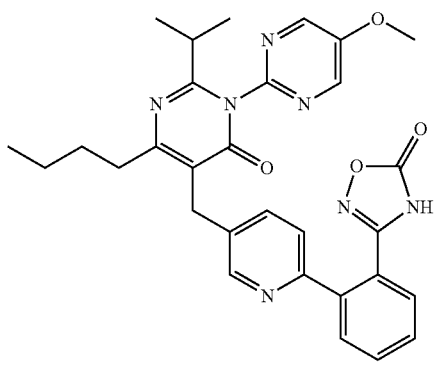

Process 1: By using 2-{5-{[4-butyl-2-isopropyl-1-(5-methoxypyrimidin-2-yl)-6-oxo-1,6-dihydropyrimidin-5-yl]methyl}pyridin-2-yl}benzonitrile obtained from the Process 2 of the Example 5 instead of 2-{5-{[4-butyl-2-methyl-6-oxo-1-(pyridin-2-yl)-1,6-dihydropyrimidin-5-yl]methyl}pyridin-2-yl}benzonitrile in the Process 2 of the Example 14, the reaction and the treatment were performed in the same manner as the Process 2 of the Example 14 to give 2-{5-{[4-butyl-2-isopropyl-1-(5-methoxypyrimidin-2-yl)-6-oxo-1,6-dihydropyrimidin-5-yl]methyl}pyridin-2-yl}-N'-hydroxybenzimidamide.

Process 2: By using 2-{5-{[4-butyl-2-isopropyl-1-(5-methoxypyrimidin-2-yl)-6-oxo-1,6-dihydropyrimidin-5-yl]methyl}pyridin-2-yl}-N'-hydroxybenzimidamide instead of 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of the Example 14, the reaction and the treatment were performed in the same manner as the Process 3 of the Example 14 to give 3-{2-{5-{[4-butyl-2-isopropyl-1-(5-methoxypyrimidin-2-yl)-6-oxo-1,6-dihydropyrimidin-5-yl]methyl}pyridin-2-yl}phenyl}-1,2,4-oxadiazol-5(4H)-one (yield: 60%, two step yield) as white amorphous.

$^1$H-NMR (CDCl$_3$, 400 MHz) δ:
0.95 (3H, t, J=7 Hz), 1.19 (6H, d, J=7 Hz), 1.31-1.49 (2H, m), 1.60-1.75 (2H, m), 2.23-2.35 (1H, m), 2.70 (2H, t, J=8 Hz), 3.93 (2H, s), 4.00 (3H, s), 7.36 (1H, d, J=8 Hz), 7.43 (1H, dd, J=7, 1 Hz), 7.49 (1H, dd, J=7, 1 Hz), 7.57 (1H, td, J=8, 1 Hz), 7.79 (1H, dd, J=8, 2 Hz), 7.85 (1H, dd, J=8, 1 Hz), 8.50 (1H, d, J=2 Hz), 8.53 (2H, s).

Example 21

Preparation of 3-{2-{5-{[4-butyl-1-(5-ethoxypyrimidin-2-yl)-2-isopropyl-6-oxo-1,6-dihydropyrimidin-5-yl]methyl}pyridin-2-yl}phenyl}-1,2,4-oxadiazol-5(4H)-one

[Chemical Formula 28]

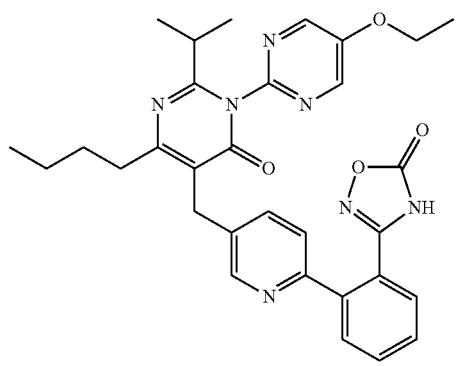

Process 1: By using 2-{5-{[4-butyl-1-(5-ethoxypyrimidin-2-yl)-2-isopropyl-6-oxo-1,6-dihydropyrimidin-5-yl]methyl}pyridin-2-yl}benzonitrile obtained from the Process 1 of the Example 6 instead of 2-{5-{[4-butyl-2-methyl-6-oxo-1-(pyridin-2-yl)-1,6-dihydropyrimidin-5-yl]methyl}pyridin-2-yl}benzonitrile in the Process 2 of the Example 14, the reaction and the treatment were performed in the same manner as the Process 2 of the Example 14 to give 2-{5-{[4-butyl-1-(5-ethoxypyrimidin-2-yl)-2-isopropyl-6-oxo-1,6-dihydropyrimidin-5-yl]methyl}pyridin-2-yl}-N'-hydroxybenzimidamide.

Process 2: By using 2-{5-{[4-butyl-1-(5-ethoxypyrimidin-2-yl)-2-isopropyl-6-oxo-1,6-dihydropyrimidin-5-yl]methyl}pyridin-2-yl}-N'-hydroxybenzimidamide instead of 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of the Example 14, the reaction and the treatment were performed in the same manner as the Process 3 of the Example 14 to give 3-{2-{5-{[4-butyl-1-(5-ethoxypyrimidin-2-yl)-2-isopropyl-6-oxo-1,6-dihydropyrimidin-5-yl]methyl}pyridin-2-yl}phenyl}-1,2,4-oxadiazol-5(4H)-one (yield: 66%, two step yield) as white amorphous.

¹H-NMR (CDCl₃, 400 MHz) δ:
0.95 (3H, t, J=7 Hz), 1.20 (6H, d, J=7 Hz), 1.36-1.46 (2H, m), 1.51 (3H, t, J=7 Hz), 1.62-1.74 (2H, m), 2.23-2.35 (1H, m), 2.72 (2H, t, J=8 Hz), 3.94 (2H, s), 4.22 (2H, q, J=7 Hz), 7.40 (1H, d, J=9 Hz), 7.46 (1H, dd, J=8, 1 Hz), 7.52 (1H, td, J=8, 2 Hz), 7.61 (1H, td, J=8, 2 Hz), 7.82 (1H, dd, J=8, 2 Hz), 7.95 (1H, dd, J=8, 1 Hz), 8.51 (2H, s), 8.58 (1H, d, J=2 Hz).

Example 22

Preparation of 3-{2-{5-{[4-butyl-2-cyclopropyl-1-(5-methoxypyrimidin-2-yl)-6-oxo-1,6-dihydropyrimidin-5-yl]methyl}pyridin-2-yl}phenyl}-1,2,4-oxadiazol-5(4H)-one

[Chemical Formula 29]

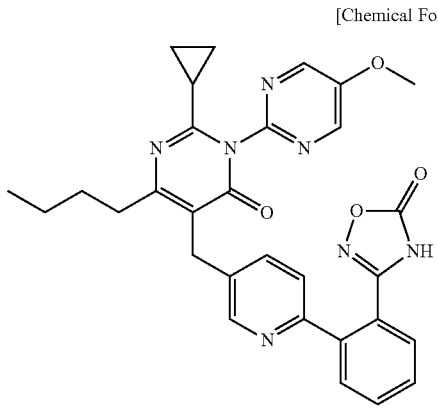

Process 1: By using 2-{5-{[4-butyl-2-cyclopropyl-1-(5-methoxypyrimidin-2-yl)-6-oxo-1,6-dihydropyrimidin-5-yl]methyl}pyridin-2-yl}benzonitrile obtained from the Process 2 of the Example 7 instead of 2-{5-{[4-butyl-2-methyl-6-oxo-1-(pyridin-2-yl)-1,6-dihydropyrimidin-5-yl]methyl}pyridin-2-yl}benzonitrile in the Process 2 of the Example 14, the reaction and the treatment were performed in the same manner as the Process 2 of the Example 14 to give 2-{5-{[4-butyl-2-cyclopropyl-1-(5-methoxypyrimidin-2-yl)-6-oxo-1,6-dihydropyrimidin-5-yl]methyl}pyridin-2-yl}-N'-hydroxybenzimidamide.

Process 2: By using 2-{5-{[4-butyl-2-cyclopropyl-1-(5-methoxypyrimidin-2-yl)-6-oxo-1,6-dihydropyrimidin-5-yl]methyl}pyridin-2-yl}-N'-hydroxybenzimidamide instead of 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of the Example 14, the reaction and the treatment were performed in the same manner as the Process 3 of the Example 14 to give 3-{2-{5-{[4-butyl-2-cyclopropyl-1-(5-methoxypyrimidin-2-yl)-6-oxo-1,6-dihydropyrimidin-5-yl]methyl}pyridin-2-yl}phenyl}-1,2,4-oxadiazol-5(4H)-one (yield: 84%, two step yield) as white amorphous.

¹H-NMR (CDCl₃, 400 MHz) δ:
0.81-0.89 (2H, m), 0.93 (3H, t, J=7 Hz), 1.06-1.15 (1H, m), 1.24 (2H, t, J=4 Hz), 1.32-1.44 (2H, m), 1.55-1.67 (2H, m), 2.63 (2H, t, J=8 Hz), 3.92 (2H, s), 4.00 (3H, s), 7.37 (1H, d, J=8 Hz), 7.45 (1H, d, J=8 Hz), 7.51 (1H, dd, J=8, 1 Hz), 7.59 (1H, td, J=8, 1 Hz), 7.78 (1H, dd, J=8, 2 Hz), 7.89 (1H, d, J=7 Hz), 8.52 (1H, d, J=2 Hz), 8.56 (2H, s).

Example 23

Preparation of 3-{2-{5-{[4-butyl-2-cyclopropyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one

[Chemical Formula 30]

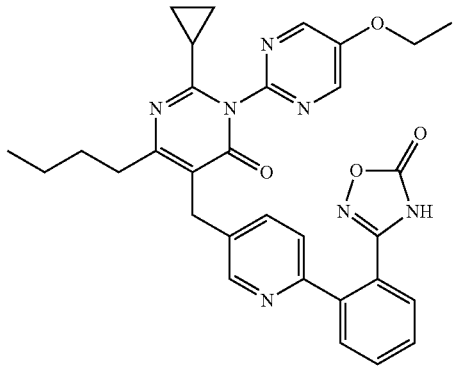

Process 1: By using 2-amino-5-ethoxypyrimidine instead of 2-amino-5-methoxypyrimidine in the Process 3 of the Example 1 and also using methyl (Z)-2-{[6-(2-cyanophenyl)pyridin-3-yl]methyl}-3-(cyclopropanecarboxamide)-2-heptenoate instead of methyl (Z)-3-acetamide-2-{[6-(2-cyanophenyl)pyridin-3-yl]methyl}-2-heptenoate, the reaction and the treatment were performed in the same manner as the Process 3 of the Example 1 to give 2-{5-{[4-butyl-2-cyclopropyl-1-(5-ethoxypyrimidin-2-yl)-6-oxo-1,6-dihydropyrimidin-5-yl]methyl}pyridin-2-yl}benzonitrile (yield: 65%) as yellow oil.

¹H-NMR (CDCl₃, 400 MHz) δ:
0.79-0.87 (2H, m), 0.92 (3H, t, J=8 Hz), 1.09-1.16 (1H, m), 1.18-1.29 (2H, m), 1.30-1.43 (2H, m), 1.51 (3H, t, J=7 Hz), 1.54-1.66 (2H, m), 2.61 (2H, t, J=8 Hz), 3.94 (2H, s), 4.22 (2H, q, J=7 Hz), 7.47 (1H, t, J=8 Hz), 7.57-7.69 (2H, m), 7.71-7.83 (3H, m), 8.54 (2H, s), 8.68 (1H, s).

Process 2: By using 2-{5-{[4-butyl-2-cyclopropyl-1-(5-ethoxypyrimidin-2-yl)-6-oxo-1,6-dihydropyrimidin-5-yl]methyl}pyridin-2-yl}benzonitrile instead of 2-{5-{[4-butyl-2-methyl-6-oxo-1-(pyridin-2-yl)-1,6-dihydropyrimidin-5-yl]methyl}pyridin-2-yl}benzonitrile in the Process 2 of the Example 14, the reaction and the treatment were performed in the same manner as the Process 2 of the Example 14 to give 2-{5-{[4-butyl-2-cyclopropyl-1-(5-ethoxypyrimidin-2-yl)-6-oxo-1,6-dihydropyrimidin-5-yl]methyl}pyridin-2-yl}-N'-hydroxybenzimidamide.

Process 3: By using 2-{5-{[4-butyl-2-cyclopropyl-1-(5-ethoxypyrimidin-2-yl)-6-oxo-1,6-dihydropyrimidin-5-yl]methyl}pyridin-2-yl}-N'-hydroxybenzimidamide instead of 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of the Example 14, the reaction and the treatment were performed in the same manner as the Process 3 of the Example 14 to give 3-{2-{5-{[4-butyl-2-cyclopropyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one (yield: 38%, two step yield) as colorless crystalline powder.

¹H-NMR (CDCl₃, 400 MHz) δ:

0.76-0.87 (2H, m), 0.92 (3H, t, J=7 Hz), 1.05-1.15 (1H, m), 1.16-1.28 (2H, m), 1.32-1.44 (2H, m), 1.51 (3H, t, J=7 Hz), 1.54-1.66 (2H, m), 2.61 (2H, t, J=8 Hz), 3.91 (2H, s), 4.22 (2H, q, J=7 Hz), 7.34 (1H, d, J=8 Hz), 7.38-7.50 (2H, m), 7.51-7.59 (1H, m), 7.71-7.86 (2H, m), 8.46 (1H, s), 8.54 (2H, s).

Example 24

Preparation of 3-{2-{5-{[4-butyl-2-cyclobutyl-1-(5-methoxypyrimidin-2-yl)-6-oxo-1,6-dihydropyrimidin-5-yl]methyl}pyridin-2-yl}phenyl}-1,2,4-oxadiazol-5(4H)-one

[Chemical Formula 31]

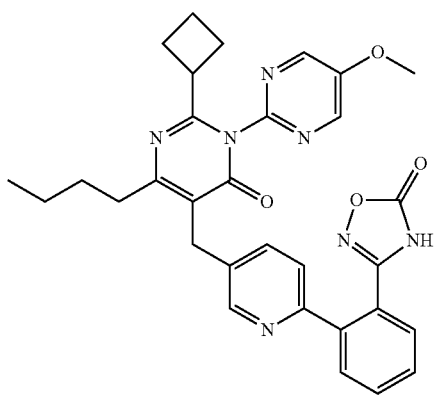

Process 1: By using 2-{5-{[4-butyl-2-cyclobutyl-1-(5-methoxypyrimidin-2-yl)-6-oxo-1,6-dihydropyrimidin-5-yl]methyl}pyridin-2-yl}benzonitrile obtained from the Process 2 of the Example 8 instead of 2-{5-{[4-butyl-2-methyl-6-oxo-1-(pyridin-2-yl)-1,6-dihydropyrimidin-5-yl]methyl}pyridin-2-yl}benzonitrile in the Process 2 of the Example 14, the reaction and the treatment were performed in the same manner as the Process 2 of the Example 14 to give 2-{5-{[4-butyl-2-cyclobutyl-1-(5-methoxypyrimidin-2-yl)-6-oxo-1,6-dihydropyrimidin-5-yl]methyl}pyridin-2-yl}-N'-hydroxbenzimidamide.

Process 2: By using 2-{5-{[4-butyl-2-cyclobutyl-1-(5-methoxypyrimidin-2-yl)-6-oxo-1,6-dihydropyrimidin-5-yl]methyl}pyridin-2-yl}-N'-hydroxbenzimidamide instead of 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of the Example 14, the reaction and the treatment were performed in the same manner as the Process 3 of the Example 14 to give 3-{2-{5-{[4-butyl-2-cyclobutyl-1-(5-methoxypyrimidin-2-yl)-6-oxo-1,6-dihydropyrimidin-5-yl]methyl}pyridin-2-yl}phenyl}-1,2,4-oxadiazol-5(4H)-one (yield: 65%, two step yield) as white amorphous.

¹H-NMR (CDCl₃, 400 MHz) δ:

0.96 (3H, t, J=7 Hz), 1.35-1.51 (2H, m), 1.64-1.85 (6H, m), 2.37-2.53 (2H, m), 2.72 (2H, t, J=8 Hz), 3.04-3.20 (1H, m), 3.94 (2H, s), 4.00 (3H, s), 7.34 (1H, d, J=8 Hz), 7.39-7.44 (1H, m), 7.44-7.49 (1H, m), 7.51-7.59 (1H, m), 7.74-7.83 (2H, m), 8.48 (1H, d, J=2 Hz), 8.52 (2H, s).

Example 25

Preparation of 3-{2-{5-{[4-butyl-2-cyclobutyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one

[Chemical Formula 32]

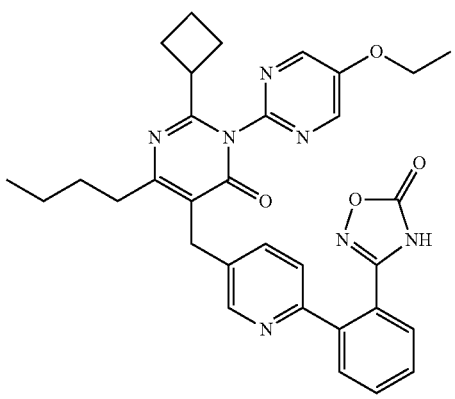

Process 1: By using 2-{5-{[4-butyl-2-cyclobutyl-1-(5-ethoxypyrimidin-2-yl)-6-oxo-1,6-dihydropyrimidin-5-yl]methyl}pyridin-2-yl}benzonitrile obtained from the Process 1 of the Example 9 instead of 2-{5-{[4-butyl-2-methyl-6-oxo-1-(pyridin-2-yl)-1,6-dihydropyrimidin-5-yl]methyl}pyridin-2-yl}benzonitrile in the Process 2 of the Example 14, the reaction and the treatment were performed in the same manner as the Process 2 of the Example 14 to give 2-{5-{[4-butyl-2-cyclobutyl-1-(5-ethoxypyrimidin-2-yl)-6-oxo-1,6-dihydropyrimidin-5-yl]methyl}pyridin-2-yl}-N'-hydroxybenzimidamide.

Process 2: By using 2-{5-{[4-butyl-2-cyclobutyl-1-(5-ethoxypyrimidin-2-yl)-6-oxo-1,6-dihydropyrimidin-5-yl]methyl}pyridin-2-yl}-N'-hydroxybenzimidamide instead of 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of the Example 14, the reaction and the treatment were performed in the same manner as the Process 3 of the Example 14 to give 3-{2-{5-{[4-butyl-2-cyclobutyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one (yield: 48%, two step yield) as white amorphous.

¹H-NMR (CDCl₃, 400 MHz) δ:

0.97 (3H, t, J=7 Hz), 1.35-1.47 (2H, m), 1.48-1.83 (9H, m), 2.38-2.52 (2H, m), 2.74 (2H, t, J=8 Hz), 3.03-3.18 (1H, m), 3.95 (2H, s), 4.22 (2H, q, J=7 Hz), 7.40 (1H, d, J=8 Hz), 7.46

(1H, d, J=8 Hz), 7.54 (1H, dd, J=8, 2 Hz), 7.61 (1H, td, J=8, 2 Hz), 7.81 (1H, dd, J=8, 2 Hz), 7.95 (1H, dd, J=8, 1 Hz), 8.49 (2H, s), 8.58 (1H, d, J=2 Hz).

Example 26

Preparation of 3-{2-{5-{[4-butyl-2-cyclopentyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one

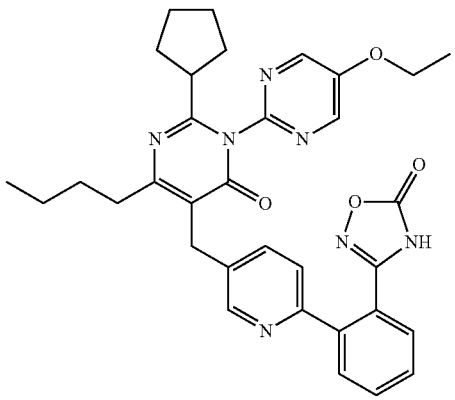

[Chemical Formula 33]

Process 1: By using 2-{5-{[4-butyl-2-cyclopentyl-1-(5-ethoxypyrimidin-2-yl)-6-oxo-1,6-dihydropyrimidin-5-yl]methyl}pyridin-2-yl}benzonitrile obtained from the Process 2 of the Example 10 instead of 2-{5-{[4-butyl-2-methyl-6-oxo-1-(pyridin-2-yl)-1,6-dihydropyrimidin-5-yl]methyl}pyridin-2-yl}benzonitrile in the Process 2 of the Example 14, the reaction and the treatment were performed in the same manner as the Process 2 of the Example 14 to give 2-{5-{[4-butyl-2-cyclopentyl-1-(5-ethoxypyrimidin-2-yl)-6-oxo-1,6-dihydropyrimidin-5-yl]methyl}pyridin-2-yl}-N'-hydroxbenzimidamide.

Process 2: By using 2-{5-{[4-butyl-2-cyclopentyl-1-(5-ethoxypyrimidin-2-yl)-6-oxo-1,6-dihydropyrimidin-5-yl]methyl}pyridin-2-yl}-N'-hydroxbenzimidamide instead of 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of the Example 14, the reaction and the treatment were performed in the same manner as the Process 3 of the Example 14 to give 3-{2-{5-{[4-butyl-2-cyclopentyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one (yield: 56%, two step yield) as pale brown amorphous.

$^1$H-NMR (CDCl$_3$, 400 MHz) δ:

0.94 (3H, t, J=7 Hz), 1.32-1.57 (7H, m), 1.60-1.85 (6H, m), 1.90-2.06 (2H, m), 2.36-2.52 (1H, m), 2.68 (2H, t, J=7 Hz), 3.93 (2H, s), 4.22 (2H, q, J=7 Hz), 7.35 (1H, d, J=8 Hz), 7.40-7.60 (3H, m), 7.78 (1H, dd, J=8, 2 Hz), 7.83 (1H, dd, J=8, 1 Hz), 8.49 (1H, d, J=2 Hz), 8.51 (2H, s).

Example 27

Preparation of 3-{2-{5-{[4-butyl-2-cyclohexyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one

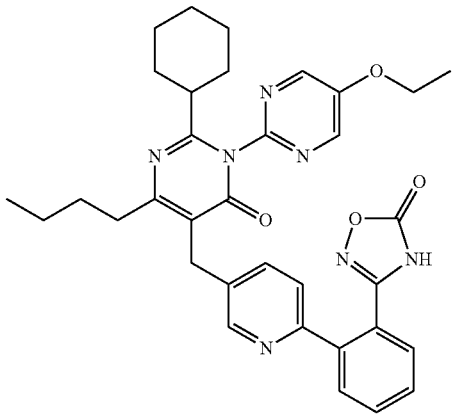

[Chemical Formula 34]

Process 1: By using 2-{5-{[4-butyl-2-cyclohexyl-1-(5-ethoxypyrimidin-2-yl)-6-oxo-1,6-dihydropyrimidin-5-yl]methyl}pyridin-2-yl}benzonitrile obtained from the Process 2 of the Example 11 instead of 2-{5-{[4-butyl-2-methyl-6-oxo-1-(pyridin-2-yl)-1,6-dihydropyrimidin-5-yl]methyl}pyridin-2-yl}benzonitrile in the Process 2 of the Example 14, the reaction and the treatment were performed in the same manner as the Process 2 of the Example 14 to give 2-{5-{[4-butyl-2-cyclohexyl-1-(5-ethoxypyrimidin-2-yl)-6-oxo-1,6-dihydropyrimidin-5-yl]methyl}pyridin-2-yl}-N'-hydroxybenzimidamide.

Process 2: By using 2-{5-{[4-butyl-2-cyclohexyl-1-(5-ethoxypyrimidin-2-yl)-6-oxo-1,6-dihydropyrimidin-5-yl]methyl}pyridin-2-yl}-N'-hydroxybenzimidamide instead of 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of the Example 14, the reaction and the treatment were performed in the same manner as the Process 3 of the Example 14 to give 3-{2-{5-{[4-butyl-2-cyclohexyl-1-(5-ethoxypyrimidin-2-yl)-6-oxo-1,6-dihydropyrimidin-5-yl]methyl}pyridin-2-yl}phenyl}-1,2,4-oxadiazol-5(4H)-one (yield: 60%) as pale brown amorphous.

$^1$H-NMR (CDCl$_3$, 400 MHz) δ:

0.89-1.07 (5H, m), 1.34-1.94 (16H, m), 2.68 (2H, t, J=8 Hz), 3.92 (2H, s), 4.23 (2H, q, J=7 Hz), 7.34 (1H, d, J=8 Hz), 7.39-7.49 (2H, m), 7.50-7.59 (1H, m), 7.74-7.83 (2H, m), 8.47 (1H, d, J=2 Hz), 8.51 (2H, s).

Example 28

Preparation of 3-{2-{5-{{4-butyl-2-methyl-1-{5-[2-(methylthio)ethoxy]pyrimidin-2-yl}-6-oxo-1,6-dihydropyrimidin-5-yl}methyl}pyridin-2-yl}phenyl}-1,2,4-oxadiazol-5(4H)-one

[Chemical Formula 35]

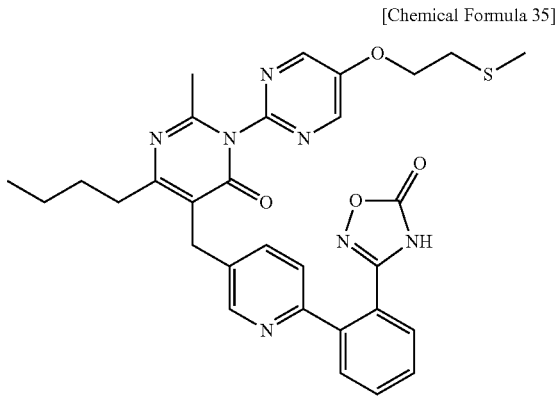 [SMILES: CCCCc1nc(C)n(-c2ncc(OCCSC)cn2)c(=O)c1Cc1ccc(-c2ccccc2-c2noc(=O)[nH]2)nc1]

Process 1: By using 2-{5-{{4-butyl-2-methyl-1-{5-[2-(methylthio)ethoxy]pyrimidin-2-yl}-6-oxo-1,6-dihydropyrimidin-5-yl}methyl}pyridin-2-yl}benzonitrile obtained from the Process 1 of the Example 12 instead of 2-{5-{[4-butyl-2-methyl-6-oxo-1-(pyridin-2-yl)-1,6-dihydropyrimidin-5-yl]methyl}pyridin-2-yl}benzonitrile in the Process 2 of the Example 14, the reaction and the treatment were performed in the same manner as the Process 2 of the Example 14 to give 2-{5-{{4-butyl-2-methyl-1-{5-[2-(methylthio)ethoxy]pyrimidin-2-yl}-6-oxo-1,6-dihydropyrimidin-5-yl}methyl}pyridin-2-yl}-N'-hydroxybenzimidamide.

Process 2: By using 2-{5-{{4-butyl-2-methyl-1-{5-[2-(methylthio)ethoxy]pyrimidin-2-yl}-6-oxo-1,6-dihydropyrimidin-5-yl}methyl}pyridin-2-yl}-N'-hydroxybenzimidamide instead of 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of the Example 14, the reaction and the treatment were performed in the same manner as the Process 3 of the Example 14 to give 3-{2-{5-{{4-butyl-2-methyl-1-{5-[2-(methylthio)ethoxy]pyrimidin-2-yl}-6-oxo-1,6-dihydropyrimidin-5-yl}methyl}pyridin-2-yl}phenyl}-1,2,4-oxadiazol-5(4H)-one (yield: 56%, two step yield) as weak yellow oil.

$^1$H-NMR (CDCl$_3$, 400 MHz) δ:

0.95 (3H, t, J=7 Hz), 1.40-1.46 (2H, m), 1.50-1.70 (2H, m), 2.17 (3H, s), 2.24 (3H, s), 2.68-2.71 (2H, m), 2.96 (2H, t, J=7 Hz), 3.96 (2H, s), 4.33 (2H, t, J=7 Hz), 7.40-7.62 (4H, m), 7.66-7.97 (2H, m), 8.55 (2H, s), 8.58 (1H, s).

Example 29

Preparation of 3-{2-{5-{{4-butyl-2-methyl-1-{5-[2-(methylsulfonyl)ethoxy]pyrimidin-2-yl}-6-oxo-1,6-dihydropyrimidin-5-yl}methyl}pyridin-2-yl}phenyl}-1,2,4-oxadiazol-5(4H)-one

[Chemical Formula 36]

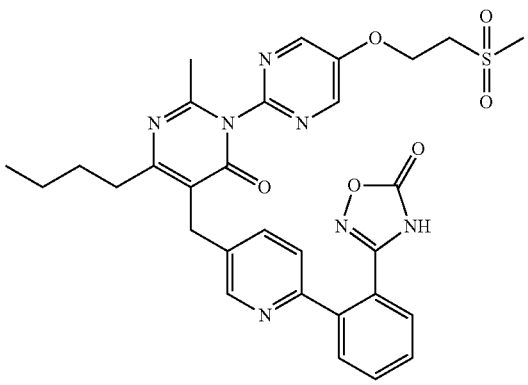

By using 3-{2-{5-{{4-butyl-2-methyl-1-{5-[2-(methylthio)ethoxy]pyrimidin-2-yl}-6-oxo-1,6-dihydropyrimidin-5-yl}methyl}pyridin-2-yl}phenyl}-1,2,4-oxadiazol-5(4H)-one obtained in the Example 28, the reaction and the treatment were performed in the same manner as the Example 13 to give 3-{2-{5-{{4-butyl-2-methyl-1-{5-[2-(methylsulfonyl)ethoxy]pyrimidin-2-yl}-6-oxo-1,6-dihydropyrimidin-5-yl}methyl}pyridin-2-yl}phenyl}-1,2,4-oxadiazol-5(4H)-one (yield: 63%) as colorless oil.

$^1$H-NMR (CDCl$_3$, 400 MHz) δ:

0.95 (3H, t, J=7 Hz), 1.40-1.46 (2H, m), 1.65-1.70 (2H, m), 2.18 (3H, s), 2.67-2.71 (2H, m), 3.09 (3H, s), 3.53-3.55 (2H, m), 3.92 (2H, s), 4.63-4.66 (2H, m), 7.36-7.60 (4H, m), 7.74 (1H, d, J=8 Hz), 7.88 (1H, d, J=8 Hz), 8.59 (1H, s), 8.60 (2H, s).

Example 30

Preparation of 5-{{5-[2-(1H-tetrazol-5-yl)phenyl]pyridin-2-yl}methyl}-6-butyl-2-methyl-3-(pyridin-2-yl)pyrimidin-4(3H)-one

[Chemical Formula 37]

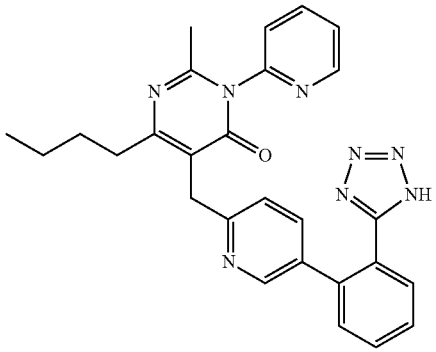

Process 1: By using 2-[6-(bromomethyl)pyridin-3-yl]benzonitrile instead of 2-[5-(bromomethyl)pyridin-2-yl]benzonitrile in the Process 1 of the Example 1, the reaction and the treatment were performed in the same manner as the Process 1 of the Example 1 to give 2-{[5-(2-cyanophenyl)pyridin-2-yl]methyl}-3-oxoheptanoate (yield: 69%) as yellow oil.

¹H-NMR (CDCl₃, 400 MHz) δ:

0.89 (3H, t, J=7 Hz), 1.24-1.34 (2H, m), 1.54-1.61 (2H, m), 2.59-2.76 (2H, m), 3.37-3.55 (2H, m), 3.73 (3H, s), 4.37 (1H, t, J=7 Hz), 7.33 (1H, d, J=8 Hz), 7.50 (2H, t, J=7 Hz), 7.66-7.70 (1H, m), 7.78-7.83 (2H, m), 8.63 (1H, d, J=2 Hz).

Process 2: By using methyl 2-{[5-(2-cyanophenyl)pyridin-2-yl]methyl}-3-oxoheptanoate instead of methyl 2-{[6-(2-cyanophenyl)pyridin-3-yl]methyl}-3-oxoheptanoate in the Process 2 of the Example 1, the reaction and the treatment were performed in the same manner as the Process 2 of the Example 1 to give methyl (Z)-3-acetamide-2-{[5-(2-cyanophenyl)pyridin-2-yl]methyl}-2-heptenoate (yield: 100%) as yellow oil.

¹H-NMR (CDCl₃, 400 MHz) δ:

0.89 (3H, t, J=7 Hz), 1.27-1.40 (2H, m), 1.47-1.59 (2H, m), 2.24 (3H, s), 3.14 (2H, t, J=8 Hz), 3.78 (3H, s), 3.88 (2H, s), 7.42-7.56 (3H, m), 7.65-7.91 (3H, m), 8.63 (1H, s), 10.9 (1H, s).

Process 3: By using 2-aminopyridine instead of 2-amino-5-methoxypyrimidine in the Process 3 of the Example 1 and also using methyl (Z)-3-acetamide-2-{[5-(2-cyanophenyl)pyridin-2-yl]methyl}-2-heptenoate instead of methyl (Z)-3-acetamide-2-{[6-(2-cyanophenyl)pyridin-3-yl]methyl}-2-heptenoate, the reaction and the treatment were performed in the same manner as the Process 3 of the Example 1 to give 2-{6-{[4-butyl-2-methyl-6-oxo-1-(pyridin-2-yl)-1,6-dihydropyrimidin-5-yl]methyl}pyridin-3-yl}benzonitrile (yield: 35%).

¹H-NMR (CDCl₃, 400 MHz) δ:

0.93 (3H, t, J=7 Hz), 1.42 (2H, sextet, J=8 Hz), 1.60-1.75 (2H, m), 2.17 (3H, s), 2.74-2.78 (2H, m), 4.17 (2H, s), 7.38-7.50 (5H, m), 7.67 (1H, m), 7.77-7.80 (2H, m), 7.93 (1H, m), 8.65 (1H, m, J=2 Hz), 8.68 (1H, d, J=3 Hz).

Process 4: By using 2-{6-{[4-butyl-2-methyl-6-oxo-1-(pyridin-2-yl)-1,6-dihydropyrimidin-5-yl]methyl}pyridin-3-yl}benzonitrile instead of 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of the Example 1, the reaction and the treatment were performed in the same manner as the Process 4 of the Example 1 to give 5-{{5-[2-(1H-tetrazol-5-yl)phenyl]pyridin-2-yl}methyl}-6-butyl-2-methyl-3-(pyridin-2-yl)pyrimidin-4(3H)-one (yield: 79%) as pale yellow amorphous.

¹H-NMR (CDCl₃, 400 MHz) δ:

0.89 (3H, t, J=7 Hz), 1.30-1.35 (2H, m), 1.50-1.58 (2H, m), 2.18 (3H, s), 2.51-2.54 (2H, m), 3.75 (2H, s), 6.99 (1H, d, J=8 Hz), 7.16 (1H, d, J=8 Hz), 7.31-7.36 (3H, m), 7.48-7.56 (2H, m), 7.83-7.87 (2H, m), 7.97 (1H, s), 8.56 (1H, d, J=4 Hz).

Example 31

Preparation of 5-{{5-[2-(1H-tetrazol-5-yl)phenyl]pyridin-2-yl}methyl}-6-butyl-3-(5-methoxypyridin-2-yl)-2-methylpyrimidin-4(3H)-one

[Chemical Formula 38]

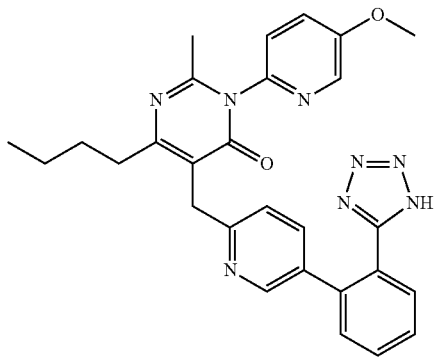

Process 1: By using 2-amino-5-methoxypyridine instead of 2-amino-5-methoxypyrimidine in the Process 3 of the Example 1 and also using methyl (Z)-3-acetamide-2-{[5-(2-cyanophenyl)pyridin-2-yl]methyl}-2-heptenoate obtained from the Process 2 of the Example 30 instead of methyl (Z)-3-acetamide-2-{[6-(2-cyanophenyl)pyridin-3-yl]methyl}-2-heptenoate, the reaction and the treatment were performed in the same manner as the Process 3 of the Example 1 to give 2-{6-{[4-butyl-1-(5-methoxypyridin-2-yl)-2-methyl-6-oxo-1,6-dihydropyrimidin-5-yl]methyl}pyridin-3-yl}benzonitrile (yield: 65%) as pale yellow amorphous.

¹H-NMR (CDCl₃, 400 MHz) δ:

0.93 (3H, t, J=7 Hz), 1.37-1.46 (2H, m), 1.58-1.66 (2H, m), 2.18 (3H, s), 2.76 (2H, t, J=8 Hz), 3.92 (3H, s), 4.16 (2H, s), 7.27-7.30 (1H, m), 7.38-7.49 (4H, m), 7.65-7.69 (1H, m), 7.77-7.79 (2H, m), 8.30 (1H, d, J=3 Hz), 8.65 (1H, d, J=2 Hz).

Process 2: By using 2-{6-{[4-butyl-1-(5-methoxypyridin-2-yl)-2-methyl-6-oxo-1,6-dihydropyrimidin-5-yl]methyl}pyridin-3-yl}benzonitrile instead of 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of the Example 1, the reaction and the treatment were performed in the same manner as the Process 4 of the Example 1 to give 5-{{5-[2-(1H-tetrazol-5-yl)phenyl]pyridin-2-yl}methyl}-6-butyl-3-(5-methoxypyridin-2-yl)-2-methylpyrimidin-4(3H)-one (yield: 72%) as pale yellow amorphous.

¹H-NMR (CDCl₃, 400 MHz) δ:

0.87 (3H, t, J=7 Hz), 1.21-1.30 (2H, m), 1.40-1.48 (2H, m), 2.09 (3H, s), 2.38 (2H, t, J=8 Hz), 3.60 (2H, s), 3.90 (3H, s), 7.00 (1H, d, J=8 Hz), 7.14 (2H, dd, J=8, 2 Hz), 7.20 (1H, d, J=9 Hz), 7.34-7.38 (2H, m), 7.53-7.61 (2H, m), 7.84 (1H, d, J=7 Hz), 7.90 (1H, s), 8.21 (1H, d, J=3 Hz).

Example 32

Preparation of 5-{{5-[2-(1H-tetrazol-5-yl)phenyl]pyridin-2-yl}methyl}-6-butyl-3-[3-chloro-5-(trifluoromethyl)pyridin-2-yl]-2-methylpyrimidin-4(3H)-one

[Chemical Formula 39]

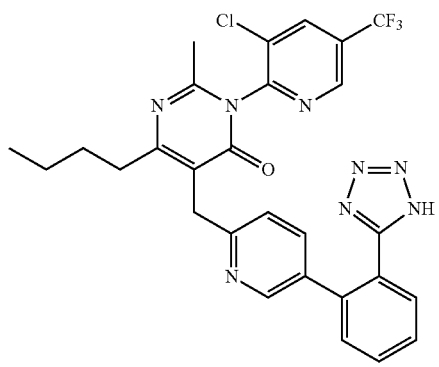

Process 1: By using 2-amino-3-chloro-5-(trifluoromethyl)pyridine instead of 2-amino-5-methoxypyrimidine in the Process 3 of the Example 1 and also using methyl (Z)-3-acetamide-2-{[5-(2-cyanophenyl)pyridin-2-yl]methyl}-2-heptenoate obtained from the Process 2 of the Example 30 instead of methyl (Z)-3-acetamide-2-{[6-(2-cyanophenyl)pyridin-3-yl]methyl}-2-heptenoate, the reaction and the treatment were performed in the same manner as the Process 3 of the Example 1 to give 2-{6-{{4-butyl-1-[3-chloro-5-(trifluoromethyl)pyridin-2-yl]-2-methyl-6-oxo-1,6-dihydropyrimidin-5-yl}methyl}pyridin-3-yl}benzonitrile (yield: 41%) as pale yellow amorphous.

$^1$H-NMR (CDCl$_3$, 400 MHz) δ:
0.94 (3H, t, J=7 Hz), 1.37-1.47 (2H, m), 1.57-1.68 (2H, m), 2.16 (3H, s), 2.70-2.83 (2H, m), 4.19 (2H, s), 7.38 (1H, d, J=8 Hz), 7.46-7.53 (2H, m), 7.65-7.69 (1H, m), 7.77-7.83 (2H, m), 7.89 (1H, m), 8.65 (1H, d, J=2 Hz), 8.84 (1H, s).

Process 2: By using 2-{6-{{4-butyl-1-[3-chloro-5-(trifluoromethyl)pyridin-2-yl]-2-methyl-6-oxo-1,6-dihydropyrimidin-5-yl}methyl}pyridin-3-yl}benzonitrile instead of 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of the Example 1, the reaction and the treatment were performed in the same manner as the Process 4 of the Example 1 to give 5-{{5-[2-(1H-tetrazol-5-yl)phenyl]pyridin-2-yl}methyl}-6-butyl-3-[3-chloro-5-(trifluoromethyl)pyridin-2-yl]-2-methylpyrimidin-4(3H)-one (yield: 43%) as pale yellow amorphous.

$^1$H-NMR (CDCl$_3$, 400 MHz) δ:
0.87 (3H, t, J=7 Hz), 1.22-1.30 (2H, m), 1.43-1.50 (2H, m), 2.09 (3H, s), 2.35-2.43 (2H, m), 3.55 (2H, dd, J=19, 16 Hz), 6.95 (1H, d, J=8 Hz), 7.11-7.14 (1H, m), 7.38-7.40 (1H, m), 7.54-7.61 (2H, m), 7.86-7.89 (1H, m), 7.94 (1H, m), 8.18 (1H, d, J=2 Hz), 8.81 (1H, s).

Example 33

Preparation on 5-{{5-[2-(1H-tetrazol-5-yl)phenyl]pyridin-2-yl}methyl}-6-butyl-3-(5-methoxypyrimidin-2-yl)-2-methylpyrimidin-4(3H)-one

[Chemical Formula 40]

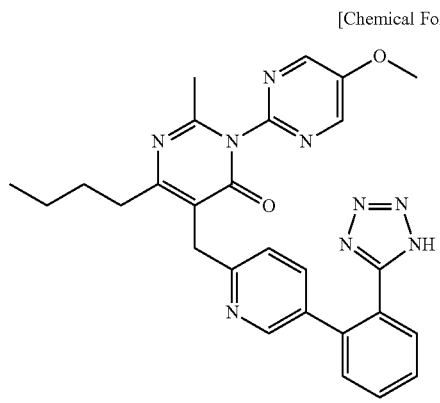

Process 1: By using methyl (Z)-3-acetamide-2-{[5-(2-cyanophenyl)pyridin-2-yl]methyl}-2-heptenoate obtained from the Process 2 of the Example 30 instead of methyl (Z)-3-acetamide-2-{[6-(2-cyanophenyl)pyridin-3-yl]methyl}-2-heptenoate in the Process 3 of the Example 1, the reaction and the treatment were performed in the same manner as the Process 3 of the Example 1 to give 2-{6-{[4-butyl-1-(5-methoxypyrimidin-2-yl)-2-methyl-6-oxo-1,6-dihydropyrimidin-5-yl]methyl}pyridin-3-yl}benzonitrile (yield: 51%) as pale yellow amorphous.

$^1$H-NMR (CDCl$_3$, 400 MHz) δ:
0.93 (3H, t, J=7 Hz), 1.36-1.45 (2H, m), 1.57-1.65 (2H, m), 2.16 (3H, s), 2.75 (2H, t, J=8 Hz), 4.00 (3H, s), 4.17 (2H, s), 7.40-7.49 (3H, m), 7.64-7.69 (1H, m), 7.77-7.79 (2H, m), 8.54 (2H, s), 8.65 (1H, d, J=2 Hz).

Process 2: By using 2-{6-{[4-butyl-1-(5-methoxypyrimidin-2-yl)-2-methyl-6-oxo-1,6-dihydropyrimidin-5-yl]methyl}pyridin-3-yl}benzonitrile instead of 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of the Example 1, the reaction and the treatment were performed in the same manner as the Process 4 of the Example 1 to give 5-{{5-[2-(1H-tetrazol-5-yl)phenyl]pyridin-2-yl}methyl}-6-butyl-3-(5-methoxypyrimidin-2-yl)-2-methylpyrimidin-4(3H)-one (yield: 52%) as pale yellow amorphous.

$^1$H-NMR (CDCl$_3$, 400 MHz) δ:
0.86 (3H, t, J=7 Hz), 1.20-1.29 (2H, m), 1.41-1.49 (2H, m), 2.09 (3H, s), 2.43 (2H, t, J=8 Hz), 3.62 (2H, s), 3.98 (3H, s), 7.00 (1H, d, J=8 Hz), 7.13 (1H, dd, J=8, 2 Hz), 7.39 (1H, d, J=8 Hz), 7.51-7.60 (2H, m), 7.84 (1H, d, J=8 Hz), 7.95 (1H, d, J=2 Hz), 8.48 (2H, s).

Example 34

Preparation of 5-{{5-[2-(1H-tetrazol-5-yl)phenyl]pyridin-2-yl}methyl}-6-butyl-3-(5-ethoxypyrimidin-2-yl)-2-methylpyrimidin-4(3H)-one

[Chemical Formula 41]

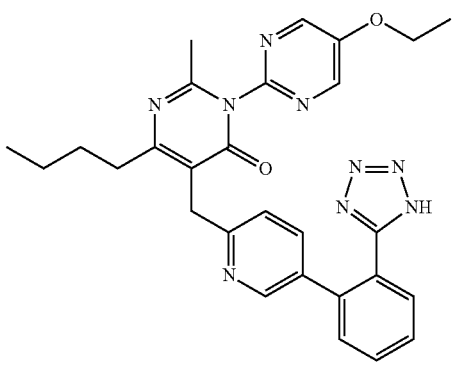

Process 1: By using 2-amino-5-ethoxypyrimidine instead of 2-amino-5-methoxypyrimidine in the Process 3 of the Example 1 and also using methyl (Z)-3-acetamide-2-{[5-(2-cyanophenyl)pyridin-2-yl]methyl}-2-heptenoate obtained from the Process 2 of the Example 30 instead of methyl (Z)-3-acetamide-2-{[6-(2-cyanophenyl)pyridin-3-yl]methyl}-2-heptenoate, the reaction and the treatment were performed in the same manner as the Process 3 of the Example 1 to give 2-{6-{[4-butyl-1-(5-ethoxypyrimidin-2-yl)-2-methyl-6-oxo-1,6-dihydropyrimidin-5-yl]methyl}pyridin-3-yl}benzonitrile (yield: 70%) as pale yellow amorphous.

$^1$H-NMR (CDCl$_3$, 400 MHz) δ:
0.92 (3H, t, J=7 Hz), 1.36-1.45 (2H, m), 1.51 (3H, t, J=7 Hz), 1.57-1.65 (2H, m), 2.16 (3H, s), 2.75 (2H, t, J=8 Hz), 4.18 (2H, s), 4.22 (2H, q, J=7 Hz), 7.41-7.52 (3H, m), 7.64-7.68 (1H, m), 7.77-7.81 (2H, m), 8.52 (2H, s), 8.63-8.65 (1H, m).

Process 2: By using 2-{6-{[4-butyl-1-(5-ethoxypyrimidin-2-yl)-2-methyl-6-oxo-1,6-dihydropyrimidin-5-yl]methyl}pyridin-3-yl}benzonitrile instead of 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of the Example 1, the reaction and the treatment were performed in the same manner as the Process 4 of the Example 1 to give 5-{{5-[2-(1H-tetrazol-5-yl)phenyl]pyridin-2-yl}methyl}-6-butyl-3-(5-ethoxypyrimidin-2-yl)-2-methylpyrimidin-4(3H)-one (yield: 63%) as yellow amorphous.

¹H-NMR (CDCl₃, 400 MHz) δ:
0.86 (3H, t, J=7 Hz), 1.18-1.29 (2H, m), 1.40-1.50 (2H, m), 1.49 (3H, t, J=7 Hz), 2.09 (3H, s), 2.42 (2H, t, J=8 Hz), 3.61 (2H, s), 4.20 (q, 2H, J=7 Hz), 7.00 (1H, d, J=8 Hz), 7.12 (1H, dd, J=8, 2 Hz), 7.39 (1H, d, J=8 Hz), 7.51-7.61 (2H, m), 7.86 (1H, d, J=7 Hz), 7.74 (1H, d, J=2 Hz), 8.46 (2H, s).

Example 35

Preparation of 5-{{5-[2-(1H-tetrazol-5-yl)phenyl]pyridin-2-yl}methyl}-6-butyl-3-(4,6-dimethoxypyrimidin-2-methylpyrimidin-4(3H)-one

[Chemical Formula 42]

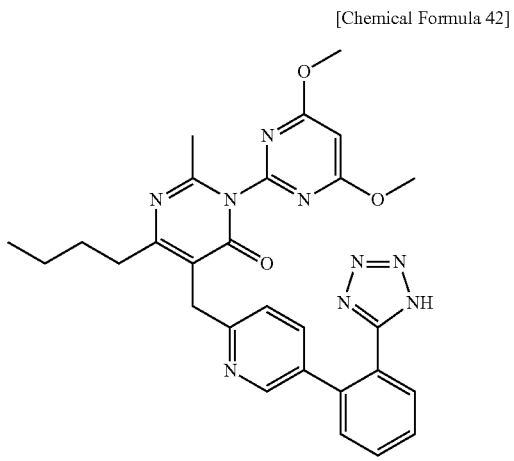 [SMILES: CCCCc1nc(C)n(-c2nc(OC)cc(OC)n2)c(=O)c1Cc1ccc(-c2ccccc2-c2nnn[nH]2)cn1]

Process 1: By using 2-amino-4,6-dimethoxypyrimidine instead of 2-amino-5-methoxypyrimidine in the Process 3 of the Example 1 and also using methyl (Z)-3-acetamide-2-{[5-(2-cyanophenyl)pyridin-2-yl]methyl}-2-heptenoate obtained from the Process 2 of the Example 30 instead of methyl (Z)-3-acetamide-2-{[6-(2-cyanophenyl)pyridin-3-yl]methyl}-2-heptenoate, the reaction and the treatment were performed in the same manner as the Process 3 of the Example 1 to give 2-{6-{[4-butyl-1-(4,6-dimethoxypyrimidin-2-yl)-2-methyl-6-oxo-1,6-dihydropyrimidin-5-yl]methyl}pyridin-3-yl}benzonitrile (yield: 49%) as pale yellow amorphous.

¹H-NMR (CDCl₃, 400 MHz) δ:
0.93 (3H, t, J=7 Hz), 1.38-1.47 (2H, m), 1.56-1.67 (2H, m), 2.24 (3H, s), 2.76 (2H, t, J=8 Hz), 3.96 (6H, s), 4.19 (2H, s), 6.12 (1H, s), 7.45-7.50 (3H, m), 7.65-7.69 (1H, m), 7.77-7.82 (2H, m), 8.66 (1H, d, J=2 Hz).

Process 2: By using 2-{6-{[4-butyl-1-(4,6-dimethoxypyrimidin-2-yl)-2-methyl-6-oxo-1,6-dihydropyrimidin-5-yl]methyl}pyridin-3-yl}benzonitrile instead of 2-{5-{[4-butyl-1-(5-methoxypyrimidin-2-yl)-2-methyl-6-oxo-1,6-dihydropyrimidin-5-yl]methyl}pyridin-2-yl}benzonitrile in the Process 4 of the Example 1, the reaction and the treatment were performed in the same manner as the Process 4 of the Example 1 to give 5-{{5-[2-(1H-tetrazol-5-yl)phenyl]pyridin-2-yl}methyl}-6-butyl-3-(4,6-dimethoxypyrimidin-2-yl)-2-methylpyrimidin-4(3H)-one (yield: 53%) as pale yellow amorphous.

¹H-NMR (CDCl₃, 400 MHz) δ:
0.88 (3H, t, J=7 Hz), 1.22-1.32 (2H, m), 1.43-1.50 (2H, m), 2.17 (3H, s), 2.42 (2H, t, J=8 Hz), 3.62 (2H, s), 3.89 (6H, s), 6.06 (1H, s), 7.02 (1H, d, J=8 Hz), 7.14 (1H, dd, J=8, 2 Hz), 7.40 (1H, d, J=8 Hz), 7.53-7.62 (2H, m), 7.31 (1H, d, J=8 Hz), 7.95 (1H, s).

Example 36

Preparation on 3-{2-{6-{[4-butyl-1-(5-methoxypyridin-2-yl)-2-methyl-6-oxo-1,6-dihydropyrimidin-5-yl]methyl}pyridin-3-yl}phenyl}-1,2,4-oxadiazol-5 (4H)-one

[Chemical Formula 43]

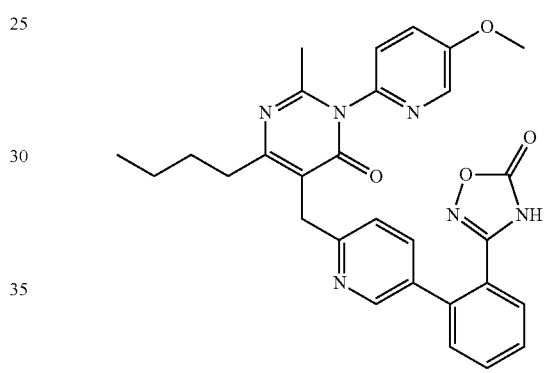

Process 1: By using 2-{6-{[4-butyl-1-(5-methoxypyridin-2-yl)-2-methyl-6-oxo-1,6-dihydropyrimidin-5-yl]methyl}pyridin-3-yl}benzonitrile obtained from the Process 1 of the Example 31 instead of 2-{5-{[4-butyl-2-methyl-6-oxo-1-(pyridin-2-yl)-1,6-dihydropyrimidin-5-yl]methyl}pyridin-2-yl}benzonitrile in the Process 2 of the Example 14, the reaction and the treatment were performed in the same manner as the Process 2 of the Example 14 to give 2-{6-{[4-butyl-1-(5-methoxypyridin-2-yl)-2-methyl-6-oxo-1,6-dihydropyrimidin-5-yl]methyl}pyridin-3-yl}-N'-hydroxybenzimidamide (yield: 64%) as pale yellow amorphous.

¹H-NMR (CDCl₃, 400 MHz) δ:
0.90 (3H, t, J=7 Hz), 1.34-1.43 (2H, m), 1.54-1.62 (2H, m), 2.16 (3H, s), 2.71 (2H, t, J=8 Hz), 3.91 (3H, s), 4.13 (2H, s), 4.50 (2H, s), 7.29-7.42 (5H, m), 7.45-7.49 (1H, m), 7.55-7.57 (1H, m), 7.66-7.69 (1H, m), 8.29 (1H, d, J=3 Hz), 8.60 (1H, d, J=2 Hz).

Process 2: By using 2-{6-{[4-butyl-1-(5-methoxypyridin-2-yl)-2-methyl-6-oxo-1,6-dihydropyrimidin-5-yl]methyl}pyridin-3-yl}-N'-hydroxybenzimidamide instead of 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of the Example 14, the reaction and the treatment were performed in the same manner as the Process 3 of the Example 14 to give 3-{2-{6-{[4-butyl-1-(5-methoxypyridin-2-yl)-2-methyl-6-oxo-1,6-dihydropyrimidin-5-yl]methyl}pyridin-3-yl}phenyl}-1,2,4-oxadiazol-5 (4H)-one (yield: 70%) as pale yellow amorphous.

¹H-NMR (CDCl₃, 400 MHz) δ:
0.92 (3H, t, J=7 Hz), 1.30-1.39 (2H, m), 1.49-1.57 (2H, m), 2.11 (3H, s), 2.51 (2H, t, J=8 Hz), 3.62 (2H, s), 3.91 (3H, s), 7.15 (1H, d, J=8 Hz), 7.23 (2H, d, J=9 Hz), 7.32-7.39 (2H, m), 7.48-7.52 (2H, m), 7.57-7.61 (1H, m), 7.70 (1H, d, J=8 Hz), 7.99 (1H, s), 8.18 (1H, d, J=3 Hz).

Example 37

Preparation of 3-{2-{6-{[4-butyl-1-(5-methoxypyrimidin-2-yl)-2-methyl-6-oxo-1,6-dihydropyrimidin-5-yl]methyl}pyridin-3-yl}phenyl}-1,2,4-oxadiazol-5 (4H)-one

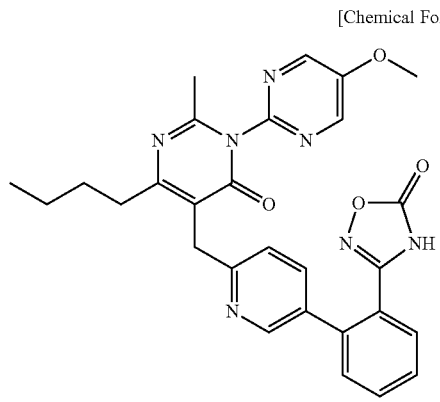

[Chemical Formula 44]

Process 1: By using 2-{6-{[4-butyl-1-(5-methoxypyrimidin-2-yl)-2-methyl-6-oxo-1,6-dihydropyrimidin-5-yl]methyl}pyridin-3-yl}benzonitrile obtained from the Process 1 of the Example 33 instead of 2-{5-{[4-butyl-2-methyl-6-oxo-1-(pyridin-2-yl)-1,6-dihydropyrimidin-5-yl]methyl}pyridin-2-yl}benzonitrile in the Process 2 of the Example 14, the reaction and the treatment were performed in the same manner as the Process 2 of the Example 14 to give 2-{6-{[4-butyl-1-(5-methoxypyrimidin-2-yl)-2-methyl-6-oxo-1,6-dihydropyrimidin-5-yl]methyl}pyridin-3-yl}-N'-hydroxybenzimidamide (yield: 50%) as pale yellow amorphous.

¹H-NMR (CDCl₃, 400 MHz) δ:
0.90 (3H, t, J=7 Hz), 1.34-1.43 (2H, m), 1.54-1.62 (2H, m), 2.15 (3H, s), 2.73 (2H, t, J=8 Hz), 3.99 (3H, s), 4.13 (2H, s), 4.50 (2H, s), 7.28-7.42 (3H, m), 7.45-7.49 (1H, m), 7.53-7.57 (1H, m), 7.66-7.69 (1H, m), 8.53 (2H, s), 8.59 (1H, d, J=2 Hz).

Process 2: By using 2-{6-{[4-butyl-1-(5-methoxypyrimidin-2-yl)-2-methyl-6-oxo-1,6-dihydropyrimidin-5-yl]methyl}pyridin-3-yl}-N'-hydroxybenzimidamide instead of 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of the Example 14, the reaction and the treatment were performed in the same manner as the Process 3 of the Example 14 to give 3-{2-{6-{[4-butyl-1-(5-methoxypyrimidin-2-yl)-2-methyl-6-oxo-1,6-dihydropyrimidin-5-yl]methyl}pyridin-3-yl}phenyl}-1,2,4-oxadiazol-5 (4H)-one (yield: 85%) as pale yellow amorphous.

¹H-NMR (CDCl₃, 400 MHz) δ:
0.90 (3H, t, J=7 Hz), 1.27-1.36 (2H, m), 1.45-1.53 (2H, m), 2.11 (3H, s), 2.45 (2H, t, J=8 Hz), 3.56 (2H, s), 4.00 (3H, s), 7.12 (1H, d, J=8 Hz), 7.38 (1H, d, J=8 Hz), 7.50-7.60 (2H, m), 7.60-7.64 (1H, m), 7.72 (1H, d, J=1 Hz), 7.90 (1H, s), 8.51 (2H, s).

Example 38

Preparation of 3-{2-{6-{[4-butyl-1-(5-ethoxypyrimidin-2-yl)-2-methyl-6-oxo-1,6-dihydropyrimidin-5-yl]methyl}pyridin-3-yl}phenyl}-1,2,4-oxadiazol-5 (4H)-one

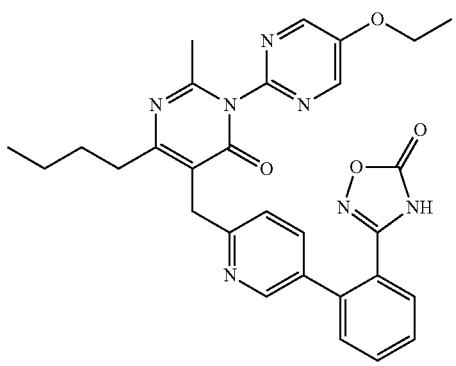

[Chemical Formula 45]

Process 1: By using 2-{6-{[4-butyl-1-(5-ethoxypyrimidin-2-yl)-2-methyl-6-oxo-1,6-dihydropyrimidin-5-yl]methyl}pyridin-3-yl}benzonitrile obtained from the Process 1 of the Example 34 instead of 2-{5-{[4-butyl-2-methyl-6-oxo-1-(pyridin-2-yl)-1,6-dihydropyrimidin-5-yl]methyl}pyridin-2-yl}benzonitrile in the Process 2 of the Example 14, the reaction and the treatment were performed in the same manner as the Process 2 of the Example 14 to give 2-{6-{[4-butyl-1-(5-ethoxypyrimidin-2-yl)-2-methyl-6-oxo-1,6-dihydropyrimidin-5-yl]methyl}pyridin-3-yl}-N'-hydroxybenzimidamide (yield: 52%) as pale yellow amorphous.

¹H-NMR (CDCl₃, 400 MHz) δ:
0.90 (3H, t, J=7 Hz), 1.35-1.43 (2H, m), 1.50 (3H, t, J=7 Hz), 1.51-1.62 (2H, m), 2.15 (3H, s), 2.72 (2H, t, J=8 Hz), 4.13 (2H, s), 4.21 (2H, q, J=7 Hz), 4.51 (2H, s), 7.28-7.49(4H, m), 7.55-7.57 (1H, m), 7.66-7.69 (1H, m), 8.50 (2H, s), 8.59-8.60 (1H, m).

Process 2: By using 2-{6-{[4-butyl-1-(5-ethoxypyrimidin-2-yl)-2-methyl-6-oxo-1,6-dihydropyrimidin-5-yl]methyl}pyridin-3-yl}-N'-hydroxybenzimidamide instead of 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of the Example 14, the reaction and the treatment were performed in the same manner as the Process 3 of the Example 14 to give 3-{2-{6-{[4-butyl-1-(5-ethoxypyrimidin-2-yl)-2-methyl-6-oxo-1,6-dihydropyrimidin-5-yl]methyl}pyridin-3-yl}phenyl}-1,2,4-oxadiazol-5 (4H)-one (yield: 89%) as pale yellow amorphous.

¹H-NMR (CDCl₃, 400 MHz) δ:
0.90 (3H, t, J=7 Hz), 1.27-1.36 (2H, m), 1.45-1.52 (5H, m), 2.11 (3H, s), 2.49 (2H, t, J=8 Hz), 3.59 (2H, s), 4.22 (2H, q,

J=7 Hz), 7.18 (1H, d, J=8 Hz), 7.38 (1H, d, J=8 Hz), 7.50-7.55 (2H, m), 7.60-7.64 (1H, m), 7.72 (1H, d, J=8 Hz), 7.93-7.97 (1H, m), 8.49 (2H, s).

Example 39

Preparation of 3-{2-{6-{[4-butyl-1-(4,6-dimethoxypyrimidin-2-yl)-2-methyl-6-oxo-1,6-dihydropyrimidin-5-yl]methyl}pyridin-3-yl}phenyl}-1,2,4-oxadiazol-5(4H)-one

[Chemical Formula 46]

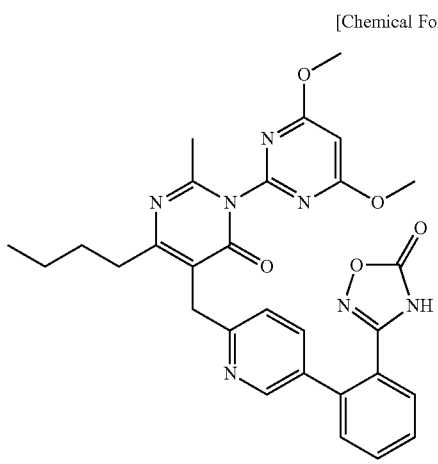

Process 1: By using 2-{6-{[4-butyl-1-(4,6-dimethoxypyrimidin-2-yl)-2-methyl-6-oxo-1,6-dihydropyrimidin-5-yl]methyl}pyridin-3-yl}benzonitrile in the Process 1 of the Example 35 instead of 2-{5-{[4-butyl-2-methyl-6-oxo-1-(pyridin-2-yl)-1,6-dihydropyrimidin-5-yl]methyl}pyridin-2-yl}benzonitrile in the Process 2 of the Example 14, the reaction and the treatment were performed in the same manner as the Process 2 of the Example 14 to give 2-{6-{[4-butyl-1-(4,6-dimethoxypyrimidin-2-yl)-2-methyl-6-oxo-1,6-dihydropyrimidin-5-yl]methyl}pyridin-3-yl}-N'-hydroxybenzimidamide (yield: 47%) as pale yellow amorphous.

$^1$H-NMR (CDCl$_3$, 400 MHz) δ:

0.92 (3H, t, J=7 Hz), 1.36-1.45 (2H, m), 1.56-1.64 (2H, m), 2.23 (3H, s), 2.73 (2H, t, J=8 Hz), 3.95 (6H, s), 4.14 (2H, s), 4.49 (2H, s), 6.12 (1H, s), 7.32-7.43 (3H, m), 7.46-7.50 (1H, m), 7.56-7.58 (1H, m), 7.69-7.71 (1H, m), 8.57-8.61 (1H, m).

Process 2: By using 2-{6-{[4-butyl-1-(4,6-dimethoxypyrimidin-2-yl)-2-methyl-6-oxo-1,6-dihydropyrimidin-5-yl]methyl}pyridin-3-yl}-N'-hydroxybenzimidamide instead of 2-{5-{[4-butyl-2-methyl-6-oxo-1-(pyridin-2-yl)-1,6-dihydropyrimidin-5-yl]methyl}pyridin-2-yl}-N'-hydroxybenzimidamide in the Process 3 of the Example 14, the reaction and the treatment were performed in the same manner as the Process 3 of the Example 14 to give 3-{2-{6-{[4-butyl-1-(4,6-dimethoxypyrimidin-2-yl)-2-methyl-6-oxo-1,6-dihydropyrimidin-5-yl]methyl}pyridin-3-yl}phenyl}-1,2,4-oxadiazol-5(4H)-one (yield: 52%) as pale yellow amorphous.

$^1$H-NMR (CDCl$_3$, 400 MHz) δ:

0.92 (3H, t, J=7 Hz), 1.31-1.40 (2H, m), 1.50-1.58 (2H, m), 2.18 (3H, s), 2.51 (2H, t, J=8 Hz), 3.67 (2H, s), 3.92 (6H, s), 6.08 (1H, s), 7.21 (1H, d, J=8 Hz), 7.41 (1H, d, J=8 Hz), 7.50-7.56 (2H, m), 7.63 (1H, t, J=8 Hz), 7.74 (1H, d, J=8 Hz), 8.01 (1H, d, J=2 Hz).

Example 40

Preparation of 3-{2-{5-{[1-(5-ethoxypyrimidin-2-yl)-2-isopropyl-6-oxo-4-propyl-1,6-dihydropyrimidin-5-yl]methyl}pyridin-2-yl}phenyl}-1,2,4-oxadiazol-5(4H)-one

[Chemical Formula 47]

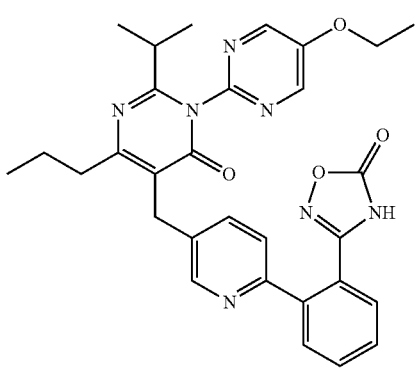

Process 1: Under argon atmosphere, tetrahydrofuran (20 mL) mixture containing 2-[5-(bromomethyl)pyridin-2-yl]benzonitrile (1.1 g, 3.9 mmol), methyl 3-oxohexanoate (0.68 g, 4.7 mmol), diisopropylethylamine (1.0 g, 7.8 mmol), and lithium bromide monohydrate (0.49 g, 4.7 mmol) was refluxed under heating for 18 hours. The reaction mixture was added water and extracted three times with chloroform. The organic layer was combined, washed with water and brine, dried over anhydrous sodium sulfate, and concentrated in vacuo. The obtained residues were subjected to silica gel column chromatography (SNAP100HP manufactured by Biotage) (hexane/ethyl acetate; 5/1→1/1) to give methyl 2-{[6-(2-cyanophenyl)pyridin-3-yl]methyl}-3-oxohexanoate (1.2 g, 91%) as yellow oil.

$^1$H-NMR (CDCl$_3$, 400 MHz) δ:

0.87 (3H, t, J=7.4 Hz), 1.50-1.55 (2H, m), 2.36-2.68 (2H, m), 3.21-3.27 (2H, m), 3.73 (3H, s), 3.84 (1H, t, J=7.6 Hz), 7.50 (1H, td, J=7.6, 1.4 Hz), 7.64-7.73 (3H, m), 7.77-7.85 (2H, m), 8.61 (1H, br s).

Process 2: A toluene (45 mL)-acetic acid (5 mL) mixture containing methyl 2-{[6-(2-cyanophenyl)pyridin-3-yl]methyl}-3-oxohexanoate (1.2 g, 3.6 mmol) and ammonium acetate (8.3 g, 108 mmol) was refluxed under heating for 1 hour. After cooling to room temperature, saturated aqueous solution of sodium hydrogen carbonate was added and extraction was carried out with toluene. After washing with brine, it was dried over anhydrous sodium sulfate and concentrated in vacuo to give methyl (Z)-3-amino-2-{[6-(2-cyanophenyl)pyridin-3-yl]methyl}-2-hexenoate (1.15 g) as brown oil crude product. It was used for the next process without purification.

Process 3: Isobutyryl chloride (219 mg, 2.06 mmol) and triethylamine (208 mg, 2.06 mmol) were added to 1,2-dichloroethane (10 mL) solution of methyl (Z)-3-amino-2-{[6-(2-cyanophenyl)pyridin-3-yl]methyl}-2-hexenoate (575 mg) and stirred for 16 hours at 50° C. The reaction mixture was added water and extracted with chloroform. The organic layer was combined, washed with brine, dried over anhydrous sodium sulfate, and concentrated in vacuo. The obtained residues were subjected to silica gel column chromatography (SNAP50HP manufactured by Biotage) (hexane/ethyl acetate; 5/1→1/1) to give methyl (Z)-2-{[6-(2-cyanophenyl)pyridin-3-yl]methyl}-3-isobutylamide-2-hexenoate (158 mg, 23%; two step yield) as black oil.

$^1$H-NMR (CDCl$_3$, 400 MHz) δ:

0.99 (3H, t, J=7.4 Hz), 1.19-1.29 (8H, m), 2.49-2.62 (1H, m), 2.88-2.97 (2H, m), 3.71 (3H, s), 3.76 (2H, s), 7.51 (1H, dd, J=7.6, 1.3 Hz), 7.59 (1H, dd, J=8.1, 2.1 Hz), 7.64-7.73 (2H, m), 7.77-7.86 (2H, m), 8.60 (1H, s), 11.90 (1H, s).

Process 4: Under argon atmosphere, trimethylaluminum (2 mol/L hexane solution, 0.39 mL, 0.78 mmol) was added to 1,2-dichloroethane (5 mL) solution of 2-amino-5-ethoxypyrimidine (108 mg, 0.78 mmol) at room temperature and stirred for 70 minutes at room temperature. 1,2-dichloroethane solution (2 mL) of methyl (Z)-2-{[6-(2-cyanophenyl)pyridin-3-yl]methyl}-3-isobutylamide-2-hexenoate (158 mg, 0.39 mmol) was added dropwise thereto at room temperature and refluxed under heating for 3 hours. The reaction mixture was added an aqueous solution of ammonium chloride and chloroform, and filtered through a pad of celite. The organic layer in the filtrate was separated and the aqueous layer was extracted with chloroform. The organic layer was combined, washed with water and brine, dried over anhydrous sodium sulfate, and concentrated in vacuo. The obtained residues were subjected to silica gel column chromatography (Flash12M manufactured by Biotage) (chloroform/methanol=40:1) to give 2-{5-{[1-(5-ethoxypyrimidin-2-yl)-2-isopropyl-6-oxo-4-propyl-1,6-dihydropyrimidin-5-yl]methyl}pyridin-2-yl}benzonitrile (111 mg, 58%) as yellow oil.

$^1$H-NMR (CDCl$_3$, 400 MHz) δ:

0.97 (3H, t, J=7.4 Hz), 1.17 (6H, d, J=6.6 Hz), 1.49 (3H, t, J=6.9 Hz), 1.66-1.77 (2H, m), 2.19-2.32 (1H, m), 2.60-2.70 (2H, m), 3.93 (2H, s), 4.10 (2H, q, J=7.1 Hz), 7.45 (1H, td, J=7.7, 1.1 Hz), 7.60-7.67 (2H, m), 7.73-7.80 (3H, m), 8.49 (2H, s), 8.67 (1H, d, J=1.3 Hz).

Process 5: Sodium hydrogen carbonate (1.19 g, 14.1 mmol) was added to dimethyl sulfoxide (15 mL) mixture of hydroxylamine hydrochloride (838 mg, 12.1 mmol) and stirred for 1 hour at 40° C. The reaction mixture was added dimethyl sulfoxide (15 mL) solution of 2-{5-{[1-(5-ethoxypyrimidin-2-yl)-2-isopropyl-6-oxo-4-propyl-1,6-dihydropyrimidin-5-yl]methyl}pyridin-2-yl}benzonitrile (353 mg, 0.71 mmol) and stirred for 18 hours at 90° C. The reaction mixture was added water (80 mL) and ethyl acetate (20 mL) and stirred for 30 minutes. The precipitated solid was collected by filtration and washed with water and ethyl acetate. It was then dried in vacuo to give 2-{5-{[1-(5-ethoxypyrimidin-2-yl)-2-isopropyl-6-oxo-4-propyl-1,6-dihydropyrimidin-5-yl]methyl}pyridin-2-yl}-N'-hydroxybenzimidamide (214 mg, 57%) as a white solid.

$^1$H-NMR (CDCl$_3$, 400 MHz) δ:

0.98 (3H, t, J=7.3 Hz), 1.19 (6H, d, J=6.6 Hz), 1.51 (3H, t, J=7.0 Hz), 1.68-1.78 (2H, m), 2.25-2.32 (1H, m), 2.63-2.70 (2H, m), 3.92 (2H, s), 4.22 (2H, q, J=6.9 Hz), 4.72 (2H, br s), 7.40 (1H, td, J=7.5, 1.3 Hz), 7.43 (1H, d, J=8.5 Hz), 7.49 (1H, td, J=7.6, 1.5 Hz), 7.55 (1H, dd, J=7.6, 1.2 Hz), 7.58 (1H, dd, J=7.8, 1.2 Hz), 7.66 (1H, dd, J=8.2, 2.3 Hz), 8.51 (2H, s), 8.60 (1H, d, J=1.7 Hz).

Process 6: 1,1'-Carbonyldiimidazole (130 mg, 0.80 mmol) and 1,8-diazabicyclo[5.4.0]undeca-7-ene (122 mg, 0.80 mmol) were added to dichloromethane (4 mL) and tetrahydrofuran (4 mL) mixture solution of 2-{5-{[1-(5-ethoxypyrimidin-2-yl)-2-isopropyl-6-oxo-4-propyl-1,6-dihydropyrimidin-5-yl]methyl}pyridin-2-yl}-N'-hydroxybenzimidamide (212 mg, 0.40 mmol) and stirred for 3 hours at room temperature. Once the reaction is completed, 1 M hydrochloric acid solution was added to the reaction mixture, which was then extracted with chloroform. The organic layer was washed with water, dried over anhydrous sodium sulfate, and concentrated in vacuo. The obtained residues were subjected to silica gel column chromatography (chloroform/methanol=20:1) to give 3-{2-{5-{[1-(5-ethoxypyrimidin-2-yl)-2-isopropyl-6-oxo-4-propyl-1,6-dihydropyrimidin-5-yl]methyl}pyridin-2-yl}phenyl}-1,2,4-oxadiazol-5(4H)-one (201 mg, 91%) as white amorphous.

$^1$H-NMR (CDCl$_3$, 400 MHz) δ:

1.01 (3H, t, J=7.3 Hz), 1.19 (6H, d, J=6.6 Hz), 1.51 (3H, t, J=7.0 Hz), 1.71-1.82 (2H, m), 2.26-2.32 (1H, m), 2.66-2.73 (2H, m), 3.95 (2H, s), 4.22 (2H, q, J=7.0 Hz), 7.39 (1H, d, J=8.1 Hz), 7.45 (1H, d, J=8.1 Hz), 7.51 (1H, t, J=7.6 Hz), 7.60 (1H, t, J=7.7 Hz), 7.83 (1H, dd, J=8.1, 1.7 Hz), 7.93 (1H, d, J=7.8 Hz), 8.51 (2H, s), 8.56 (1H, s).

Example 41

Preparation of 3-{2-{5-{[2-cyclopropyl-1-(5-ethoxypyrimidin-2-yl)-6-oxo-4-propyl-1,6-dihydropyrimidin-5-yl]methyl}pyridin-2-yl}phenyl}-1,2,4-oxadiazol-5(4H)-one

[Chemical Formula 48]

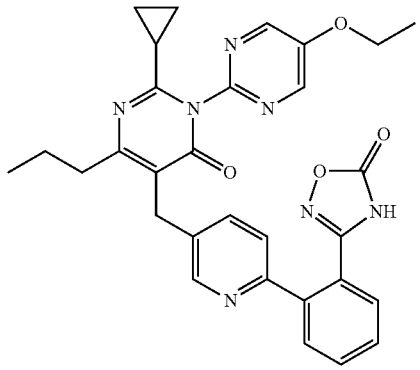

Process 1: By using cyclopropylcarbonyl chloride instead of isobutyryl chloride in the Process 3 of the Example 40, the reaction and the treatment were performed in the same manner as the Process 3 of the Example 40 to give methyl (Z)-2-{[6-(2-cyanophenyl)pyridin-3-yl]methyl}-3-cyclopropanecarboxyamide-2-hexenoate (yield: 58%).

$^1$H-NMR(CDCl$_3$, 400 MHz) δ:

0.83-1.10 (8H, m), 1.58-1.62 (2H, m), 2.87-2.96 (2H, m), 3.71 (3H, s), 3.76 (2H, s), 7.49 (1H, td, J=7.6, 1.3 Hz), 7.58 (1H, dd, J=8.1, 2.1 Hz), 7.65-7.72 (2H, m), 7.77-7.86 (2H, m), 8.61 (1H, s), 12.15 (1H, s).

Process 2: By using methyl (Z)-2-{[6-(2-cyanophenyl)pyridin-3-yl]methyl}-3-(cyclopropanecarboxyamide)-2-hexenoate instead of methyl (Z)-2-{[6-(2-cyanophenyl)pyridin-3-yl]methyl}-3-isobutylamide-2-hexenoate in the Process 4 of the Example 40, the reaction and the treatment were performed in the same manner as the Process 4 of the Example 40 to give 2-{5-{[2-cyclopropyl-1-(5-ethoxypyrimidin-2-yl)-6-oxo-4-propyl-1,6-dihydropyrimidin-5-yl]methyl}pyridin-2-yl}benzonitrile (yield: 58%).

$^1$H-NMR (CDCl$_3$, 400 MHz) δ:

0.80-0.87 (2H, m), 0.96 (3H, t, J=7.5 Hz), 1.08-1.14 (1H, m), 1.21-1.25 (2H, m), 1.51 (3H, t, J=7.0 Hz), 1.61-1.72 (2H, m), 2.57-2.61 (2H, m), 3.94 (2H, s), 4.22 (2H, q, J=6.9 Hz), 7.47 (1H, td, J=7.6, 1. Hz), 7.63-7.69 (2H, m), 7.74-7.82 (3H, m), 8.54 (2H, s), 8.68 (1H, d, J=1.8 Hz).

Process 3: By using 2-{5-{[2-cyclopropyl-1-(5-ethoxypyrimidin-1-yl)-6-oxo-4-propyl-1,6-dihydropyrimidin-5-yl]methyl}pyridin-2-yl}benzonitrile instead of 2-{5-{[1-(5-ethoxypyrimidin-2-yl)-2-isopropyl-6-oxo-4-propyl-1,6-dihydropyrimidin-5-yl]methyl}pyridin-2-yl}benzonitrile in the Process 5 of the Example 40, the reaction and the treatment were performed in the same manner as the Process 5 of the Example 40 to give 2-{5-{[2-cyclopropyl-1-(5-ethoxypyrimidin-2-yl)-6-oxo-4-propyl-1,6-dihydropyrimidin-5-yl]methyl}pyridin-2-yl}-N'-hydroxybenzimidamide (yield: 67%).

$^1$H-NMR (CDCl$_3$, 400 MHz) δ:
0.79-0.88 (2H, m), 0.94 (3H, t, J=7.4 Hz), 1.06-1.15 (1H, m), 1.19-0.26 (2H, m), 1.51 (3H, t, J=7.1 Hz), 1.59-1.71 (2H, m), 2.53-2.64 (2H, m), 3.91 (2H, s), 4.22 (2H, q, J=7.0 Hz), 4.73 (2H, s), 7.40 (1H, td, J=7.3, 1.6 Hz), 7.43 (1H, d, J=7.6 Hz), 7.49 (1H, td, J=7.6, 1.5 Hz), 7.55 (1H, dd, J=7.6, 1.0 Hz), 7.58 (1H, dd, J=7.7, 0.9 Hz), 7.64 (1H, dd, J=8.2, 2.3 Hz), 8.54 (2H, s), 8.59 (1H, d, J=2.2 Hz).

Process 4: By using 2-{5-{[2-cyclopropyl-1-(5-ethoxypyrimidin-2-yl)-6-oxo-4-propyl-1,6-dihydropyrimidin-5-yl]methyl}pyridin-2-yl}-N'-hydroxybenzimidamide instead of 2-{5-{[1-(5-ethoxypyrimidin-2-yl)-2-isopropyl-6-oxo-4-propyl-1,6-dihydropyrimidin-5-yl]methyl}pyridin-2-yl}-N'-hydroxybenzimidamide in the Process 6 of the Example 40, the reaction and the treatment were performed in the same manner as the Process 6 of the Example 40 to give 3-{2-{5-{[2-cyclopropyl-1-(5-ethoxypyrimidin-2-yl)-6-oxo-4-propyl-1,6-dihydropyrimidin-5-yl]methyl}pyridin-2-yl}phenyl}-1,2,4-oxadiazol-5(4H)-one (yield: 94%) as white amorphous.

$^1$H-NMR (CDCl$_3$, 400 MHz) δ:
0.81-0.89 (1H, m), 0.97 (3H, t, J=7.4 Hz), 1.06-1.15 (1H, m), 1.21-1.27 (2H, m), 1.51 (3H, t, J=7.0 Hz), 1.66-1.70 (2H, m), 2.61 (2H, t, J=7.4 Hz), 3.94 (2H, s), 4.22 (2H, q, J=6.8 Hz), 7.39 (1H, d, J=0.3 Hz), 7.45 (1H, d, J=7.6 Hz), 7.52 (1H, t, J=7.6 Hz), 7.60 (1H, t, J=7.2 Hz), 7.81 (1H, dd, J=7.9, 1.8 Hz), 7.94 (1H, d, J=7.8 Hz), 8.54 (2H, s), 8.55 (1H, s).

Example 42

Preparation of 3-{2-{5-{[1-(5-ethoxypyrimidin-2-yl)-2-isopropyl-6-oxo-4-pentyl-1,6-dihydropyrimidin-5-yl]methyl}pyridin-2-yl}phenyl}-1,2,4-oxadiazol-5(4H)-one

[Chemical Formula 49]

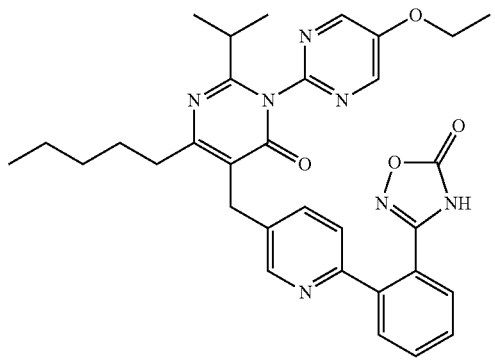

Process 1: By using methyl 3-oxooctanoate instead of methyl 3-oxohexanoate in the Process 1 of the Example 40, the reaction and the treatment were performed in the same manner as the Process 1 of the Example 40 to give methyl 2-{[6-(2-cyanophenyl)pyridin-3-yl]methyl}-3-oxooctanoate (yield: 38%).

$^1$H-NMR (CDCl$_3$, 400 MHz) δ:
0.86 (3H, t, J=6.9 Hz), 1.19-1.32 (4H, m), 1.49-1.55 (2H, m), 2.35-2.67 (2H, m), 3.20-3.26 (2H, m), 3.73 (3H, s), 3.84 (1H, t, J=7.4 Hz), 7.50 (1H, td, J=7.6, 1.3 Hz), 7.64-7.73 (3H, m), 7.77-7.85 (2H, m), 8.61 (1H, br s).

Process 2: By using methyl 2-{[6-(2-cyanophenyl)pyridin-3-yl]methyl}-3-oxooctanoate instead of methyl 2-{[6-(2-cyanophenyl)pyridin-3-yl]methyl}-3-oxohexanoate in the Process 2 of the Example 40, the reaction and the treatment were performed in the same manner as the Process 2 of the Example 40 to give methyl (Z)-3-amino-2-{[6-(2-cyanophenyl)pyridin-3-yl]methyl}-2-octenoate (yield: 82%) as brown oil crude product. It was used for the next process without purification.

Process 3: By using methyl (Z)-3-amino-2-{[6-(2-cyanophenyl)pyridin-3-yl]methyl}-2-octenoate instead of methyl (Z)-3-amino-2-{[6-(2-cyanophenyl)pyridin-3-yl]methyl}-2-hexenoate in the Process 3 of the Example 40, the reaction was performed in the same manner as the Process 3 of the Example 40. According to a post-treatment carried out in the same manner as the Process 3 of the Example 40, methyl (Z)-2-{[6-(2-cyanophenyl)pyridin-3-yl]methyl}-3-isobutylamide-2-octenoate was obtained as a crude product. It was used for the next process without purification.

Process 4: By using methyl (Z)-2-{[6-(2-cyanophenyl)pyridin-3-yl]methyl}-3-isobutylamide-2-octenoate instead of methyl (Z)-2-{[6-(2-cyanophenyl)pyridin-3-yl]methyl}-3-isobutylamide-2-hexenoate in the Process 4 of the Example 40, the reaction and the treatment were performed in the same manner as the Process 4 of the Example 40 to give 2-{5-{[1-(5-ethoxypyrimidin-2-yl)-2-isopropyl-6-oxo-4-pentyl-1,6-dihydropyrimidin-5-yl]methyl}pyridin-2-yl}benzonitrile (yield: 86%).

$^1$H-NMR (CDCl$_3$, 400 MHz) δ:
0.90 (3H, t, J=6.8 Hz), 1.20 (6H, d, J=6. Hz), 1.32-1.39 (4H, m), 1.51 (3H, t, J=7.0 Hz), 1.65-1.75 (2H, m), 2.24-2.33 (1H, m), 2.65-2.71 (2H, m), 3.95 (2H, s), 4.22 (2H, q, J=7.0 Hz), 7.47 (1H, td, J=7.6, 1.1 Hz), 7.63-7.69 (2H, m), 7.76-7.82 (3H, m), 8.51 (2H, s), 8.70 (1H, d, J=1.5 Hz).

Process 5: By using 2-{5-{[1-(5-ethoxypyrimidin-2-yl)-2-isopropyl-6-oxo-4-pentyl-1,6-dihydropyrimidin-5-yl]methyl}pyridin-2-yl}benzonitrile instead of 2-{5-{[1-(5-ethoxypyrimidin-2-yl)-2-isopropyl-6-oxo-4-propyl-1,6-dihydropyrimidin-5-yl]methyl}pyridin-2-yl}benzonitrile in the Process 5 of the Example 40, the reaction and the treatment were performed in the same manner as the Process 5 of the Example 40 to give 2-{5-{[1-(5-ethoxypyrimidin-2-yl)-2-isopropyl-6-oxo-4-pentyl-1,6-dihydropyrimidin-5-yl]methyl}pyridin-2-yl}-N'-hydroxybenzimidamide (yield: 59%).

$^1$H-NMR (CDCl$_3$, 400 MHz) δ:
0.90 (3H, t, J=7.0 Hz), 1.21 (6H, t, J=12.2 Hz), 1.30-1.39 (4H, m), 1.51 (3H, t, J=7.0 Hz), 1.65-1.74 (2H, m), 2.25-2.32 (1H, m), 2.68 (2H, t, J=7.6 Hz), 3.92 (2H, s), 4.22 (2H, q, J=7.0 Hz), 4.73 (2H, br s), 7.40 (1H, td, J=7.6, 1.4 Hz), 7.43 (1H, d, J=8.5 Hz), 7.49 (1H, td, J=7.5, 1.3 Hz), 7.55 (1H, dd, J=7.6, 1.2 Hz), 7.58 (1H, dd, J=7.6, 12 Hz), 7.66 (1H, dad, J=8.2, 2.3 Hz), 8.51 (2H, s), 8.59 (1H, d, J=2.0 Hz).

Process 6: By using 2-{5-{[1-(5-ethoxypyrimidin-2-yl)-2-isopropyl-6-oxo-4-pentyl-1,6-dihydropyrimidin-5-yl]methyl}pyridin-2-yl}-N'-hydroxybenzimidamide instead of 2-{5-{[1-(5-ethoxypyrimidin-2-yl)-2-isopropyl-6-oxo-4-propyl-1,6-dihydropyrimidin-5-yl]methyl}pyridin-2-yl}-N'-hydroxybenzimidamide in the Process 6 of the Example 40, the reaction and the treatment were performed in the same manner as the Process 6 of the Example 40 to give 3-{2-{5-{[1-(5-ethoxypyrimidin-2-yl)-2-isopropyl-6-oxo-4-pentyl-1,6-dihydropyrimidin-1-yl]methyl}pyridin-2-yl}phenyl}1,2,4-oxadiazol-5(4H)-one (yield: 99%).

$^1$H-NMR (CDCl$_3$, 400 MHz) δ:
0.90 (3H, t, J=7.0 Hz), 1.20 (6H, d, J=6.6 Hz), 1.31-1.42 (4H, m), 1.51 (3H, t, J=7.1 Hz), 1.67-1.77 (2H, m), 2.26-2.32 (1H, m), 2.71 (2H, t, J=7.6 Hz), 3.95 (2H, s), 4.22 (2H, q, J=7.0 Hz), 7.41 (1H, d, J=8.1 Hz), 7.45 (1H, dd, J=7.8, 1.2 Hz), 7.53 (1H, td, J=7.7, 1.2 Hz), 7.61 (1, td, J=7.6, 1.5 Hz), 7.84 (1H, d, J=8.3 Hz), 7.97 (1H, d, J=7.6 Hz), 8.51 (2H, s), 8.59 (1H, s).

Example 43

Preparation of 3-{2-{5-{[2-cyclopropyl-1-(5-ethoxypyrimidin-2-yl)-6-oxo-4-pentyl-1,6-dihydropyrimidin-5-yl]methyl}pyridin-2-yl}phenyl}-1,2,4-oxadiazol-5(4H)-one

[Chemical Formula 50]

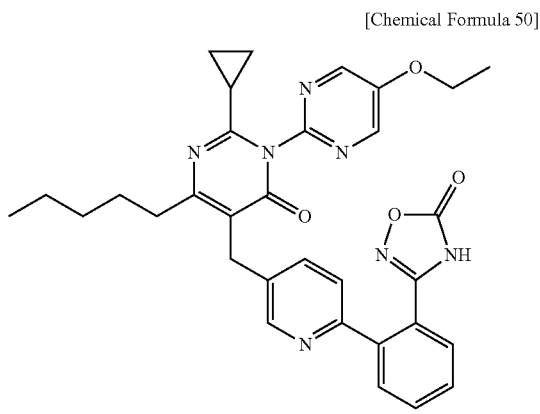 [SMILES: CCCCCc1nc(C2CC2)n(-c2ncc(OCC)cn2)c(=O)c1Cc1ccc(-c2ccccc2-c2noc(=O)[nH]2)nc1]

Process 1: By using cyclopropanecarbonyl chloride instead of isobutyryl chloride in the Process 3 of the Example 40 and also using methyl (Z)-3-amino-2-{[6-(2-cyanophenyl)pyridin-3-yl]methyl}-2-octenoate instead of methyl (Z)-3-amino-2-{[6-(2-cyanophenyl)pyridin-3-yl]methyl}-2-hexenoate, the reaction was performed in the same manner as the Process 3 of the Example 40. According to a post-treatment carried out in the same manner as the Process 3 of the Example 40, methyl (Z)-2-{[6-(2-cyanophenyl)pyridin-3-yl]methyl}-3-cyclopropanecarboxamide-2-octenoate was obtained as a crude product. It was used for the next process without purification.

Process 2: By using methyl (Z)-2-{[6-(2-cyanophenyl)pyridin-3-yl]methyl}-3-cyclopropanecarboxamide-2-octenoate instead of methyl (Z)-2-{[6-(2-cyanophenyl)pyridin-3-yl]methyl}-3-isobutylamide-2-hexenoate in the Process 4 of the Example 40, the reaction and the treatment were performed in the same manner as the Process 4 of the Example 40 to give 2-{5-{[2-cyclopropyl-1-(5-ethoxypyrimidin-2-yl)-6-oxo-4-pentyl-1,6-dihydropyrimidin-5-yl]methyl}pyridin-2-yl}benzonitrile (yield: 64%).

$^1$H-NMR (CDCl$_3$, 400 MHz) δ:
0.81-0.91 (5H, m), 1.07-1.14 (1H, m), 1.21-1.26 (2H, m), 1.29-1.36 (4H, m), 1.49-1.53 (3H, m), 1.60-1.65 (2H, m), 2.57-2.6 (2H, m), 3.94 (2H, s), 4.2 (2H, q, J=7.1 Hz), 7.44-7.50 (1H, m), 7.63-7.69 (2H, m), 7.73-7.83 (3H, m), 8.54 (2H, s), 8.69 (1H, s).

Process 3: By using 2-{5-{[2-cyclopropyl-1-(5-ethoxypyrimidin-2-yl)-6-oxo-4-pentyl-1,6-dihydropyrimidin-5-yl]methyl}pyridin-2-yl}benzonitrile instead of 2-{5-{[1-(5-ethoxypyrimidin-2-yl)-2-isopropyl-6-oxo-4-propyl-1,6-dihydropyrimidin-5-yl]methyl}pyridin-2-yl}benzonitrile in the Process 5 of the Example 40, the reaction and the treatment were performed in the same manner as the Process 5 of the Example 40 to give 2-{5-{[2-cyclopropyl-1-(5-ethoxypyrimidin-2-yl)-6-oxo-4-pentyl-1,6-dihydropyrimidin-5-yl]methyl}pyridin-2-yl}-N'-hydroxybenzimidamide (yield: 70%).

$^1$H-NMR, (CDCl$_3$, 400 MHz) δ:
0.81-0.86 (2H, m), 0.89 (3H, t, J=6.8 Hz), 1.06-1.15 (1H, m), 1.19-1.25 (2H, m), 1.28-1.35 (4H, m), 1.51 (3H, t, J=7.1 Hz), 1.58-1.65 (2H, m), 2.60 (2H, t, J=7.9 Hz), 3.90 (2H, s), 4.22 (2H, q, J=7.0 Hz), 4.73 (2H, br s), 7.40 (1H, td, J=7.5, 1.5 Hz), 7.43 (1H, d, J=7.8 Hz), 7.49 (1H, td, J=7.6, 1.5 Hz), 7.55 (1H, dd, J=7.6, 1.5 Hz), 7.58 (1H, dd, J=7.9, 1.1 Hz), 7.64 (1H, dd, J=8.1, 2.4 Hz), 8.54 (2H, s), 8.58 (1H, d, J=1.7 Hz).

Process 4: By using 2-{5-{[2-cyclopropyl-1-(5-ethoxypyrimidin-2-yl)-6-oxo-4-pentyl-1,6-dihydropyrimidin-5-yl]methyl}pyridin-2-yl}-N'-hydroxybenzimidamide instead of 2-{5-{[1-(5-ethoxypyrimidin-2-yl)-2-isopropyl-6-oxo-4-propyl-1,6-dihydropyrimidin-5-yl]methyl}pyridin-2-yl}-N'-hydroxybenzimidamide in the Process 6 of the Example 40, the reaction and the treatment were performed in the same manner as the Process 6 of the Example 40 to give 3-{2-{5-{[2-cyclopropyl-1-(5-ethoxypyrimidin-2-yl)-6-oxo-4-pentyl-1,6-dihydropyrimidin-5-yl]methyl}pyridin-2-yl}phenyl}-1,2,4-oxadiazol-5(4H)-one (yield: 91%) as white amorphous.

$^1$H-NMR, (CDCl$_3$, 400 MHz) δ:
0.82-0.93 (5H, m), 1.07-1.15 (1H, m), 1.1-1.27 (2H, m), 1.29-1.38 (4H, m), 1.51 (3H, t, J=7.0 Hz), 1.59-1.70 (2H, m), 2.62 (2H, t, J=7.7 Hz), 3.93 (2H, s), 4.22 (2H, q, J=7.0 Hz), 7.40 (1H, d, J=7.8 Hz), 7.45 (1, d, J=7.6 Hz), 7.53 (1H, td, J=7.6, 1.2 Hz), 7.61 (1H, td, J=7.7, 1.4 Hz), 7.81 (1H, ad, J=7.9, 2.1 Hz), 7.96 (1H, d, J=7.8 Hz), 8.54 (2H, s), 8.57 (1H, s), 7.60 (1H, t, J=7.2 Hz), 7.81 (1H, dd, J=7.9, 1.5 Hz), 7.94 (1H, d, J=7.8 Hz), 8.54 (2H, s), 8.55 (1H, s).

Example 44

Preparation of 3-{2-{5-{[1-(5-ethoxypyrimidin-2-yl)-4-ethyl-2-isopropyl-6-oxo-1,6-dihydropyrimidin-5-yl]methyl}pyridin-2-yl}phenyl}-1,2,4-oxadiazol-5(4H)-one

[Chemical Formula 51]

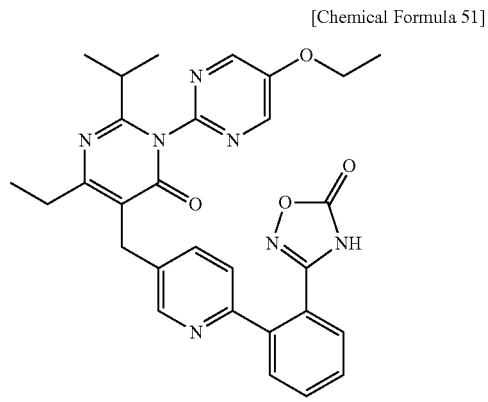 [SMILES: CCOc1cnc(-n2c(C(C)C)nc(CC)c(Cc3ccc(-c4ccccc4-c4noc(=O)[nH]4)nc3)c2=O)nc1]

Process 1: By using methyl 3-oxopentanoate instead of methyl 3-oxohexanoate in the Process 1 of the Example 40, the reaction and the treatment were performed in the same manner as the Process 1 of the Example 40 to give 2-{[6-(2-cyanophenyl)pyridin-3-yl]methyl}-3-oxopentanoate (yield: 43%).

¹H-NMR (CDCl₃, 400 MHz) δ:
1.05 (3H, t, J=7 Hz), 2.44 (1H, dq, J=22, 7 Hz), 2.66 (1H, dq, J=22, 7 Hz), 3.24 (2H, dd, J=7, 7 Hz), 3.73 (3H, s), 3.84 (1H, t, J=7 Hz), 7.50 (1H, dd, J=8, 1 Hz), 7.67-7.70 (3H, m), 7.78 (1H, d, J=8 Hz), 7.83 (1H, d, J=8 Hz), 8.60 (1H, d, J=2 Hz).

Process 2: By using methyl 2-{[6-(2-cyanophenyl)pyridin-3-yl]methyl}-3-oxopentanoate instead of methyl 2-{[6-(2-cyanophenyl)pyridin-3-yl]methyl}-3-oxohexanoate in the Process 2 of the Example 40, the reaction and the treatment were performed in the same manner as the Process 2 of the Example 40 to give methyl (Z)-3-amino-2-{[6-(2-cyanophenyl)pyridin-3-yl]methyl}-2-pentenoate as a crude product. It was used for the next process without purification.

Process 3: By using methyl (Z)-3-amino-2-{[6-(2-cyanophenyl)pyridin-3-yl]methyl}-2-pentenoate instead of methyl (Z)-3-amino-2-{[6-(2-cyanophenyl)pyridin-3-yl]methyl}-2-hexenoate in the Process 3 of the Example 40, the reaction was performed in the same manner as the Process 3 of the Example 40. According to a post-treatment carried out in the same manner as the Process 3 of the Example 40, methyl (Z)-2-{[6-(2-cyanophenyl)pyridin-3-yl]methyl}-3-isobutylamide-2-pentenoate (two step yield: 3.3%) was obtained as a crude product.

¹H-NMR (CDCl₃, 400 MHz) δ:
1.17 (3H, t, J=7 Hz), 1.25 (6H, c, J=7 Hz), 2.57 (1H, sept, J=7 Hz), 3.0 (2H, q, J=7 Hz), 3.71 (3H, s), 3.77 (2H, s), 7.49 (1H, dd, J=8, 1 Hz), 7.60 (1H, dd, J=8, 2 Hz), 7.70 (2H, m), 7.79 (1H, d, J=8 Hz), 7.83 (1H, d, J=8 Hz), 8.61 (1H, d, J=2 Hz), 11.9 (1H, s).

Process 4: By using methyl (Z)-2-{[6-(2-cyanophenyl)pyridin-3-yl]methyl}-3-isobutylamide-2-pentenoate instead of methyl (Z)-2-{[6-(2-cyanophenyl)pyridin-3-yl]methyl}-3-isobutylamide-2-hexenoate in the Process 4 of the Example 40, the reaction and the treatment were performed in the same manner as the Process 4 of the Example 40 to give 2-{5-{[1-(5-ethoxypyrimidin-2-yl)-4-ethyl-2-isopropyl-6-oxo-1,6-dihydropyrimidin-5-yl]methyl}pyridin-2-yl}benzonitrile (yield: 58%).

¹H-NMR (CDCl₃, 400 MHz) δ:
1.20 (6H, d, J=7 Hz), 1.25 (3H, t, J=8 Hz), 1.52 (3H, t, J=7 Hz), 2.29 (1H, sept, J=7 Hz), 2.72 (2H, q, J=8 Hz), 4.0 (2H, s), 4.21 (2H, q, J=7 Hz), 7.47 (1H, dd, J=8, 1 Hz), 7.64-7.68 (2H, m), 7.76-7.78 (3H, m), 8.51 (2H, s), 8.70 (1H, d, J=2 Hz).

Process 5: By using 2-{5-{[1-(5-ethoxypyrimidin-2-yl)-4-ethyl-2-isopropyl-6-oxo-1,6-dihydropyrimidin-5-yl]methyl}pyridin-2-yl}benzonitrile instead of 2-{5-{[1-(5-ethoxypyrimidin-2-yl)-2-isopropyl-6-oxo-4-propyl-1,6-dihydropyrimidin-5-yl]methyl}pyridin-2-yl}benzonitrile in the Process 5 of the Example 40, the reaction and the treatment were performed in the same manner as the Process 5 of the Example 40 to give 2-{5-{[1-(5-ethoxypyrimidin-2-yl)-4-ethyl-2-isopropyl-6-oxo-1,6-dihydropyrimidin-5-yl]methyl}pyridin-2-yl}-N'-hydroxybenzimidamide (yield: 61%).

¹H-NMR (CDCl₃, 400 MHz) δ:
1.19 (6H, d, J=7 Hz), 1.22 (3H, t, J=8 Hz), 1.50 (3H, t, J=7 Hz), 2.29 (1H, sept, J=7 Hz), 2.69 (2H, q, J=8 Hz), 3.91 (2H, s), 4.20 (2H, q, J=7 Hz), 4.78 (2H, br), 7.37-7.40 (2H, m), 7.44-7.51 (2H, m), 7.56 (1H, dd, J=8, 1 Hz), 7.63 (1H, dd, J=, 2 Hz), 8.50 (2H, s), 8.57 (1H, d, J=2 Hz).

Process 6: By using 2-{5-{[1-(5-ethoxypyrimidin-2-yl)-4-ethyl-2-isopopyl-6-oxo-1,6-dihydropyrimidin-5-yl]methyl}pyridin-2-yl}-N'-hydroxybenzimidamide instead of 2-{5-{[1-(5-ethoxypyrimidin-2-yl)-2-isopropyl-6-oxo-4-propyl-1,6-dihydropyrimidin-5-yl]methyl}pyridin-2-yl}-N'-hydroxybenzimidamide in the Process 6 of the Example 40, the reaction and the treatment were performed in the same manner as the Process 6 of the Example 40 to give 3-{2-{5-{[1-(5-ethoxypyrimidin-2-yl)-4-ethyl-2-isopropyl-6-oxo-1,6-dihydropyrimidin-5-yl]methyl}pyridin-2-yl}phenyl}-1,2,4-oxadiazol-5(4H)-one (yield: 56%) as pale yellow amorphous.

¹H-NMR (CDCl₃, 400 MHz) δ:
1.19 (6H, d, J=7 Hz), 1.24 (3H, t, J=8 Hz), 1.51 (3H, t, J=7 Hz), 2.28 (1H, sept, J=7 Hz), 2.69 (2H, q, J=8 Hz), 3.93 (2H, s), 4.22 (2H, q, J=7 Hz), 7.30 (1H, d, J=8 Hz), 7.37-7.41 (2H, m), 7.49 (1H, d, J=8, 1 Hz), 7.67 (1H, d, J=8 Hz), 7.77 (1H, dd, J=8, 2 Hz), 8.39 (1H, d, J=2 Hz), 8.51 (2H, s).

Example 45

Preparation of 3-{2-{5-{[2-cyclopropyl-1-(5-ethoxypyrimidin-2-yl)-4-ethyl-6-oxo-1,6-dihydropyrimidin-5-yl]methyl}pyridin-2-yl}phenyl}-1,2,4-oxadiazol-5(4H)-one

[Chemical Formula 52]

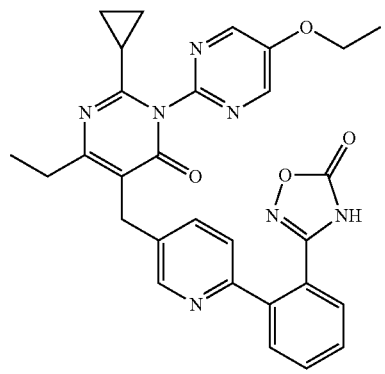

Process 1: By using cyclopropanecarbonyl chloride instead of isobutyryl chloride in the Process 3 of the Example 40 and also using methyl (Z)-3-amino-2-{[6-(2-cyanophenyl)pyridin-3-yl]methyl}-2-pentenoate instead of methyl (Z)-3-amino-2-{[6-(2-cyanophenyl)pyridin-3-yl]methyl}-2-hexenoate, the reaction was performed in the same manner as the Process 3 of the Example 40. According to a post-treatment carried out in the same manner as the Process 3 of the Example 40, methyl (Z)-2-{[6-(2-cyanophenyl)pyridin-3-yl]methyl}-3-cyclopropanecarboxamide-2-pentenoate (two step yield: 3.7%) was obtained as a crude product.

¹H-NMR (CDCl₃, 400 MHz) δ:
0.85-0.90 (2H, m), 1.05-1.08 (3H, m), 1.16 (3H, t, J=8 Hz), 2.98 (2H, q, J=8 Hz), 3.72 (3H, s), 3.77 (2H, s), 7.49 (1H, dd, J=8, 1 Hz), 7.59 (1H, dd, J=8, 2 Hz), 7.66-7.72 (2H, m), 7.79 (1H, d, J=8 Hz), 7.83 (1H, d, J=8 Hz), 8.62 (1H, d, J=2 Hz), 12.1 (1H, s).

Process 2: By using methyl (Z)-2-{[6-(2-cyanophenyl)pyridin-3-yl]methyl}-3-cyclopropanecarboxamide-2-pentenoate instead of methyl (Z)-2-{[6-(2-cyanophenyl)pyridin-3-yl]methyl}-3-isobutylamide-2-hexenoate in the Process 4 of the Example 40, the reaction and the treatment were performed in the same manner as the Process 4 of the Example 40 to give 2-{5-{[2-cyclopropyl-1-(5-ethoxypyrimidin-2-yl)-4-ethyl-6-oxo-1,6-dihydropyrimidin-5-yl]methyl}pyridin-2-yl}benzonitrile (yield: 13%)

$^1$H-NMR (CDCl$_3$, 400 MHz) δ:
0.82-0.88 (2H, m), 1.08-1.15 (1H, m), 1.18 (3H, t, J=8 Hz), 1.23-1.28 (2H, m), 1.50 (3H, t, J=7 Hz), 2.63 (2H, q, J=8 Hz), 3.95 (2H, s), 4.21 (2H, q, J=7 Hz), 7.44-7.48 (1H, m), 7.64-7.66 (2H, m), 7.76-7.78 (3H, m), 8.53 (2H, s), 8.7 (1H, d, J=2 Hz).

Process 3: By using 2-{5-{[2-cyclopropyl-1-(5-ethoxypyrimidin-2-yl)-4-ethyl-6-oxo-1,6-dihydropyrimidin-5-yl]methyl}pyridin-2-yl}benzonitrile instead of 2-{5-{[1-(5-ethoxypyrimidin-2-yl)-2-isopropyl-6-oxo-4-propyl-1,6-dihydropyrimidin-5-yl]methyl}pyridin-2-yl}benzonitrile in the Process 5 of the Example 40, the reaction and the treatment were performed in the same manner as the Process 5 of the Example 40 to give 2-{5-{[2-cyclopropyl-1-(5-ethoxypyrimidin-2-yl)-4-ethyl-6-oxo-1,6-dihydropyrimidin-5-yl]methyl}pyridin-2-yl}-N'-hydroxybenzimiidamide (yield: 52%).

$^1$H-NMR (CDCl$_3$, 400 MHz) δ:
0.82-0.88 (2H, m), 1.04-1.12 (1H, m), 1.15 (3H, t, J=8 Hz), 1.22-1.28 (2H, m), 1.50 (3H, t, J=7 Hz), 2.62 (2H, g, J=8 Hz), 3.90 (2H, s), 4.21 (2H, q, J=7 Hz), 4.76 (2H, br), 7.38-7.40 (2H, m), 7.47-7.51 (2H, m), 7.57 (1H, d, J=8 Hz), 7.61 (1H, d, J=8 Hz), 8.53 (2H, s), 8.57 (1H, s).

Process 4: By using 2-{5-{[2-cyclopropyl-1-(ethoxypyrimidin-2-yl)-4-ethyl-6-oxo-1,6-dihydropyrimidin-5-yl]methyl}pyridin-2-yl}-N'-hydroxybenzimidamide instead of 2-{5-{[1-(5-ethoxypyrimidin-2-yl)-2-isopropyl-6-oxo-4-propyl-1,6-dihydropyrimidin-5-yl]methyl}pyridin-2-yl}-N'-hydroxybenzimidamide in the Process 6 of the Example 40, the reaction and the treatment were performed in the same manner as the Process 6 of the Example 40 to give 3-{2-{5-{[2-cyclopropyl-1-(5-ethoxypyrimidin-2-yl)-4-ethyl-6-oxo-1,6-dihydropyrimidin-5-yl]methyl}pyridin-2-yl}phenyl}-1,2,4-oxadiazol-5(4H)-one (yield: 45%) as pale yellow amorphous.

$^1$H-NMR (CDCl$_3$, 400 MHz) δ:
0.82-0.90 (2H, m), 1.08-1.11 (1H, m), 1.18 (3H, t, J=8 Hz), 1.23-1.26 (2H, m), 1.51 (3H, t, J=7 Hz), 2.63 (2H, q, J=8 Hz), 3.91 (2H, s), 4.21 (2H, q, J=7 Hz), 7.31 (1H, d, J=8 Hz), 7.37-7.44 (2H, m), 7.51 (1H, dd, J=8, 2 Hz), 7.73 (1H, d, J=8 Hz), 7.76 (1H, dd, J=8, 2 Hz), 8.40 (1H, d, J=2 Hz), 8.54 (2H, s)

Test Example 1

Angiotensin II Antagonistic Activity in Isolated Rabbit Blood Vessels

By using a specimen of isolated rabbit blood vessels, antagonistic activity of the compounds of the invention against angiotensin II type 1 receptor was calculated from a dose-response curve of angiotensin II-induced blood vessel contraction. Specifically, the specimen of thoracic aorta ring of a rabbit (New Zealand White: male, 2.4 to 3.0 kg) was suspended in a rmagnus bath filled with Krebs-Henseleite buffer (composition: 118 mM NaCl, 4.7 mM KCl, 2.55 mM CaCl$_2$, 1.18 mM MgSO$_4$, 1.18 mM KH$_2$PO$_4$, 24.88 mM NaHCO$_3$, and 11.1 mM D-glucose), and angiotensin II (10 nM)-induced contraction was obtained in the presence of each test compound (1 n mol/L to 10 μmol/L). During the measurement, the inside temperature of the magnus bath was maintained at 37° C. and the bath was continuously ventilated with a sufficient amount of mixed gas (95% O$_2$ and 5% CO$_2$). The angiotensin II-induced contraction was converted into a relative value (%) that is based on the angiotensin II (0.1 μM)-induced contraction in the absence of the test compound.

As a result, it was confirmed that the compounds described in the Examples have an angiotensin II antagonistic activity at the concentration of 0.1 μM. The inhibitory rate of angiotensin II (10 nM) at the test compound concentration of 0.1 μM is shown in the Table 1. As shown in the Table 1, it was confirmed that the compounds of the invention have a potent angiotensin II antagonistic activity, which is the same as telmisartan. Meanwhile, under the same condition, rate of inhibiting the angiotensin II activity by telmisartan was 85.3%.

TABLE 1

| Example No. | Rate (%) of inhibiting angiotensin II activity at concentration of 0.1 μM |
| --- | --- |
| 1 | 100 |
| 2 | 90.8 |
| 12 | 100 |
| 13 | 100 |
| 14 | 59.3 |
| 15 | 78.3 |
| 16 | 72.9 |
| 17 | 52.1 |
| 21 | 70.3 |
| 22 | 59.5 |
| 23 | 75.2 |
| 28 | 86.5 |
| 29 | 96.3 |
| 40 | 68.3 |
| 41 | 89.9 |

Test Example 2

PPARγ Activation Effect

The agonistic activity of the compounds of the invention on PPARγ was measured based on the transfection assay using COS7 cells (DS Pharma Biomedical Co., Ltd., Osaka, Japan), which are the cell line derived from the kidney of the African green monkey. COS7 cells were cultured under 5% CO$_2$ concentration, and DMEM medium containing 10% fetal bovine serum, glutamic acid, and antibiotics was used as a medium.

As an expression vector, a chimera in which DNA binding domain of Gal4, which is a yeast transcription factor, and ligand binding domain of human PPARγ2 are fused, i.e., a fused product between the amino acids 1 to 147 of Gal4 transcription factor and the amino acids 182 to 505 of human PPARγ2, was used. Furthermore, as a reporter vector, a firefly luciferase containing five copies of Gal4 recognition sequence in the promoter region was used. Plasmid transfection to the cells was performed according to a method which uses jetPEI (trade name, manufactured by Funakoshi Co., Ltd., Tokyo, Japan). Furthermore, β-galactosidase expression vector was employed as an internal standard.

After the transfection into the cells, the medium was replaced with a DMEM medium (containing 1% serum) added with the test compound, and the cells were further cultured for 16 hours. After that, the luciferase activity and β-galactosidase activity in the cell lysis solution were measured.

Meanwhile, for the present test, dimethylsulfoxide (DMSO) was used for dissolution and dilution of the test compounds, and during the cell treatment, the DMSO concentration in DMEM medium (containing 1% serum) was adjusted to 0.1%. As a positive compound, rosiglitazone (trade name, manufactured by ALEXIS Corporation, Switzerland) was used. The percentage (%) of the luciferase activity of the each test compound (1 to 30 μmol/L) was calculated when the luciferase activity of rosiglitazone (3 to 10 μmol/L) is 100% and the luciferase activity in the absence of the test compound is 0%. The 50% effective concentration of the test compound ($EC_{50}$, 50% effect concentration) was calculated by using SAS Preclinical Package Ver 5.0 (trade name, manufactured by SAS institute Japan Co., Tokyo, Japan), which is a statistical analysis program.

As a result, it was confirmed that the compounds described in the Examples have a PPARγ activation effect at the concentration of 30 μM. The $EC_{50}$ results are given in the Table 2. As shown in the Table 2, it was confirmed that the compounds of the invention have a potent PPARγ activation effect. In particular, several compounds in the Table 2 exhibited $EC_{50}$ value of less than 1 μM, indicating stronger PPARγ activation effect than telmisartan. Maximum activity strength of several compounds relative to the maximum activity of rosiglitazone is given in the Table 3. As shown in Table 3, it was confirmed that the compounds of the invention have an activity that is 20 to 69% of the maximum activity of rosiglitazone and they have a sufficient agonist activity on PPARγ. In particular, the maximum activity of the compounds of the Examples 40, 41, 42, and 43 was 42 to 69%, which is the same or greater than that of telmisartan. Under the same condition, the PPARγ activation effect of telmisartan, i.e., $EC_{50}$, was 1 to 5 μM, and the maximum activity strength of telmisartan relative to the maximum activity of rosiglitazone (i.e., % MAX vs. rosiglitazone) was 30 to 50%.

TABLE 2

| Example No. | $EC_{50}$ (μM) |
| --- | --- |
| 6 | 1.36 |
| 15 | 3.61 |
| 17 | 3.12 |
| 18 | 3.39 |
| 19 | 1.50 |
| 20 | 0.85 |
| 21 | 0.45 |
| 22 | 1.55 |
| 23 | 0.76 |
| 24 | 1.46 |
| 25 | 0.82 |
| 26 | 0.38 |
| 27 | 0.67 |
| 32 | 2.74 |
| 40 | 0.40 |
| 41 | 0.56 |
| 42 | 0.65 |
| 43 | 0.59 |

TABLE 3

| Example No. | % MAX vs Rosiglitazone |
| --- | --- |
| 40 | 69 |
| 41 | 65 |
| 42 | 53 |
| 43 | 42 |

From the results obtained above, it was confirmed that the compounds of the present invention have both a potent angiotensin II receptor antagonistic activity and a PPARγ activation effect. Thus, it was found that the compounds of the present invention and pharmaceutically acceptable salts thereof are useful as an effective component of a prophylactic and/or therapeutic agent for disorders involved with angiotensin II and PPARγ, for example, hypertension, heart diseases, angina pectoris, cerebral vascular disorders, cerebral circulatory disorders, ischemic peripheral circulatory disorders, renal diseases, arteriosclerosis, inflammatory diseases, type 2 diabetes, diabetic complications, insulin resistance syndrome, syndrome X, metabolic syndrome, and hyperinsulinemia.

INDUSTRIAL APPLICABILITY

The phenylpyridine derivatives represented by the formula (I) of the invention or salts thereof, or solvates thereof are a novel compound which have both an angiotensin II receptor antagonistic activity and a PPARγ activation effect, and the present invention provides the novel compounds and a pharmaceutical composition containing the same. The compounds of the invention are used as an effective component of a novel pharmaceutical product, i.e., a prophylactic and/or therapeutic agent for disorders involved with angiotensin II and PPARγ, for example, hypertension, heart diseases, angina pectoris, cerebral vascular disorders, cerebral circulatory disorders, ischemic peripheral circulatory disorders, renal diseases, arteriosclerosis, inflammatory diseases, type 2 diabetes, diabetic complications, insulin resistance syndrome, syndrome X, metabolic syndrome, and hyperinsulinemia, and therefore have an industrial applicability.

The invention claimed is:
1. A compound which is
3-{2-{5-{[1-(5-ethoxypyrimidin-2-yl)-2-isopropyl-6-oxo-4-propyl-1,6-dihydropyrimidin-5-yl]methyl}pyridin-2-yl}phenyl}-1,2,4-oxadiazol-5(4H)-one,
or a salt thereof, or a solvate thereof.

2. A method of treating a circulatory disease, the method comprising administering an effective amount of 3-{2-{5-{[1-(5-ethoxypyrimidin-2-yl)-2-isopropyl-6-oxo-4-propyl-1,6-dihydropyrimidin-5-yl]methyl}pyridin-2-yl}phenyl}-1,2,4-oxadiazol-5(4H)-one or a salt or solvate thereof to a patient who is in need of the treatment.

3. The method of treating a circulatory disease according to claim 2, wherein the circulatory disease is hypertension, heart disease, angina pectoris, cerebral vascular disorder, cerebral circulatory disorder, ischemic peripheral circulatory disorder, kidney disease, or arteriosclerosis.

* * * * *